US006486141B2

(12) United States Patent
Lau et al.

(10) Patent No.: US 6,486,141 B2
(45) Date of Patent: Nov. 26, 2002

(54) PHOSPHONIC ACID BIARYL DERIVATIVES AS INHIBITORS OF PROTEIN TYROSINE PHOSPHATASE 1B (PTP-1B)

(75) Inventors: Cheuk Kun Lau, Ile Bizard (CA); Christopher Bayly, Beaconsfield (CA); Jacques Yves Gauthier, Laval (CA); Yves Leblanc, Kirkland (CA); Chun Sing Li, Dollard Des Ormeaux (CA); Patrick Roy, Dollard Des Ormeaux (CA); Michel Therien, Laval (CA); Zhaoyin Wang, Kirkland (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/745,199

(22) Filed: Dec. 21, 2000

(65) Prior Publication Data
US 2002/0052346 A1 May 2, 2002

Related U.S. Application Data
(60) Provisional application No. 60/171,376, filed on Dec. 22, 1999.

(51) Int. Cl.[7] .......................... A61K 31/663; C07K 9/38
(52) U.S. Cl. ............................ 514/80; 562/23; 562/24; 562/25
(58) Field of Search ........................... 548/119; 562/23, 562/24, 25; 514/80

(56) References Cited

U.S. PATENT DOCUMENTS

6,066,715 A     3/2000   Desmarais et al.

FOREIGN PATENT DOCUMENTS

| WO | WO97/40017  | 10/1997 |
| WO | WO 98/20156 | 5/1998  |
| WO | WO99/31066  | 6/1999  |
| WO | WO99/47529  | 9/1999  |
| WO | WO 00 17211 | 3/2000  |

OTHER PUBLICATIONS

Ahmad, et al., J. Biol. Chem., vol. 270, pp. 20503–20508, 1995.
Bin, et al., Tetrahedron, vol. 52, No. 30, pp. 9963–9970.
Caplan, et al, Bioorganic & Medicinal Chem. Letters, vol. 8, No. 5, pp. 515–520.
Charbonneau, et al, Proc. Natl. Acad Sci. USA, vol. 86, pp. 5252–5256, 1989.
Fishcer, et al., Science, vol. 253, pp. 401–406, 1991.
Goldstein, Receptor vol. 3, pp. 1–15, 1993.
Kotoris, et al., J. Org. Chem., vol. 63, pp. 8052–8057, 1998.
Seely, et al., Diabetes, vol. 45, pp. 1379–1385, 1996.
Taylor, et al., Bioorg. Med. Chem., vol. 6(9), pp. 1457–1468, 1998.
Taylor, et al., Bioorg. Med. Chem., vol. 6, p. 2235, 1998.
Taylor, et al., Tetrahedron Letters, vol. 8, No. 45, pp. 8089–8092, 1996.
Taylor, et al., Tetrahedron, No. 54, pp. 1691–1714, 1998.
Wang, et al., Bioorg. Med. Chem., Let., vol. 8(4), pp. 345–350, 1998.
White, et al., J. Biol. Chem., vol. 269, pp. 1–4, 1994.
Yokomatsu, et al., Tetrahedron, vol. 54, No. 32, pp. 9341–9356.
Charifson, et al., Biochemistry, US, American Chemical Society, 1997, pp. 6283–6293, vol. 36—No. 21.
Desmarais, S., et al., Biochemical Journal, 1999, pp. 219–223, vol. 337—No. 2.
Taing, M., Biochemistry, 1999, pp. 3793–3803, vol. 38—No. 12.
Burke, et al., Bioorg. Med. Chem. Letters, vol. 9, pp. 347–352, 1999.
Yao, et al., Tetrahedron, vol. 55, pp. 2865–2874, 1999.
Beaulieu, et al . . ., J. Med. Chem., vol. 42, pp. 1757–1766, 1999.
Kotoris, et al., Bioorg. Med. Chem., vol. 8, pp. 3275–3280, 1998.

*Primary Examiner*—Robert Gerstl
(74) *Attorney, Agent, or Firm*—James L. McGinnis; Melvin Winokur

(57) ABSTRACT

The invention encompasses the novel class of compounds represented by formula I which are inhibitors of the PTP-1B enzyme.

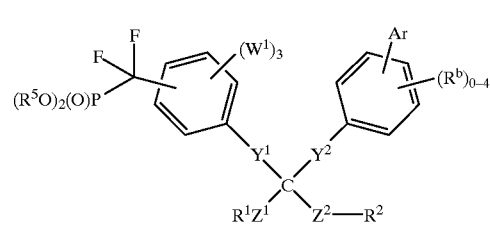

The invention also encompasses pharmaceutical compositions and methods of treating or preventing PTP-1B mediated diseases, including diabetes, obesity, and diabetes-related conditions.

28 Claims, No Drawings

PHOSPHONIC ACID BIARYL DERIVATIVES AS INHIBITORS OF PROTEIN TYROSINE PHOSPHATASE 1B (PTP-1B)

CROSS REFERENCE TO RELATED APPLICATIONS

This application is based on and claims priority from U.S. Provisional Application No. 60/171,376, which was filed on Dec. 22, 1999, and which is incorporated by reference into this application. Commonly assigned U.S. application Ser. No. 09/398,356, filed on Sep. 17, 1999, now U.S. Pat. No. 6,172,874, and commonly assigned U.S. application Ser. Nos. 09/745,220, 09/745,211 and 09/745,222, all filed on even date herewith, contain related subject matter.

BACKGROUND OF THE INVENTION

This invention relates to a novel class of phosphonic acid derivatives that are inhibitors of PTP-1B.

Protein tyrosine phosphatases are a large family of transmembrane or intracellular enzymes that dephosphorylate substrates involved in a variety of regulatory processes (Fischer et al., 1991, Science 253:401–406). Protein tyrosine phosphatase-1B (PTP-1B) is a ~50 kd intracellular protein present in abundant amounts in various human tissues (Charbonneau et al., 1989, Proc. Natl. Acad. Sci. USA 86:5252–5256; Goldstein, 1993, Receptor 3:1–15).

Determining which proteins are substrates of PTP-1B has been of considerable interest. One substrate which has aroused especial interest is the insulin receptor. The binding of insulin to its receptor results in autophosphorylation of the receptor, most notably on tyrosines 1146, 1150, and 1151 in the kinase catalytic domain (White & Kahn, 1994, J. Biol. Chem. 269:1–4). This causes activation of the insulin receptor tyrosine kinase, which phosphorylates the various insulin receptor substrate (IRS) proteins that propagate the insulin signaling event further downstream to mediate insulin's various biological effects.

Seely et al., 1996, Diabetes 45:1379–1385 ("Seely") studied the relationship of PTP-1B and the insulin receptor in vitro. Seely constructed a glutathione S-transferase (GST) fusion protein of PTP-1B that had a point mutation in the PTP-1B catalytic domain. Although catalytically inactive, this fusion protein was able to bind to the insulin receptor, as demonstrated by its ability to precipitate the insulin receptor from purified receptor preparations and from whole cell lysates derived from cells expressing the insulin receptor.

Ahmad et al., 1995, J. Biol. Chem. 270:20503–20508 used osmotic loading to introduce PTP-1B neutralizing antibodies into rat KRC-7 hepatoma cells. The presence of the antibody in the cells resulted in an increase of 42% and 38%, respectively, in insulin stimulated DNA synthesis and phosphatidyinositol 3' kinase activity. Insulin receptor autophosphorylation and insulin receptor substrate-1 tyrosine phosphorylation were increased 2.2 and 2.0-fold, respectively, in the antibody-loaded cells. The antibody-loaded cells also showed a 57% increase in insulin stimulated insulin receptor kinase activity toward exogenous peptide substrates.

Recently, Kennedy et al., 1999, Science 283: 1544–1548 showed that protein tyrosine phosphatase PTP-1B is a negative regulator of the insulin signalling pathway, suggesting that inhibitors of this enzyme may be beneficial in the treatment of Type 2 diabetes. Mice lacking PTP-1B are resistant to both diabetes and obesity.

Thus, inhibitors of PTP-1B improve insulin-sensitivity. They have utility in controlling or treating Type 1 and Type 2 diabetes, in improving glucose tolerance, and in improving insulin sensitivity in patients in need thereof. The compounds may also be useful in treating or preventing cancer, neurodegenerative diseases and the like.

SUMMARY OF THE INVENTION

Compounds represented by Formula I, including pharmaceutically acceptable salts thereof, and prodrugs thereof, are PTP-1B inhibitors and are useful in the treatment of diabetes, obesity, and related conditions.

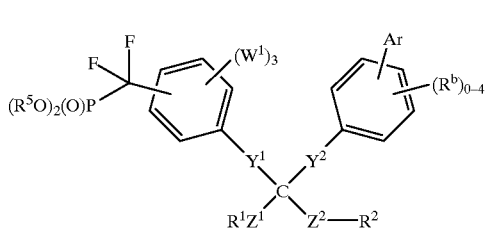

In these compounds, $R^1$ and $R^2$ are selected from the group consisting of $C_{1-10}$alkyl$(R^a)_{0-7}$, $C_{2-10}$alkenyl$(R^a)_{0-7}$, Aryl$(R^a)_{0-3}$ and Het$(R^a)_{0-3}$;

wherein, each $R^a$ independently represents a member selected from the group consisting of: Aryl, OH, halogen, $C_{0-6}$alkyleneCO$_2$H, $C_{0-6}$alkyleneCO$_2$C$_{1-6}$alkyl, OC$_{1-10}$alkyl, C$_{1-6}$alkyl, C$_{1-6}$haloalkyl, OC$_{1-10}$alkyleneCO$_2$H, S(O)$_y$C$_{1-6}$alkyl, S(O)$_y$NR$^{3'}$R$^{4'}$, and Het, wherein y is 0, 1, or 2;

Ar represents Aryl or Het, wherein said Aryl or Het is substituted with 1–5 substituents $R^b$, wherein optionally 2 $R^b$ groups can join together to form a 5–7 membered ring fused to Ar, where the fused portion of the 5–7 membered ring may be saturated or may include 1–2 double bonds and may include 1–4 heteroatoms selected from N, S, O, and C(=O) in the fused portion of the ring, said ring optionally being substituted with 1–3 groups independently selected from $R^a$;

Aryl is a 6–14 membered carbocyclic aromatic ring system comprising 1–3 phenyl rings, wherein said rings are fused together when there is more than one aromatic ring;

Het represents a 5–10 membered aromatic ring system comprising one ring or two fused rings, 1–4 heteroatoms, 0–4 of which are N atoms and 0–2 of which are or S(O)$_y$, wherein y is 0–2, and 0–2 carbonyl groups;

Each $R^b$ is independently selected from the group consisting of: OH, CN, halogen, $C_{0-6}$alkyleneOC$_{1-6}$alkyl$(R^a)_{0-7}$, $C_{0-6}$alkyleneOAryl$(R^a)_{0-3}$, Het, $C_{0-6}$alkyleneS(O)$_y$C$_{1-6}$alkyl$(R^a)_{0-7}$, with y equal to 0–2, $C_{0-6}$alkyleneS(O)$_3$H, $C_{1-10}$alkyl$(R^a)_{0-7}$, N$_3$, $C_{0-6}$alkyleneCO2H, $C_{0-6}$alkyleneCO$_2$C$_{1-6}$alkyl$(R^a)_{0-7}$, $C_{0-6}$alkyleneCO$_2$C$_{2-6}$ alkenyl$(R^a)_{0-7}$, $C_{0-6}$alkyleneC(O)C$_{1-6}$alkyl$(R^a)_{0-7}$, C(O)NR$^{3'}$R$^{4'}$, S(O)$_y$NR$^{3'}$R$^{4'}$, NR$^{3'}$R$^{4'}$, PO(OR$^5$)$_2$, and CF$_2$PO(OR$^5$)$_2$, wherein $R^{3'}$ and $R^{4'}$ are as defined above;

Each y is 0, 1 or 2;

Each $R^5$ is H;

$Y^1$, $Y^2$, $Z^1$ and $Z^2$ each independently represents —(CR$^3$R$^4$)$_a$-X-(CR$^3$R$^4$)$_b$— wherein a and b are each zero or an integer 1 or 2 such that the sum of a and b equals 0, 1, 2 or 3, X represents a bond, O, S(O)$_y$, NR$^{3'}$, C(O), OC(O), C(O)O, C(O)NR$^{3'}$, NR$^{3'}$(O) or —CH=CH—, where y is as previously defined;

$R^3$ and $R^4$ are independently H, halogen, $C_{1-10}$alkyl or $C_{1-10}$haloalkyl;

$R^{3'}$ is selected from the group consisting of: H, $C_{1-6}$alkyl, $C_{1-6}$haloalkyl, OH, $C(O)C_{1-6}$ alkyl, $C(O)$Aryl, $C(O)$Het, $C(O)C_{1-6}$ haloalkyl, Aryl and Het;

$R^{4'}$ is selected from the group consisting of: H, $C_{1-6}$alkyl, $C_{1-6}$haloalkyl, Aryl and Het;

Each $W^1$ is independently selected from the group consisting of: H, OH, CN, halogen, $OC_{1-6}$alkyl$(R^a)_{0-7}$, OAryl$(R^a)_{0-3}$, $S(O)_y C_{1-6}$alkyl$(R^a)_{0-7}$, with y equal to 0–2, $S(O)_3H$, $C_{1-6}$alkyl$(R^a)_{0-7}$, $N_3$, $C_{0-6}$alkyleneCO$_2$H, $C_{0-6}$alkyleneCO$_2$C$_{1-6}$ alkyl $(R^a)_{0-7}$, $C_{0-6}$alkyleneCO$_2$C$_{2-6}$ alkenyl$(R^a)_{0-7}$, $C_{0-6}$alkyleneC(O)C$_{1-6}$alkyl$(R^a)_{0-7}$, $C(O)NR^{3'}R^{4'}=$, $S(O)_yNR^{3'}R^{4'}$, $NR^{3'}R^{4'}$, Aryl and Het, wherein $R^{3'}$and $R^{4'}$ are as defined above; or alternatively two $W^1$ groups on adjacent atoms of the aromatic ring are joined together to form a fused phenyl ring, optionally substituted with 1–3 groups $R^b$.

Methods of treating, controlling, and preventing diabetes, obesity, and other related diseases and conditions using the compounds having Formula I are provided herein. Pharmaceutical compositions and combination therapies are also disclosed herein.

DETAILED DESCRIPTION OF THE INVENTION

In one embodiment of this invention, in compounds having Formula I, $W^1$ is independently selected from the group consisting of:

(a) hydrogen,
(b) halogen,
(c) $OC_{1-6}$alkyl$(R^a)_{0-7}$,
(d) $SC_{1-6}$alkyl$(R^a)_{0-7}$,
(e) $C_{1-6}$alkyl$(R^a)_{0-7}$,
(f) $CO_2H$,
(g) $CO_2$-$C_{1-6}$alkyl$(R^a)_{0-7}$,
(h) OH,
(l) $N(R^{3'})(R^{4'})$ and
(m) $C(O)C_{1-6}$alkyl$(R^a)_{0-7}$.

In another embodiment, each $W^1$ represents H or halogen.

In another embodiment, Ar represents phenyl, quinolinyl, indolyl or thienopyridinyl.

In a subset of compounds having Formula I, as described above, Ar represents phenyl, which is substituted with 1–2 substituents selected from $R^b$, and the phenyl ring to which Ar is connected is unsubstituted.

In a preferred subset of compounds of Formula I, $Y^1$, $Z^1$ and $Z^2$ are each independently $CH_2$ or a bond, and Y2 is selected from $CH_2$, a bond, —$CH_2CH_2SCH_2$—, —$CH_2CH_2OH_2$—, —$C(=O)OCH_2$—, —$C(=O)OCH_2CH_2$—, and —$C(=O)O$—.

In another subset of compounds of Formula I, $R^b$ is selected from the group consisting of: halogen, $C_{0-6}$alkyleneOC$_{1-6}$alkyl$(R^a)_{0-2}$, —$SC_{1-6}$alkyl$(R^a)_{0-2}$, -Ophenyl, tetrazole, $C_{1-10}$alkyl$(R^a)_{0-2}$, $C_{0-3}$alkyleneCO$_2$H, $C_{0-3}$alkyleneCO$_2$C$_{1-6}$alkyl$(R^a)_{0-2}$, $C(O)NR^{3'}R^{4'}$, $S(O)_yNR^{3'}R^{4'}$, $PO(OR^5)_2$, and $CF_2PO(OR^5)_2$, wherein $R^{3'}$ and $R^{4'}$ are individually selected from H and $C_{1-6}$alkyl, and $R^a$ is selected from OH, —$OC_{1-3}$alkyl, and phenyl.

In another group of compounds, $R^1$ and $R^2$ are selected from Aryl$(R^a)_{0-3}$ and Het$(R^a)_{0-3}$.

In many preferred compounds, $R_1$ and $R_2$ are selected from phenyl and 1H-1,2,3-Benzotriazolyl.

Finally specific compounds of Formula I are provided in Table 1, Table 2, and Examples 1–27. The compounds in Examples 1–27 are named below:

Example 1
{[4-(2-Benzotriazol-1-yl-3-biphenyl-4-yl-2-phenyl-propyl)-phenyl]difluoro-methyl}-phosphonic Acid Example 2
({4-[2-Benzotriazol-1-yl-2-phenyl-3-(2'-sulfamoyl-biphenyl-4-yl)-propyl]-phenyl}-difluoro-methyl)-phosphonic Acid Example 3
[(4-{2-Benzotriazol-1-yl-2-phenyl-3-[2'-(1H-tetrazol-5-yl)-biphenyl-4-yl]-propyl}-phenyl)-difluoro-methyl]-phosphonic Acid Example 4
(4'-{2-Benzotriazol-1-yl-3-[4-(difluoro-phosphono-methyl)-phenyl]-2-phenyl-propyl}-biphenyl-3-yl)-phosphonic Acid Diethyl Ester Example 5
(4'-{2-Benzotriazol-1-yl-3-[4-(difluoro-phosphono-methyl)-phenyl]-2-phenyl-propyl}-biphenyl-3-yl)-phosphonic Acid Example 6
({4-[2-Benzotriazol-1-yl-3-(4'-methylsulfanyl-biphenyl-4-yl)-2-phenyl-propyl]-phenyl}-difluoro-methyl)-phosphonic Acid Example 7
(4-{2-(1H-1,2,3-Benzotriazol-1-yl)-3-[4'(methylsulfanyl)(1,1'-biphenyl]yl]phenylpropyl}phenyl)(difluoro)methylphosphonic Acid Example 8
{4-[2-(1H-1,2,3-Benzotriazol-1-yl)-3-(3'phenoxy(1,1'-biphenyl]-3-yl)-2-phenylpropyl)phenyl}-(difluoro)methylphosphonic Acid Example 9
3-(2-(1H-1,2,3-Benzotriazol-1-yl)-3-(4-[difluoro(phosphono)methyl]phenyl}-2-phenylpropyl)(1,1'-biphenyl)]-3-ylphosphonic Acid Example 10
{4-[2-(1H-1,2,3-Benzotriazol-1-yl)-3-[(4-(2-carboxy-5-isopropoxyphenyl)benzyl)oxy]-3-oxo-2-phenylpropyl]phenyl}(difluoro)methylphosphonic Acid Example 11
{4-[2-(1H-1,2,3-Benzotriazol-1-yl)-3-[(4-(4-carboxy-3-isopropoxyphenyl)benzyl)oxy]-3-oxo-2-phenylpropyl]phenyl}(difluoro)methylphosphonic Acid Example 12
{4-[2-(1H-1,2,3-Benzotriazol-1-yl)-3-[(4-(3-t-butoxycarbonyl-5-isopropoxyphenyl)benzyl)oxy]-3-oxo-2-phenylpropyl]phenyl}(difluoro)methylphosphonic Acid Example 13
{4-[2-(1H-1,2,3-Benzotriazol-1-yl)-3-[(4-(3-carboxy-5-isopropoxyphenyl)benzyl)oxy]-3-oxo-2-phenylpropyl]phenyl}(difluoro)methylphosphonic Acid Example 14
(4-{2-(1H-1,2,3-Benzotriazol-1-yl)-3-[2'-(tert-butoxycarbonyl)-5'-isopropoxy(1,1'-biphenyl]-4-yl]-2-phenylpropyl}phenyl)(difluoro)methylphosphonic Acid Example 15
(4'-(2-(1H-1,2,3-Benzotriazol-1-yl)-3-{4-[difluoro(phosphono)methyl]phenyl}-2-phenylpropyl)-5-isopropoxy[1,1'-biphenyl]-2-carboxylic Acid

Example 16

(4-{2-(1H-1,2,3-benzotriazol-1-yl)-3-[4'-(tert-butoxycarbonyl)-3'-isopropoxy[1,1'-biphenyl]-4-yl]-2-phenylpropyl}phenyl) (difluoro)methylphosphonic Acid

Example 17

(4-{2-Benzotriazol-1-yl-4-[2'-(1H-tetrazol-5-yl)-biphenyl-4-ylmethylsulfanyl]-2-phenyl-butyl}-phenyl)-difluoro-methyl-phosphonic Acid

Example 18

[6-(4-{2-Benzotriazol-1-yl-3-[4-(difluoro-phosphono-methyl)-phenyl]-2-phenyl-propyl}-phenyl)-2-methyl-quinolin-8-yl]-phosphonic Acid

Example 19

[6-(4-{2-Benzotriazol-1-yl-3-[4-(difluoro-phosphono-methyl)-phenyl]-2-phenyl-propyl}-phenyl)-2-(1-methoxy-3-methyl-butyl)-quinolin-8-yl]-phosphonic Acid

Example 20

[6-(4-{2-Benzotriazol-1-yl-3-[4-(difluoro-phosphono-methyl)-phenyl]-2-phenyl-propyl}-phenyl)-2-(1-methoxymethoxy-3-methyl-butyl)-quinolin-8-yl]-phosphonic Acid Diethyl Ester

Example 21

[6-(4-{2-Benzotriazol-1-yl-3-[4-(difluoro-phosphono-methyl)-phenyl]-2-phenyl-propyl}-phenyl)-2-(1-ydroxy-3-methyl-butyl)-quinolin-8-yl]-phosphonic Acid

Example 22

[(4-{2-Benzotriazol-1-yl-3-[4-(5-methoxycarbonyl-thieno[3,2-b-pyridin-3-yl)-phenyl]-2-phenyl-propyl}-phenyl)-difluoro-methyl]-phosphonic Acid

Example 23

3-(4-{2-Benzotriazol-1-yl-3-[4-(difluoro-phosphono-methyl)-phenyl]-2-phenyl-propyl}-phenyl)-thieno[3,2-b]pyridine-5-carboxylic Acid Trisodium Salt

Example 24

[4-(1-Benzotriazol-1-yl-2-biphenyl-3-yl-2-hydroxy-1-phenylethyl)phenyl]difluoromethylphosphonic Acid

Example 25

4'(2-(1H-1,2,3-Benzotriazol-1-yl)-3-{4-[difluoro(phosphono)methyl]phenyl}-2-phenylpropyl)(1,1'-biphenyl]-3-carboxylic Acid

Example 26

4'-{2-Benzotriazol-1-yl-3-[4-(difluorophosphonomethy)phenyl]-2-phenylpropyl}-4-methoxybiphenyl-3-yl-phosphonic Acid

Example 27

4'-{2-Benzotriazol-1-yl-3-[4-(difluorophosphonomethy)phenyl]-2-phenylpropyl}-4-(3-methylbutoxy)biphenyl-3-yl-phosphonic Acid Methods of treating, preventing, or controlling diabetes and other diseases using the compounds of Formula I are disclosed herein. A method of treating, controlling or preventing diabetes and complications thereof in a mammalian patient in need of such treatment includes the administration to the patient an anti-diabetic effective amount of a compound of Formula I. A method of treating, controlling or preventing obesity in a mammalian patient in need of such treatment comprises the administration to the patient an anti-obesity effective amount of a compound in accordance with claim 1. Such methods also include the administration of a second compound, which may be an anti-diabetic compound, an anti-obesity compound, or an HMG-CoA reductase inhibitor, in an amount effective to treat, control or prevent diabetes or obesity, or to improve a poor lipid profile.

A method of treating, controlling or preventing atherosclerosis in a mammalian patient in need of such treatment comprises administering to the patient an effective amount of a compound of Formula I and an effective amount of an HMG-CoA reductase inhibitor.

More generally, compounds of Formula I may be used as the active compound in a method for treating, preventing, or controlling one or more diseases or conditions selected from Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease. The method comprises the administration of an effective amount of the compound of Formula I. Combination treatments can also be used in which case, the method comprises the administration of a compound of Formula I and an effective amount of one or more pharmaceutically active compounds selected from the group consisting of an HMG-CoA reductase inhibitor, an anti-obesity agent, and an antidiabetic compound.

Pharmaceutical compositions also can be made using the compounds of Formula I. Compositions that are suitable for the treatment, prevention or control of one or more diseases or conditions selected from Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease contain an effective amount of a compound of Formula I in combination with a pharmaceutically acceptable carrier.

Such pharmaceutical compositions may also include a second anti-diabetic agent or an anti-obesity agent. They may also include a cholesterol lowering agent. Pharmaceutical compositions may therefore include: (1) an effective amount of a compound of Formula I, (2) an effective amount of one or more pharmaceutically active compounds selected from the group consisting of an HMG-CoA reductase inhibitor, an anti-obesity agent, and an anti-diabetic agent, and (3) a pharmaceutically acceptable carrier.

Such pharmaceutical compositions that contain a second active compound or composition and that are suitable for the treatment, prevention or control of one or more diseases or conditions selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, may be comprised of the following:
(1) an effective amount of a compound of Formula 1;
(2) an effective amount of one or more pharmaceutically active compounds listed below; and
(3) a pharmaceutically acceptable carrier; where the pharmaceutically active compounds are selected from the group consisting of:
  (a) insulin sensitizers including (i) PPARγ agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin;
  (b) insulin or insulin mimetics;
  (c) sulfonylureas such as tolbutamide and glipizide, or related materials;
  (d) α-glucosidase inhibitors (such as acarbose);
  (e) cholesterol lowering agents such as (i) HMG-CoA reductase inhibitors (lovastatin, simvastatin and pravastatin, fluvastatin, atorvastatin, rivastatin and other statins), (ii) sequestrants (cholestyramine, colestipol and a dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) inhibitors of cholesterol absorption, for example beta-sitosterol, and acyl CoA:cholesterol acyltransferase inhibitors, for example melinamide and (vi) probucol;
  (f) PPARα/γ agonists;
  (g) antiobesity compounds such as appetite suppressants, fenfluramine, dexfenfluramine, phentiramine, sulbitramine, orlistat, neuropeptide Y5 inhibitors (NP Y5 receptor antagonosts), leptin, which is a peptidic hormone, β3 adrenergic receptor agonists, and PPARγ antagonists and partial agonists;
  (h) ileal bile acid transporter inhibitors; and
  (i) insulin receptor activators.

Abbreviations

The following abbreviations have the indicated meanings:
AA=arachidonic acid
Ac=acetyl
AIBN=2.2'-azobisisobutyronitrile
Bn=benzyl
BSA=bovine serum albumin
Bz=benzoyl
CHO=chinese hamster ovary
CMC=1-cyclohexyl-3-(2-morpholinoethyl)carbodiimidemetho-p-toluenesulfonate
DAST=diethylamino sulfur trifluoride
DBU=diazabicyclo[5.4.0]undec-7-ene
DMAP=4-(dimethylamino)pyridine
DMF=N,N-dimethylformamide
DMSO=dimethyl sulfoxide
Et$_3$N=triethylamine
HATU=O-(7-azabenzotriazol-1-yl)-1,1,3,3-tetramethyluronium hexafluorophosphate
HBSS=Hanks balanced salt solution
HEPES=N$^1$-[2-Hydroxyethyl]piperazine-N$^4$-[2-ethanesulfonic acid]
HWB=human whole blood
KHMDS=potassium hexamethyldisilazane
LDA=lithium diisopropylamide
LPS=lipopolysaccharide
mCPBA=metachloro perbenzoic acid
MMPP=magnesium monoperoxyphthalate
Ms=methanesulfonyl=mesyl
MsO=methanesulfonate=mesylate
NBS=N-bromosuccinimide
NCS=N-chlorosuccinimiide
NIS=N-iodosuccinimide
NSAID=non-steroidal anti-inflammatory drug
Oxone®=potassium peroxymonosulfate
PCC=pyridinium chlorochromate
PDC=pyridinium dichromate
PPA=polyphosphoric acid
PTP=protein tyrosine phosphatase
r.t.=room temperature
rac.=racemic
Tf=trifluoromethanesulfonyl=triflyl
TFA=trifluoroacetic acid
TFAA=trifluoroacetic anhydride
TfO=trifluoromethanesulfonate=triflate
THF=tetrahydrofuran
TLC=thin layer chromatography
Ts=p-toluenesulfonyl=tosyl
TsO=p-toluenesulfonate=tosylate
Tz=1H (or 2H)-tetrazol-5-yl Alkyl Group Abbreviations
Me=methyl
Et=ethyl
n-Pr=normal propyl
i-Pr=isopropyl (occasionally written "pri")
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl Dose Abbreviations
bid=bis in die=twice daily
qid=quater in die=four times a day
tid=ter in die=three times a day Alkyl means linear, branched and cyclic structures, and combinations thereof, containing the indicated number of carbon atoms. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, cyclopropyl, cyclopentyl, cycloheptyl, adamantyl, cyclododecylmethyl, 2-ethyl-1- bicyclo[4.4.0]decyl and the like.

Fluoroalkyl means alkyl groups of the indicated number of carbon atoms in which one or more hydrogens is replaced by fluorine. Examples are —CF$_3$, —CH$_2$CH$_2$F, —CH$_2$CF$_3$, c-Pr-F$_5$, c-Hex-F$_{11}$ and the like. Haloalkyl has the analogous meaning for replacement of one or more hydrogen atoms with any halogen (Cl, Br, F, and/or I).

Alkenyl means linear, branched and cyclic structures, and combinations thereof containing a double bond with the indicated number of carbon atoms. Examples of alkenyl groups include allyl, 2-butenyl, 3-butenyl, 2-pentenyl, 2-cyclopentenyl, 3-cyclopentenyl, 2-methyl-cyclohexenyl, 2-cyclohexenyl, 3-cyclohexenyl and the like. Alkadienyl means the diunsaturated counterpart to alkenyl.

Alkynyl means linear, branched and cyclic structures, and combinations thereof containing a triple bond with the indicated number of carbon atoms. Examples of alkynyl groups include propargyl, 2-butynyl, 3-butynyl, 2-pentynyl, cyclopropylethynyl, and the like.

Alkylene, alkenylene, alkynylene, fluoroalkylene, alkadienylene, and the like, where the suffix "ene" has been added to the name of the monovalent radicals alkyl, alkenyl, alkynyl, fluoroalkyl, alkadienyl, and the like, describe divalent radicals that are the same as their monovalent counterparts, except that two hydrogen atoms rather than one are removed so that the radical will have two attachments.

Aryl means a 6–14 membered carbocyclic aromatic ring system comprising 1–3 phenyl rings. If two or more aromatic rings are present, then the rings are fused together, so that adjacent rings share a common side.

Heteroaryl (Het) as used herein represents a 5-10 membered aromatic ring system containing one ring or two fused rings, 1-4 heteroatoms, 0-4 of which are N atoms and 0-2 of which are O or $S(O)_y$ wherein y is as previously defined, and 0-2 carbonyl groups. Carbonyl groups, when present, are not counted as heteroatoms. Het includes, but is not limited to, furanyl, diazinyl, imidazolyl, isooxazolyl, isothiazolyl, oxadiazolyl, oxazolyl, pyrazolyl, pyridyl, pyrrolyl, tetrazinyl, thiazolyl, thienyl, triazinyl, triazolyl, 1H-pyrrole-2,5-dionyl, 2-pyrone, 4-pyrone, pyrrolopyridine, furopyridine and thienopyridine.

Benzoheteroaryl, which is a subset of Het includes aromatic ring systems containing one or more heteroatoms which also have a fused 6-membered benzene ring, such as 2H-1-benzopyran-2-one, 4H-1-benzopyran-4-one, 2(3H)benzofuranone, 3(2H)benzofuranone, 2,3-dihydrobenzofuran, 2,3-dihydrobenzothiophene, indole, benzofuran, benzothiophene, benzimidazole, benzoxazole, benzothiazole, benzotriazole, benzothiadiazole, 1H-isoindole-1,3(2H)-dione, quinoline, and isoquinoline.

Another subset of heteroaryls includes 5-membered heteroaryls, such as the following:

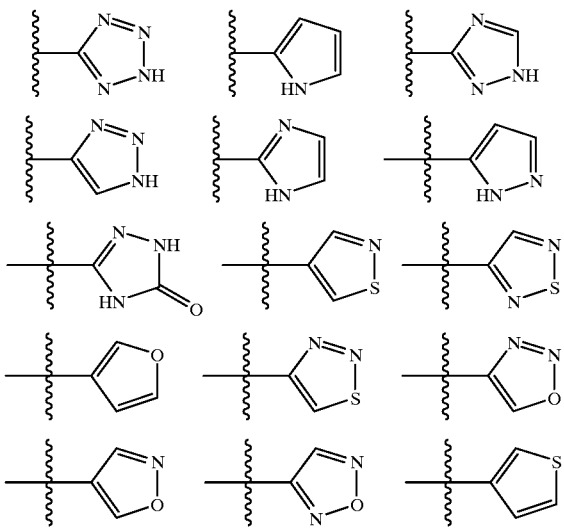

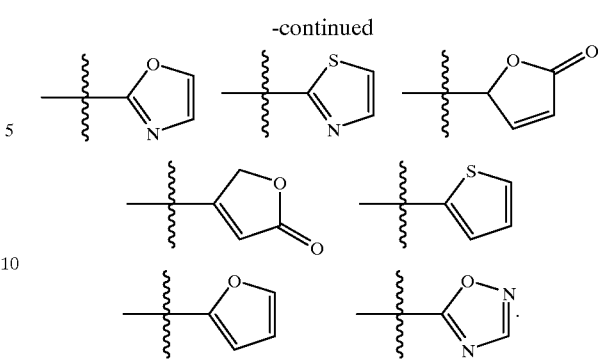

When a heteroaromatic ring is specified as optionally having one or more heteroatoms, this means that at least one heteroatom is present, selected from O, S and N, and up to 4 such heteroatoms may be present, depending upon the size of the ring specified.

When a moiety is specified as being optionally substituted, then the same moiety may also remain unsubstituted, unless otherwise stated.

Finally, when a list of possible choices is provided for a given moiety, and the moiety is used in more than one position in a chemical formula, the selection of a choice for the moiety in each position is independent of other selections, unless the definition says otherwise.

Metabolites—Prodrugs

Metabolites of the compounds of this invention that are therapeutically active and that are described by formula I also are within the scope of the claimed invention, as are prodrugs, which are compounds that are converted to the claimed active compounds or salts of the claimed active compounds after they have been administered to a patient. A non-limiting example of a prodrug of the phosphonic acids of this invention would be a monoester or diester of one or more phosphonic acid groups, where the ester functionality preferably has a structure that makes it easily hydrolyzed or metabolized after administration to a patient. Examples of prodrugs include $C_{1-6}$ alkyl esters of the phosphonic acids. Prodrugs that have structures that are more easily hydrolyzed or metabolized are generally more preferred. Examples are illustrated by the structures below, where R'=H or a $C_{1-6}$alkyl group, and R"=$C_{1-6}$ alkyl group or —$OC_{1-6}$ alkyl group, and Q is the residue of the molecule that is attached to the —$CF_2PO_3H_2$ or —$PO_3H_2$ group in formula I. The alkyl groups and alkoxy groups may optionally be substituted with one or more substituents independently selected from 1–5 halogen atoms, a phenyl group, or a mixture of these. The phenyl group, if present, may optionally be substituted with 1–3 substituents independently selected from halogen, —$CH_3$, —$CF_3$, —$OCH_3$ and —$OCF_3$. In these compounds, and as defined in general throughout this application, the alkyl groups and the alkyl portions of Oalkyl groups may be linear or branched and may optionally be cycloalkyl or may include a cycloalkyl group in their structure. For examples of prodrug structures related to those shown below, see D. N. Srinivasta et al., Bioorganic Chemistry 12, 118–129 (1984).

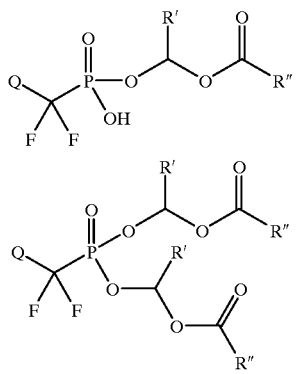

Other ester functionalities that may be used in the monoester or diester phosphonate prodrugs include phenyl esters and benzyl esters, where the phenyl ester groups have the structure -Ophenyl, and the benzyl ester groups have the structure —OCHR'phenyl, in which R is H or $C_{1-6}$alkyl, and $C_{1-6}$alkyl is substituted as described above. In either case, phenyl is substituted as described above.

The prodrugs of this invention may therefore be defined as compounds having the formula I, in which at least one group $R^5$ is selected from the group consisting of $C_{1-6}$alkyl, phenyl, —CHR'phenyl, and —CHR'OC(=O)R", and the remaining groups $R^5$ are selected from H, $C_{1-6}$alkyl, phenyl, —CHR'phenyl and —CHR'OC(=O)R", wherein each group R' is H or $C_{1-6}$alkyl and each group R" is —$C_{1-6}$alkyl or —O$C_{1-6}$alkyl, where $C_{1-6}$alkyl and the alkyl portion of —O$C_{1-6}$alkyl may optionally be substituted with one or more substituents independently selected from 1–5 halogen atoms, a phenyl group, or a mixture of these. The phenyl group in —CHR'phenyl, the phenyl group that is an optional substituent on $C_{1-6}$alkyl and —O$C_{1-6}$alkyl, and the phenyl ester group that is obtained when $R^5$ is phenyl may optionally be substituted with 1–3 groups independently selected from halogen, —$CH_3$, —$CF_3$, —$OCH_3$ and —$OCF_3$. By this definition, at least one of the phosphonic acid groups is a monoester or diester, and each of the remaining phosphonic acid groups, if any, may be a free acid or a monoester or diester.

In preferred compounds, the groups $R^5$ that are not H may all be the same because of the difficulty of synthesizing different $R^5$ groups on the same phosphonates. In many cases, the prodrug will be a mixture of compounds having different levels of esterification on the phosphonic acid groups because of the difficulty of synthesizing and separating a discrete pure compound.

Optical Isomers—Diastereomers—Geometric Isomers

Some of the compounds described herein contain one or more asymmetric centers, and these asymmetric centers may give rise to diastereomers and enantiomers, which may be in the form of enantiomeric or diastereomeric mixtures or of individual optical isomers. The present invention includes all such diastereomers and enantiomers, including racemic mixtures and resolved, enantiomerically pure forms, and pharmaceutically acceptable salts thereof. Some of the compounds described herein contain olefinic double bonds, and unless specified otherwise, include both E and Z geometric isomers.

Salts

The pharmaceutical compositions of the present invention comprise a compound of the current invention as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable acids, including inorganic and organic acids. Such acids include acetic, adipic, aspartic, 1,5-naphthalenedisulfonic, benzenesulfonic, benzoic, camphorsulfonic, citric, 1,2-ethanedisulfonic, ethanesulfonic, ethylenediaminetetraacetic, fumaric, glucoheptonic, gluconic, glutamic, hydriodic, hydrobromic, hydrochloric, isethionic, lactic, maleic, malic, mandelic, methanesulfonic, mucic, 2-naphthalenesulfonic, nitric, oxalic, pamoic, pantothenic, phosphoric, pivalic, propionic, salicylic, stearic, succinic, sulfuric, tartaric, p-toluenesulfonic acid, undecanoic, 10-undecenoic, and the like. Particularly preferred are citric, hydrobromic, hydrochloric, maleic, methanesulfonic, phosphoric, sulfuric and tartaric acids.

It will be understood that in the discussion of methods of treatment or of specific compounds which follows, references to the compounds of Formula I and other formulae are meant to include the pharmaceutically acceptable salts.

Utilities

Inhibitors of PTP-1B improve insulin-sensitivity and thus have utility in preventing or treating Type 1 and Type 2 diabetes, improving glucose tolerance and insulin-sensitivity when there is insulin-resistance, and in treating or preventing obesity, all in mammals that are in need of such treatments or that might benefit from such treatments. The compounds also exhibit a beneficial reduction in triglycerides and lipids. Compounds in the present class of phosphonic acids are advantageous over known phosphonic acids previously investigated as candidate PTP-1B inhibitors. The compounds of this invention show greater selectivity for PTP-1B over T-Cell Protein Tyrosine Phosphatase (TCPTP) when compared with known phosphonates. This advantage minimizes possible toxicity due to the inhibition of TCPTP activity. These compounds are also active in intact cell-based assays.

The PTP-1B inhibitors may also be useful in the treatment, prevention or control of a number of conditions that accompany type 2 diabetes, including hyperlipidemia, hypertriglyceridemia, hypercholesterolemia (including beneficially raising low HDL levels), atherosclerosis, vascular restenosis, pancreatitis, adipose cell tumors, adipose cell carcinomas such as liposarcoma, dyslipidemia, inflammatory bowel disease, inflammation in general, and other disorders where insulin resistance is a component. Finally, the compounds may be used to treat or prevent cancer, such as prostate cancer, neurodegenerative diseases and the like.

Pharmaceutical Compositions

For the treatment of any of these PTP-1B-mediated diseases the active compound may be administered orally, topically, parenterally, by inhalation spray or rectally in dosage units containing conventional pharmaceutically acceptable carriers. The term parenteral as used herein includes subcutaneous, intravenous, intramuscular and intrasternal injection and infusion techniques. In addition to the treatment of warm-blooded animals such as mice, rats, horses, cattle, sheep, dogs, cats, etc., the compounds of the invention are useful for the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxy-ethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical composition may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent, for example as a solution in 1,3-butanediol. Examples of vehicles and solvents include water, Ringer's solution and isotonic sodium chloride. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds may also be administered in the form of suppositories. These compositions can be prepared by mixing the drug with a suitable non-irritating excipient which is solid at ordinary temperatures but molten at the body temperature and will therefore release the drug. Such materials include cocoa butter and polyethylene glycols.

For topical use, creams, ointments, gels, solutions or suspensions containing the compound are employed. (For purposes of this application, topical application includes mouth washes and gargles.) Topical formulations may include cosolvents, emulsifiers, penetration enhancers, preservatives, emollients and the like.

The pharmaceutical composition may also be further comprised of a second anti-diabetic or anti-obesity effective compound.

Dose Ranges

Dosage levels on the order of from about 0.01 mg to about 100 mg/kg of body weight per day are useful in the treatment of the above-indicated conditions, or alternatively about 0.5 mg to about 7 g per patient per day. For example, the diseases and conditions described herein may be effectively treated by the administration of from about 0.01 to 50 mg of the compound per kilogram of body weight per day, or alternatively about 0.5 mg to about 3.5 g per patient per day.

The active ingredient is typically combined with the carrier to produce a dosage form suitable for the particular patient being treated and the particular mode of administration. For example, a formulation intended for the oral administration of humans may contain from about 0.5 mg to about 5 g of the active agent, compounded with an appropriate and convenient amount of carrier material which may vary from about 5 to about 95 percent of the total composition. Representative dosage forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It is understood that the specific dose level for any particular patient will depend upon a variety of factors including the age, body weight, general health, sex, diet, time of administration, route of administration, rate of excretion, drug combination and the severity of the particular disease undergoing therapy.

Combinations with Other Drugs

In further aspects, the invention encompasses pharmaceutical compositions for treating PTP-1B mediated diseases as defined above comprising an effective amount of the active compound and one or more other pharmaceutically active compounds, such as anti-diabetic compounds (for example, insulin, sulfonyl ureas, PPAR-alpha and/or -gamma ligands, including ligands that have both PPAR-alpha and -gamma activity), anti-obesity compounds, and compounds that improve the lipid profile of the patient.

Thus, the methods of treatment or prevention described herein may further be comprised of administering to said patient a second anti-diabetic compound in an amount effective to treat, control, or prevent diabetes, alone or in combination with the PTP-1B inhibitors of this invention.

Similarly, the methods of treatment or prevention described herein may further be comprised of administering to said patient an anti-obesity compound in an amount effective to treat, control or prevent obesity, alone or in combination with the PTP-1B inhibitors of this invention.

Similarly, the methods of treatment of diabetes may comprise the administration of a cholesterol biosynthesis inhibitor, particularly an HMG-CoA reductase inhibitor, such as lovastatin, simvastatin, pravastatin, fluvastatin, atorvastatin and rivastatin, in an amount effective to improve the lipid profile. In combination with a PTP-1B inhibitor, this may be beneficial in treating or preventing atherosclerosis and other conditions that often are associated with Type 2 diabetes.

Examples of other pharmaceutically active compounds that may be combined with a compound of Formula I and administered in combination with the PTP-1B inhibitors include, but are not limited to, the following compounds or compositions or groups of compounds or compositions that are used as anti-diabetes compounds (a, b, c, d, f, and i below), anti-obesity compounds (g below), and/or compounds or compositions for lipid profile control (e and h below):

(a) insulin sensitizers including (i) PPARγ agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin;

(b) insulin or insulin mimetics;

(c) sulfonylureas such as tolbutamide and glipizide, or related materials;

(d) α-glucosidase inhibitors (such as acarbose);

(e) cholesterol lowering agents such as (i) HMG-CoA reductase inhibitors (lovastatin, simvastatin and pravastatin, fluvastatin, atorvastatin, rivastatin and other statins), (ii) sequestrants (cholestyramine, colestipol and a dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and benzafibrate), (v) inhibitors of cholesterol absorption for example beta-sitosterol and (acyl CoA:cholesterol acyltransferase) inhibitors for example melinamide and (vi) probucol;

(f) PPARα/γ agonists;

(g) antiobesity compounds such as appetite suppressants, fenfluramine, dexfenfluramine, phentiramine, sulbitramine, orlistat, neuropeptide Y5 inhibitors (NP Y5 receptor antagonosts), leptin, which is a peptidic hormone, β3 adrenergic receptor agonists, and PPARγ antagonists and partial agonists;

(h) ileal bile acid transporter inhibitors; and (i) insulin receptor activators, such as those disclosed in copending, commonly assigned U.S. application Ser. Nos. 09/095,244 and 09/280,602.

Where a second pharmaceutical is used in addition to an active compound taught herein, the two pharmaceuticals may be administered together in a single composition, separately at approximately the same time, or on separate dosing schedules. The important feature is that their dosing schedules comprise a treatment plan in which the dosing schedules overlap in time and thus are being followed concurrently.

Methods of Synthesis

The compounds of the present invention can be prepared according to the following methods.

Method A

Di-tert-butyl phosphite can be deprotonated with a base such as LiN(TMS)2 and reacted with a tolualdehyde to provide alcohol 2, which may be oxidized with MnO2 or under Swern's conditions to give phosphonoketone 3. Bromination of 3 with NBS followed by fluorination with DAST affords bomide 5, which can be used for the alkylation of various 1-benzyl-1H-benzotriazole to give compound 7. Alkylation of 7 under the same condition with an appropriately substituted biphenyl benzyl bromide 8 gives compound 9 which hydrolyses under acid conditions to give product 10.

Method A

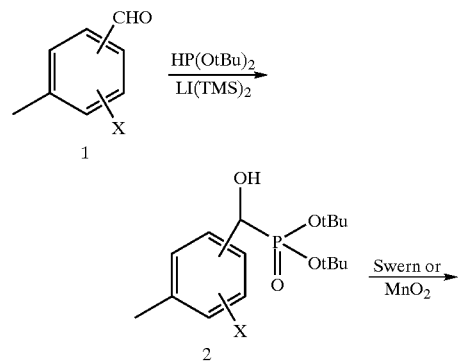

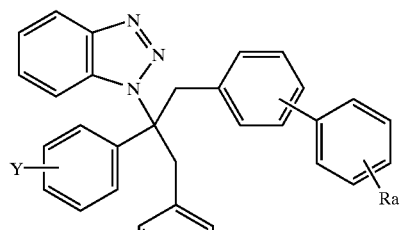
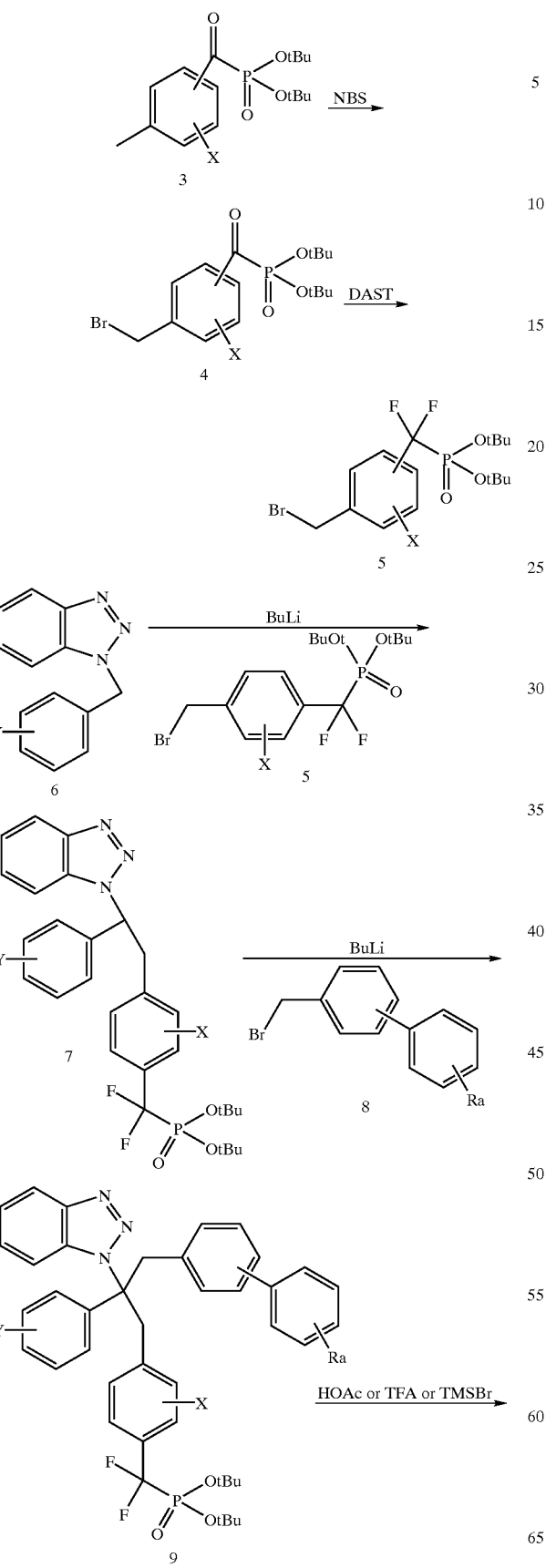
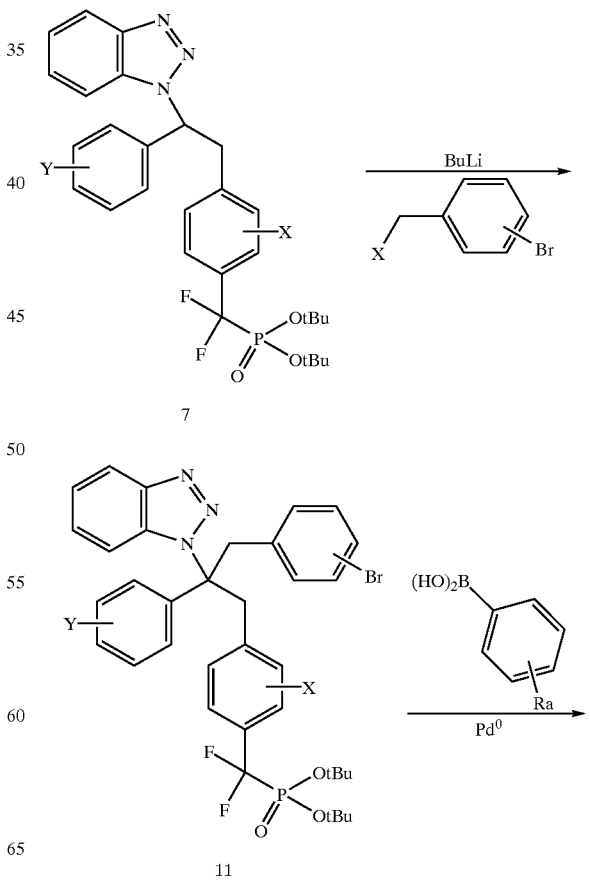
Method B
Compound 7 can be alkylated with a bromosubstituted benzyl halide to give compound 11 which can then undergo a palladium catalyzed coupling reaction with a substituted phenylboronic acid to give compound 9.

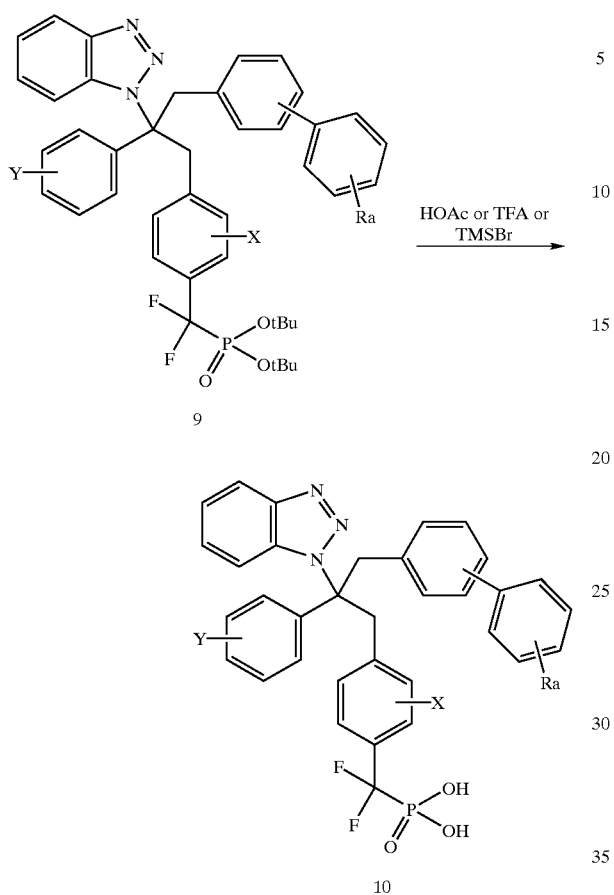

9

10

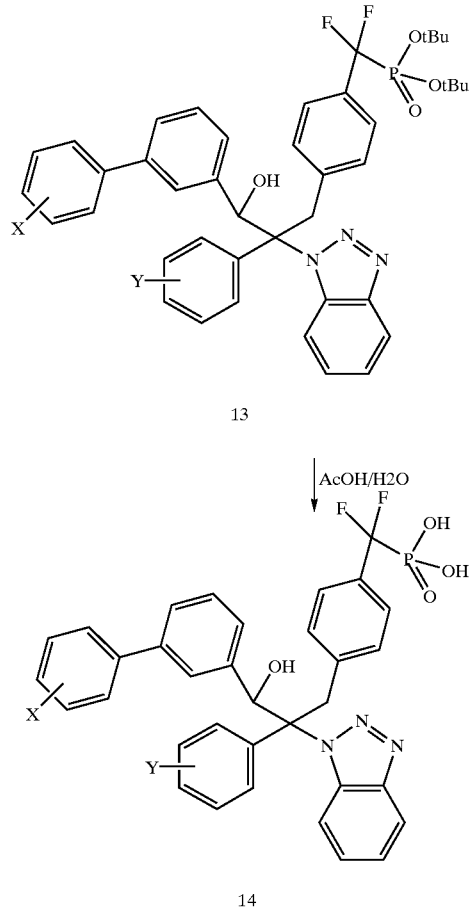

13

↓ AcOH/H2O

14

Method D

Alkylation of benzotriazole with methyl 2-bromophenylacetate 15 gives the ester 16. Hydrolysis of ester 16 followed by alkylation of the corresponding acid with the benzyl alcohol gives the benzyl ester 17. Alkylation of benzyl ester 17 with the phosphonobenzyl bromide 5 gives compound 18. Hydrogenation of the benzyl ester 18 in the presence of palladium gives the corresponding acid 19 which can be alkylated with a bromomethylbiphenyl 8 to give the ester 20. Acid hydrolysis of ester 20 gives the product 21.

Method C

Compound 7 can be alkylated with a substituted biphenyl aldehyde 12 to give compound 13, acid hydrolysis of compound 13 gives product 14.

Method C

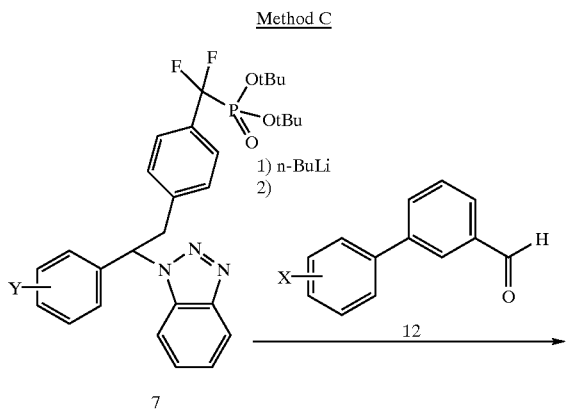

Method D

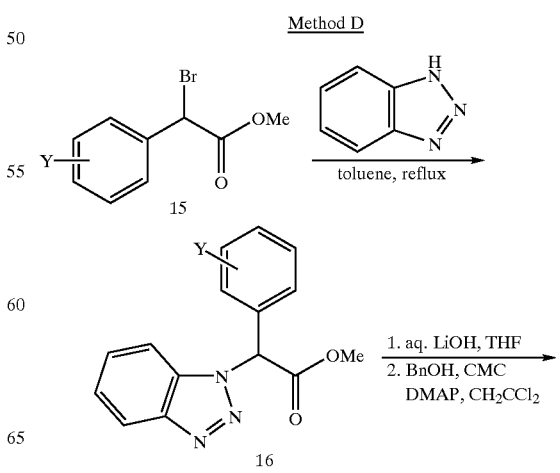

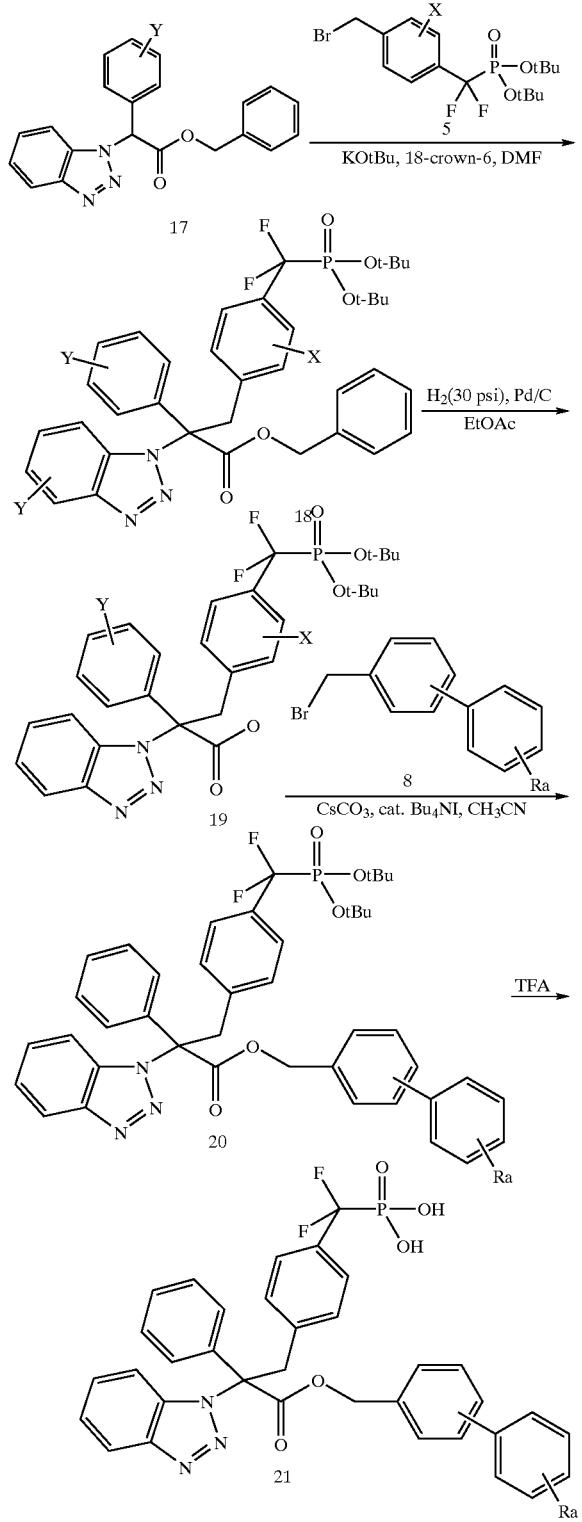

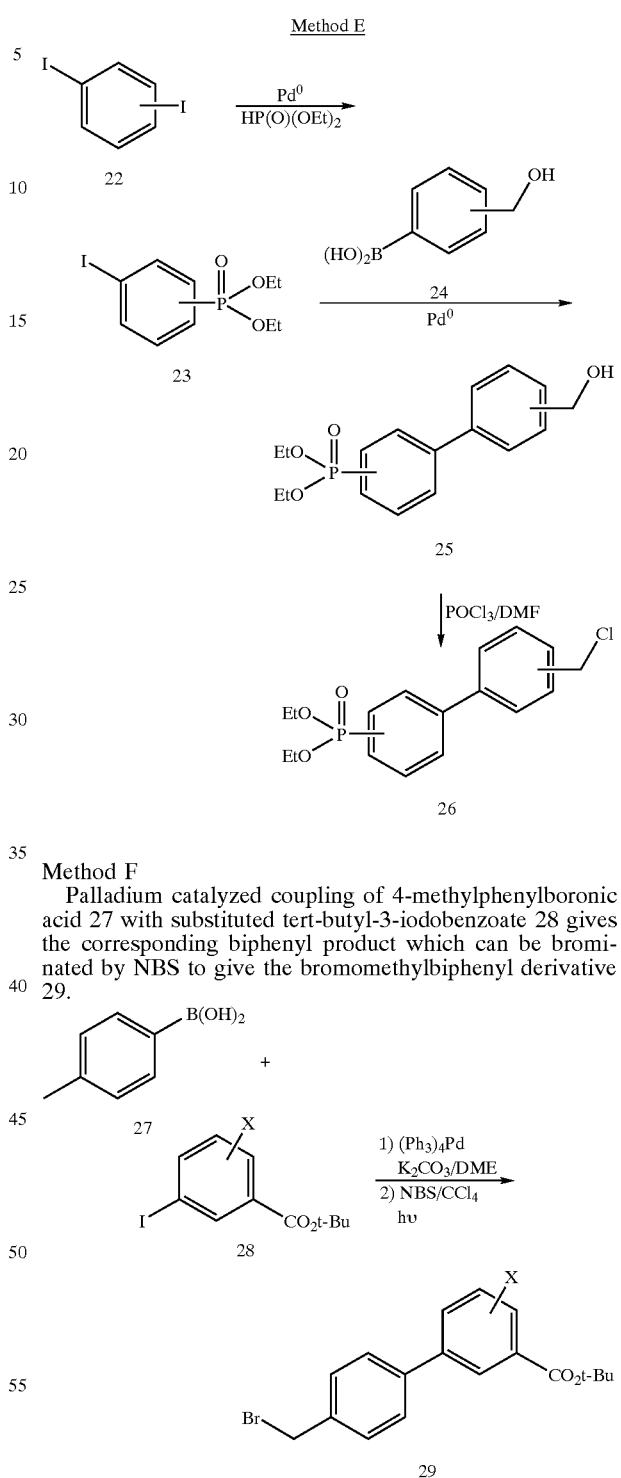

Many methods are available for the synthesis of halomethybiphenyl 8. Some of the methods are described below.

Method E

Reaction of diiodobenzene with diethylphosphine in the presence of palladium catalyst gives the iodophosphonate 23. Coupling of the iodide 23 with hydroxymethylboronic acid 24 in the presence of palladium gives the corresponding hydroxymethylbiphenyl 25 which can be converted to the corresponding halide using POCl$_3$/DMF.

Method F

Palladium catalyzed coupling of 4-methylphenylboronic acid 27 with substituted tert-butyl-3-iodobenzoate 28 gives the corresponding biphenyl product which can be brominated by NBS to give the bromomethylbiphenyl derivative 29.

Method G

Monoalkylation of methyl dihydroxybenzoate with an alkyl halide gives a mixture of monoalkoxy hydroxybenzoate 31. The hydroxybenzoate 31 can be converted to the corresponding triflate 32 which can undergo palladium catalyzed coupling reaction with 4-methylphenylboronic acid to give the biphenyl derivative 33. The methyl ester can then be exchanged to the corresponding t-butyl ester 34.

Bromination of 34 gives the bromomethylbiphenyl derivative 35.

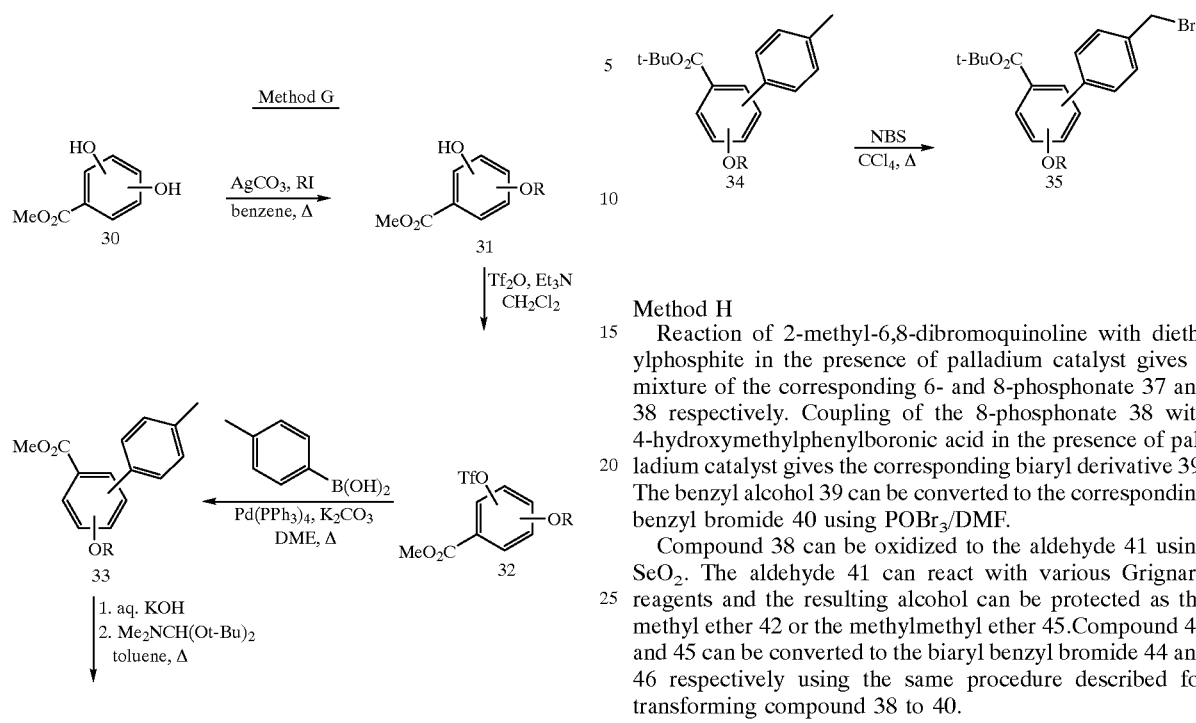

Method H
Reaction of 2-methyl-6,8-dibromoquinoline with diethylphosphite in the presence of palladium catalyst gives a mixture of the corresponding 6- and 8-phosphonate 37 and 38 respectively. Coupling of the 8-phosphonate 38 with 4-hydroxymethylphenylboronic acid in the presence of palladium catalyst gives the corresponding biaryl derivative 39. The benzyl alcohol 39 can be converted to the corresponding benzyl bromide 40 using POBr$_3$/DMF.

Compound 38 can be oxidized to the aldehyde 41 using SeO$_2$. The aldehyde 41 can react with various Grignard reagents and the resulting alcohol can be protected as the methyl ether 42 or the methylmethyl ether 45. Compound 42 and 45 can be converted to the biaryl benzyl bromide 44 and 46 respectively using the same procedure described for transforming compound 38 to 40.

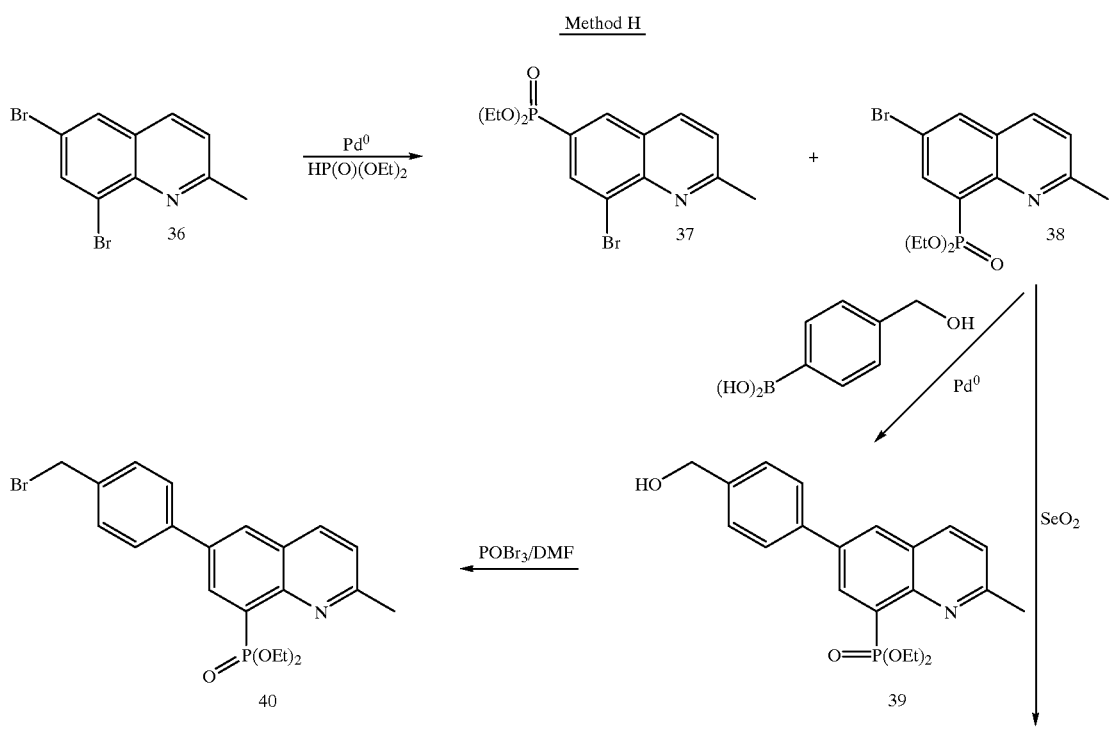

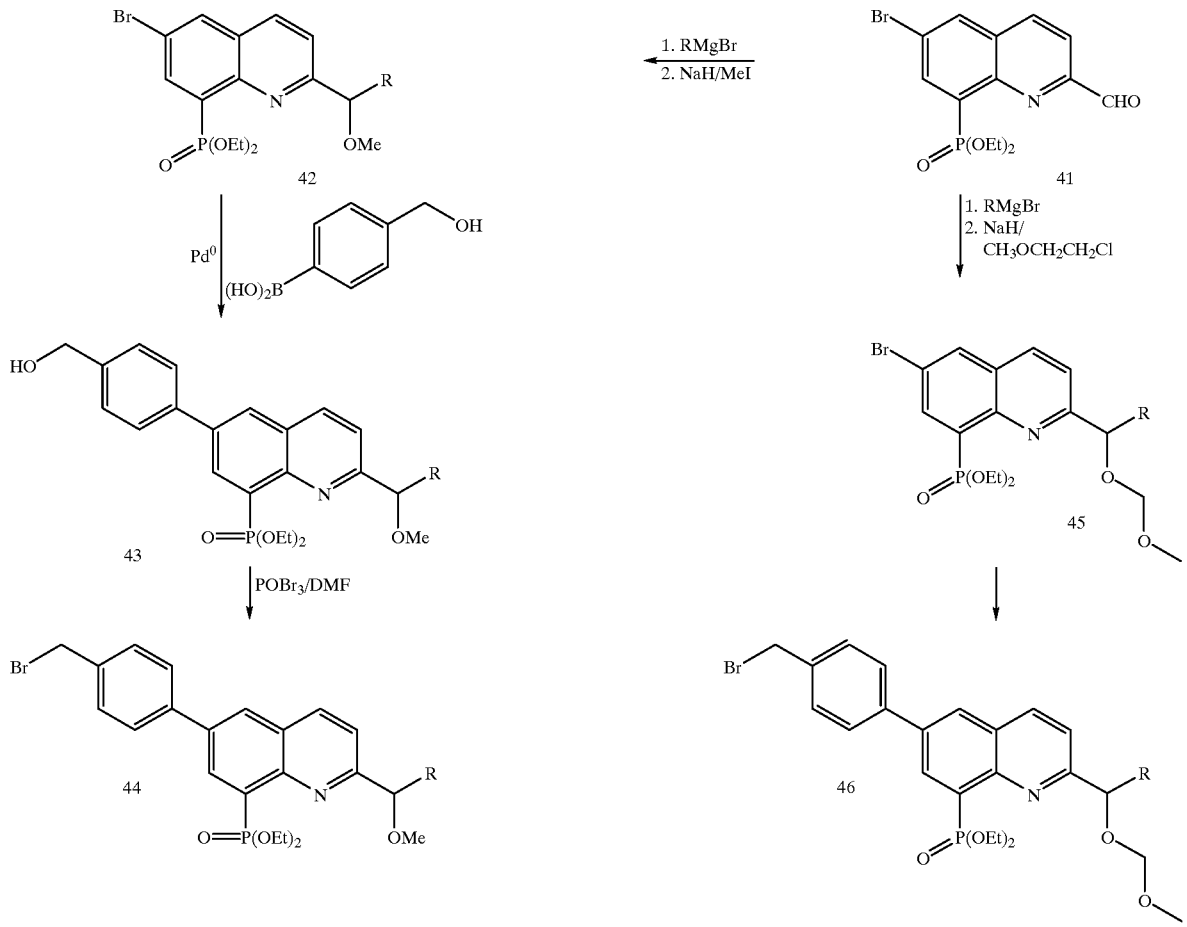
Method I
Bromination of methyl thieno[3,2-b]pyridine-5-carboxylate gives the corresponding 3-bromo derivative 48. Palladium catalyzed coupling of compound 48 with 4-hydroxymethylphenylboronic acid gives the biaryl benzyl alcohol 49 which can be converted to the corresponding bromide 50 using POBr$_3$/DMF.
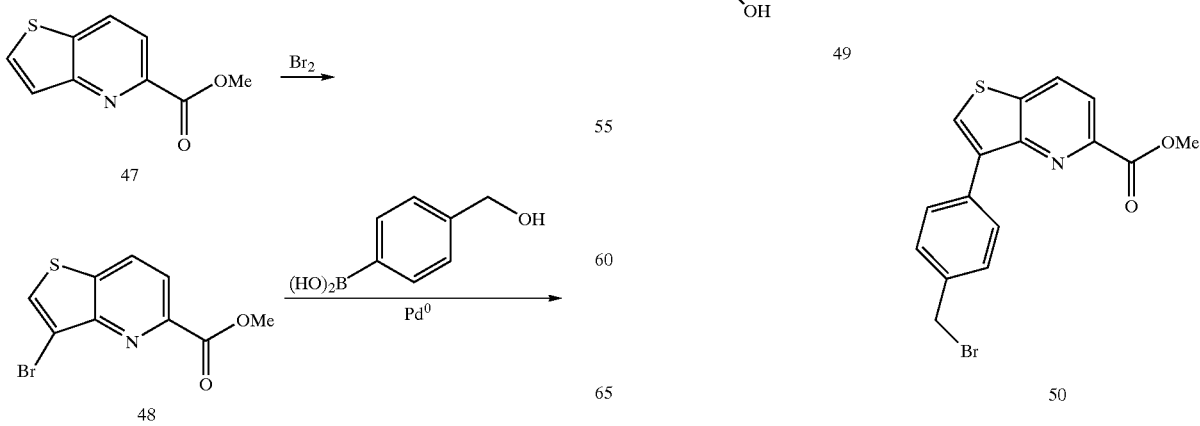

Method J

Palladium catalyzed coupling of 2-methyl-6,8-dibromo quinoline gives predominantly the 6-(hydroxy-methylphenyl)quinoline derivative 52. The benzyl alcohol can be protected as the THP ether 53, which can be alkylated sequentially with various alkyl halides to give the mono- and dialkylated product 54 and 55 respectively. Palladium catalyzed coupling of diethylphosphite with 55 gave 56. Deprotection of the THP ether with HCl/EtOH, followed by bromination of the alcohol with POBr$_3$ gives the bromide 57.

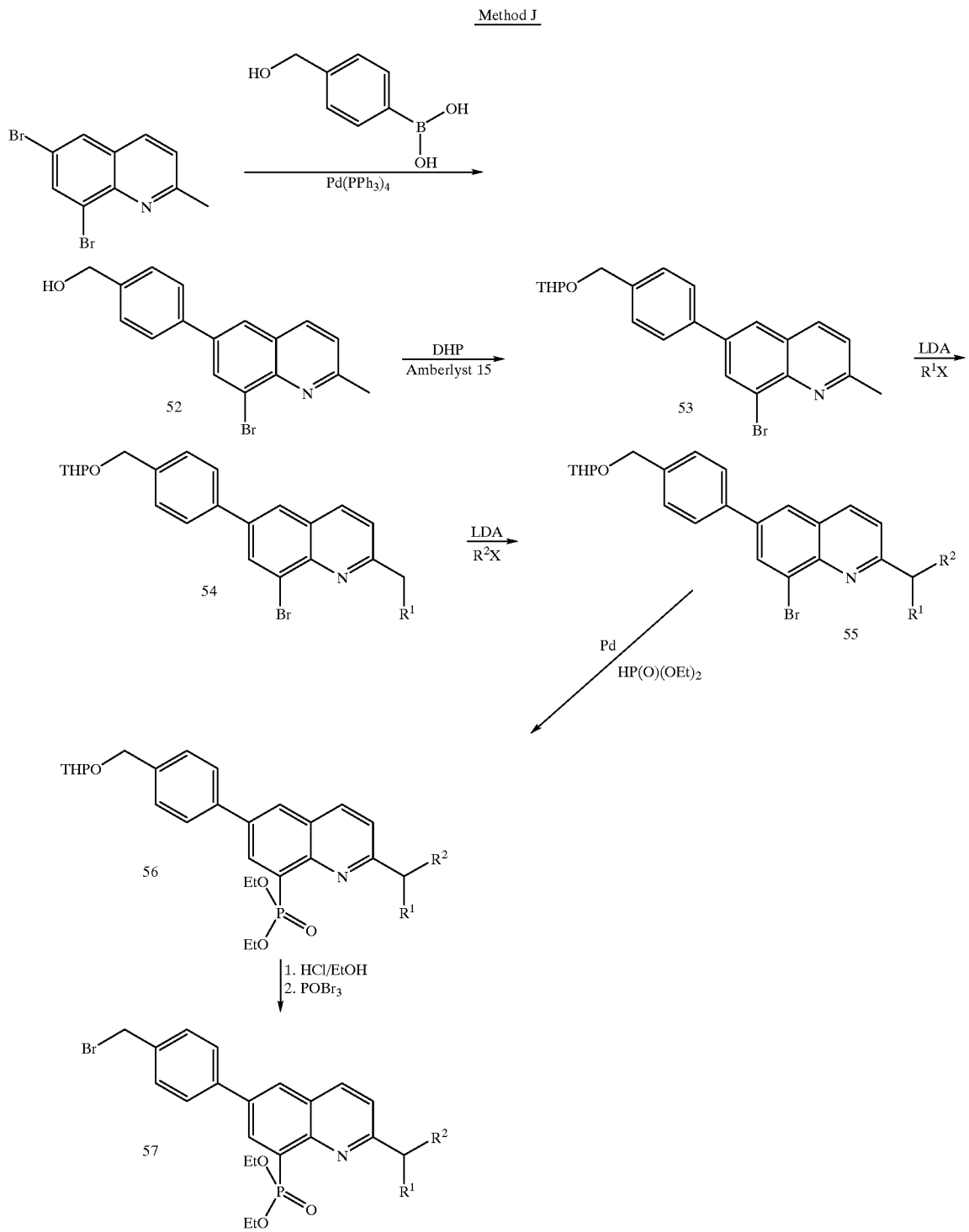

Method K

4'-Methoxy-4-methylbiphenyl 58 is prepared from the Suzuki reaction of 4-methylbenzeneboronic acid and 4-bromoanisole. The methyl ether is then cleaved with a Lewis acid such as BBr$_3$. The hydroxy intermediate is converted to the phosphate intermediate 60 followed Pumanand's condition (Tet. Lett., 1989, 30, 1687). Base promoted rearrangement with a base such as LDA provides the hydroxy phosphonate intermediate 61. Alkylation with an alkyl halide in the presence of a base such as NaOH in a solvent such as DMF gives an alkoxy phosphonate intermediate 62. Bromination with NBS provides the bromomethyl intermediate 63 for subsequent alkylation reaction.

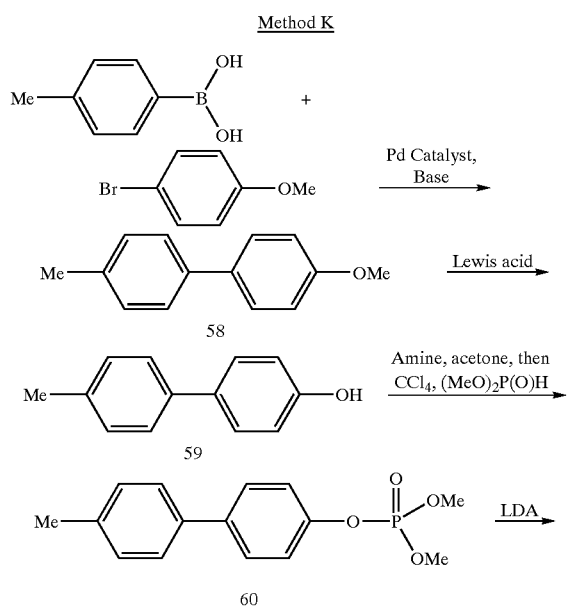

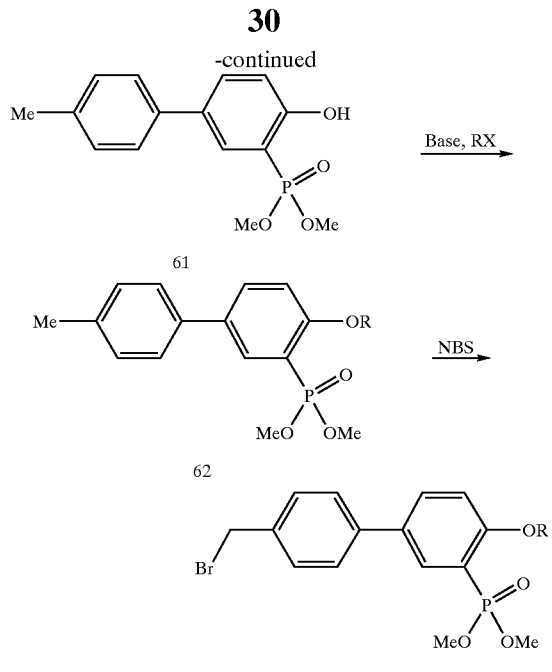

Method L

The compound 66 can be obtained by the reaction of the thiolate generated in situ from the thiosilane 64, with an appropriate electrophile. The resulting intermediate 65 is then converted to the free phosphonic acid by treatment with a reagent such as TMSiBr.

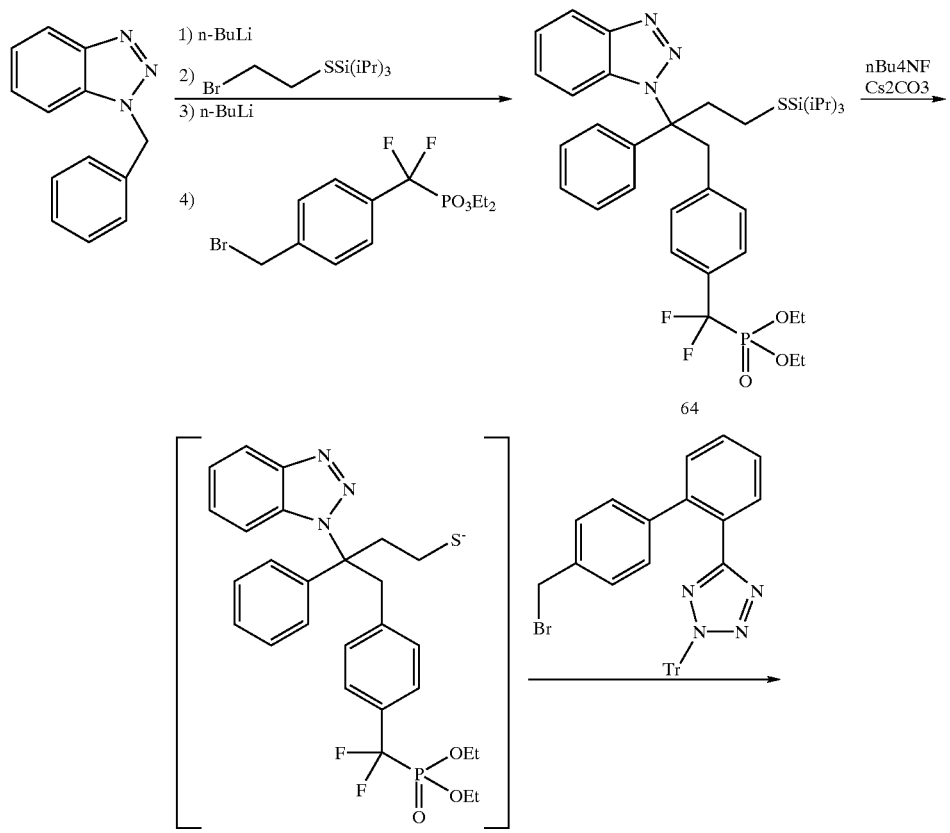

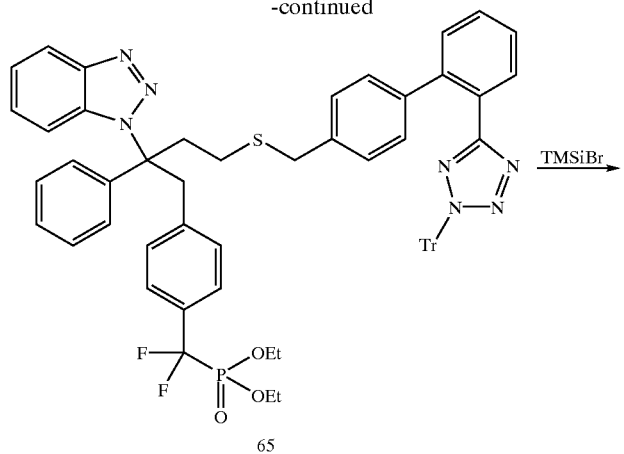

65

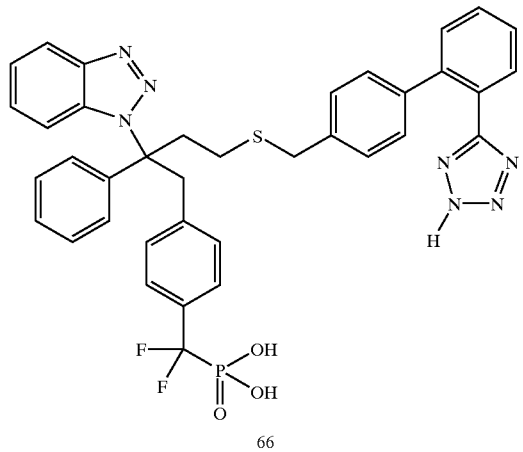

66

Methods M, N and O describe methods of making pro-drugs from phosphonic acids and phosphonic acid salts. In Methods M, N and O, Q is the residue of the molecule that is attached to the —CF$_2$PO$_3$H$_2$ group.

Method M

The disodium phosphonate 67 can be alkylated with a chloroalkyl ester (*Synth. Com.* 25(18) 2739 (1995)) or carbonate (*Antiviral Chemistry & Chemotherapy* 8, 557 (1997)) to give both the mono and diprotected phosphonates (68 and 69) which can be separated by flash chromatography on silica gel.

-continued

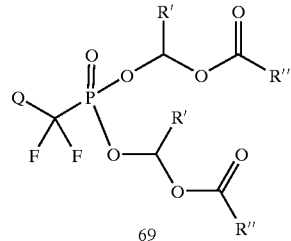

69

Method N

The phosphonic acid 70 can be treated with Cs$_2$CO$_3$ and a chloroalkyl ester or carbonate in CH$_3$CN to give a mixture of mono and diprotected phosphonates which can be separated by flash chromatography on silica gel.

Method M

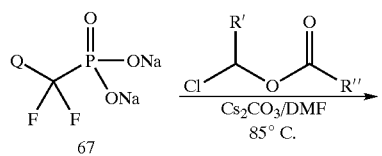

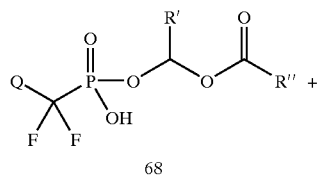

68

Method N

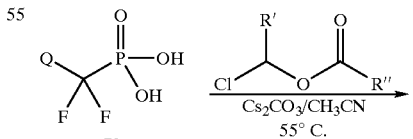

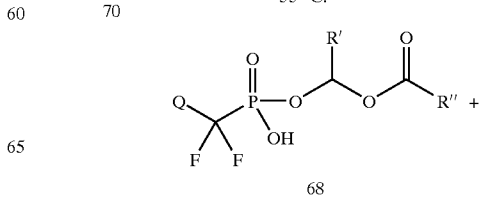

68

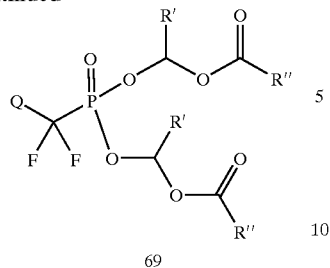
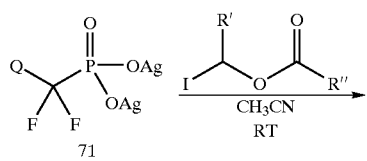
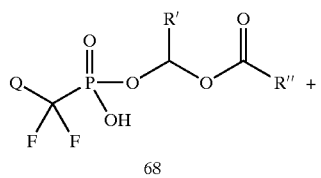
Method O
The phosphonic acid 70 can be treated with silver trifluoroacetate to give the disilver salt 71 which can be treated with an iodoalkyl ester (*Eur. J. Phar. Sci.* 4, 49 (1996)) or carbonate to give a mixture of the mono and diprotected phosphonates which are separable by flash chromatography.
Method O
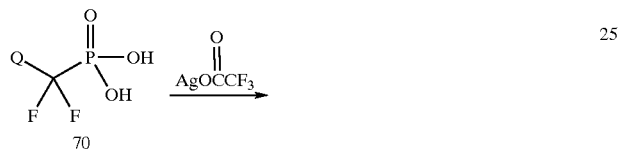
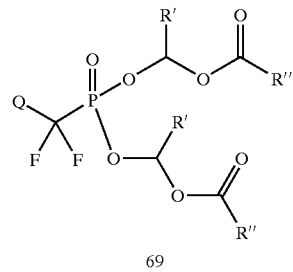
TABLE 1
| | Example | Method |
|---|---|---|
| 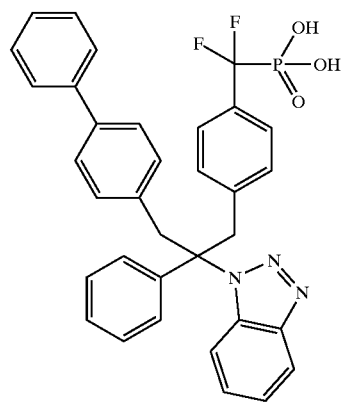 | 1 | A |
| 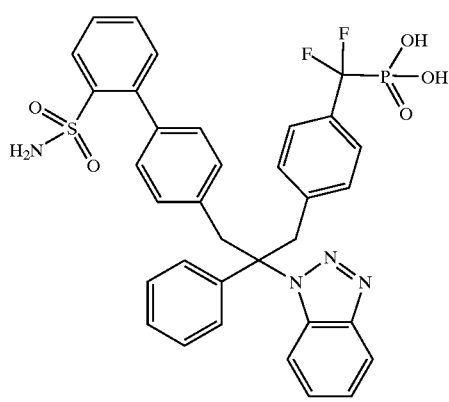 | 2 | A |

TABLE 1-continued

| Structure | Example | Method |
|---|---|---|
| (structure) | 3 | A |
| (structure) | 4 | A + E |
| (structure) | 5 | A + E |
| (structure) | 6 | B |

TABLE 1-continued
| | Example | Method |
|---|---|---|
| 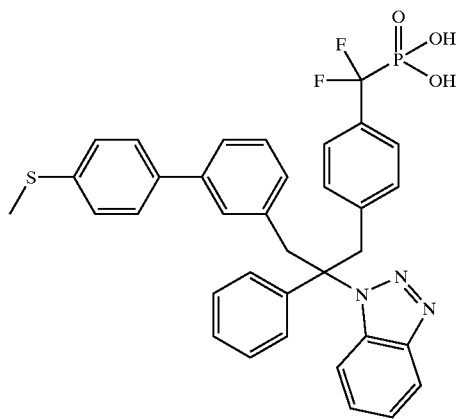 | 7 | B |
| 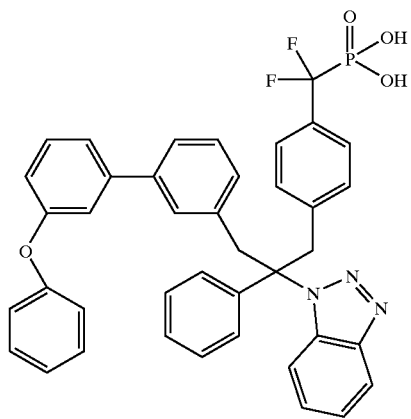 | 8 | B |
| 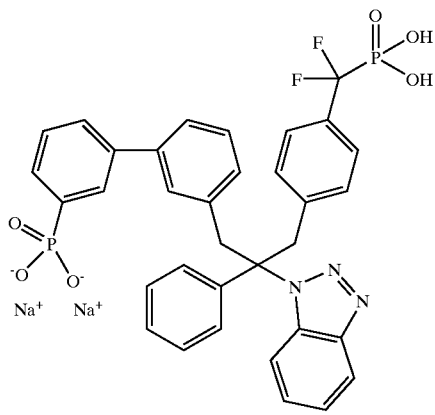 | 9 | A + E |

TABLE 1-continued

| | Example | Method |
|---|---|---|
| [structure] | 10 | D + G |
| [structure] | 11 | D + G |
| [structure] | 12 | D + G |

TABLE 1-continued
| | Example | Method |
|---|---|---|
| 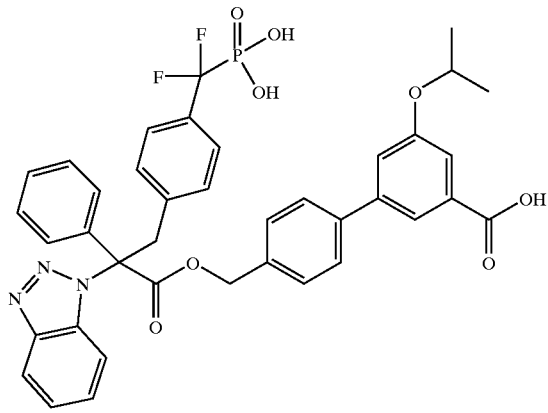 | 13 | D + G |
| 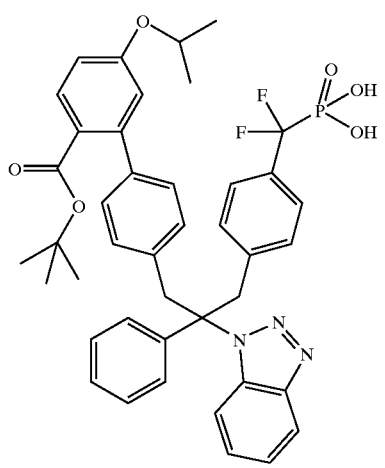 | 14 | A + G |
| 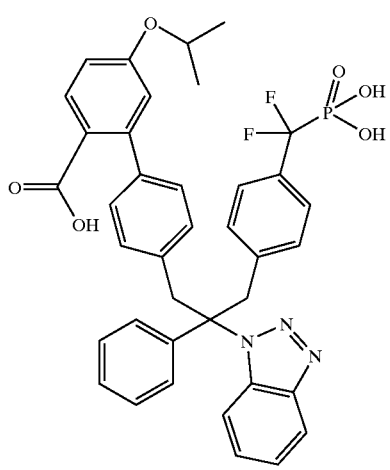 | 15 | A + G |

TABLE 1-continued

| Example | Method |
|---|---|
| 16 | A + G |
| 17 | L |
| 18 | A + H |

TABLE 1-continued
| | Example | Method |
|---|---|---|
| 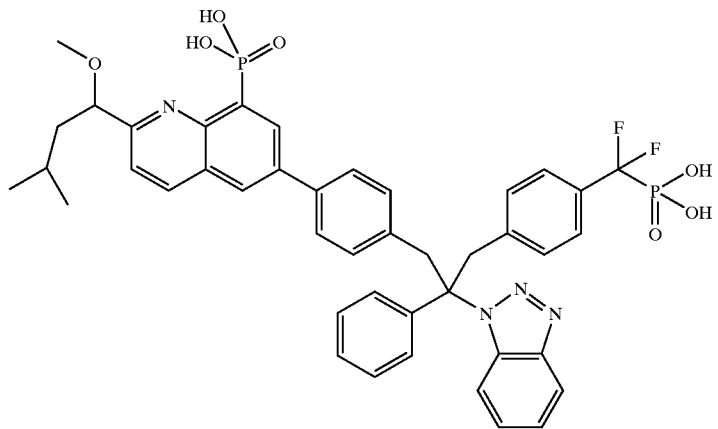 | 19 | A + H |
| 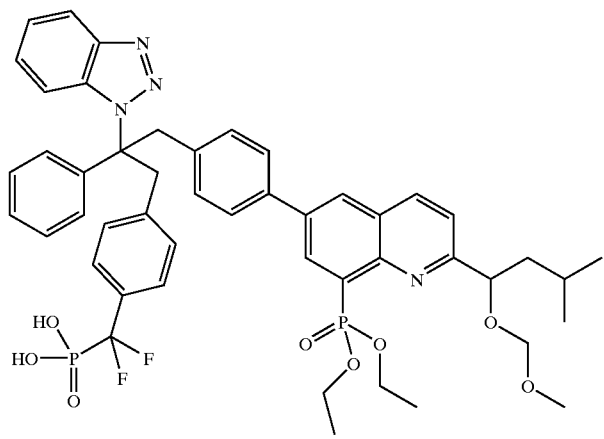 | 20 | A + H |
| 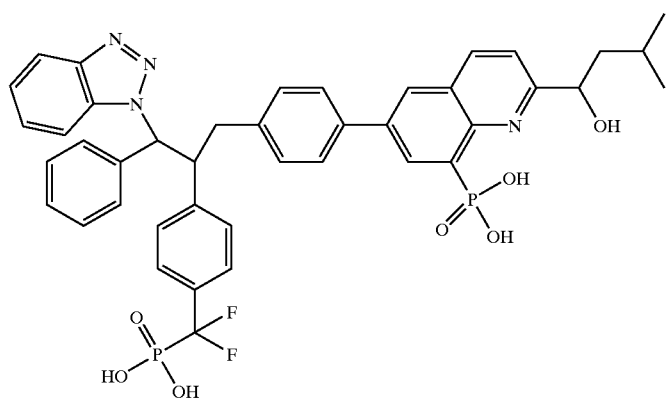 | 21 | A + H |

TABLE 1-continued
| | Example | Method |
|---|---|---|
| 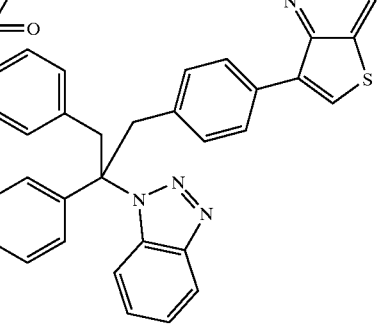 | 22 | A + I |
| 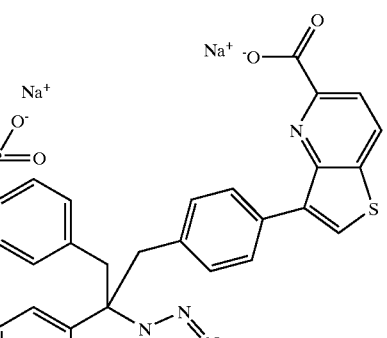 | 23 | A + I |
| 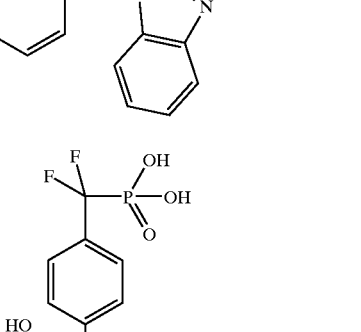 | 24 | C |
| 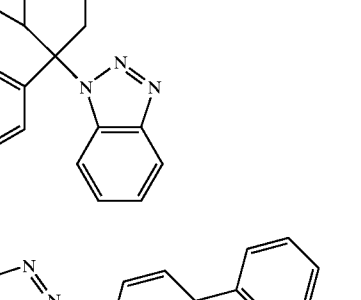 | 25 | A + F |

TABLE 1-continued

| Example | Method |
|---|---|
| 26 | A + K |
| 27 | A + K |

TABLE 2

Other Compounds of the Invention

| Method |
|---|
| A + H |

TABLE 2-continued

Other Compounds of the Invention

| | Method |
|---|---|
| 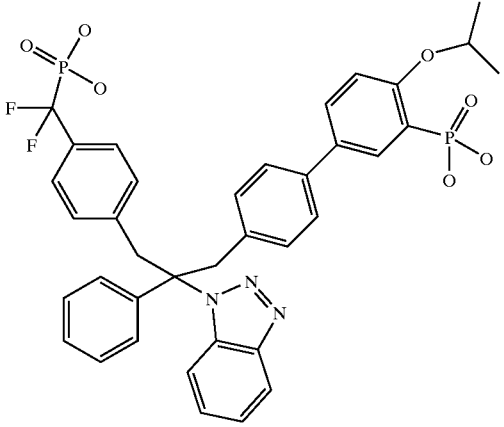 | A + K |

ASSAYS FOR DEMONSTRATING BIOLOGICAL ACTIVITY

Activity in the compounds of this application is demonstrated using the following assays for PTP-1B-inhibiting activity.

Phosphatase Assay Protocol
Materials:
EDTA-ethylenediaminetetraacetic acid (Sigma)
DMH-N,N'-dimethyl-N,N'-bis(mercaptoacetyl)-hydrazine (synthesis published in *J. Org. Chem.* 56, pp. 2332–2337,(1991) by R. Singh and G. M. Whitesides and can be substituted with DTT -dithiothreitol Bistris -2,2-bis (hydroxymethyl)2,2',2"-nitrilotriethanol-(Sigma) Triton X-100-octylphenolpoly(ethylene-glycolether) 10 (Pierce).
Antibody: Anti-glutathione S-transferase rabbit (H and L) fraction (Molecular Probes)
Enzyme: Human recombinant PTP-1B, containing amino acids 1–320, fused to GST enzyme (glutathione S-transferase) or to FLAG peptide purified by affinity chromatography (Huyer et al, 1997, J. Biol. Chem., 272, 843–852). Wild type contains active site cysteine(215), whereas mutant contains active site serine(215).
Tritiated peptide: Bz-NEJJ-CONH$_2$, Mwt. 808, empirical formula, $C_{32}H_{32}T_2O_{12}P_2F_4$

| Stock Solutions | |
|---|---|
| (10×) Assay Buffer | 500 mM Bistris (Sigma), pH 6.2, MW = 209.2 |
| | 20 mM EDTA (GIBCO/BRL) |
| | Store at 4° C. |
| Prepare fresh daily: | |
| Assay Buffer (1×) | 50 mM Bistris |
| (room temp.) | 2 mM EDTA |
| | 5 mM DMH (MW = 208) |
| Enzyme Dilution | |
| Buffer (keep on ice) | 50 mM Bistris |
| | 2 mM EDTA |
| | 5 mM DMH |
| | 20% Glycerol (Sigma) |
| | 0.01 mg/ml Triton X-100 (Pierce) |
| Antibody Dilution | |
| Buffer (keep on ice) | 50 mM Bistris |
| | 2 mM EDTA |

IC$_{50}$ Binding Assay Protocol:
Compounds (ligands) which potentially inhibit the binding of a radioactive ligand to the specific phosphatase are screened in a 96-well plate format as follows:
To each well is added the following solutions @ 25° C. in the following chronological order:

1. 110 µl of assay buffer.
2. 10 µl. of 50 nM tritiated BzN-EJJ-CONH$_2$ in assay buffer (1×) @ 25° C.
3. 10 µl. of testing compound in DMSO at 10 different concentrations in serial dilution (final DMSO, about 5% v/v) in duplicate @ 25° C.
4. 10 µl. of 3.75 µg/ml purified human recombinant GST-PTP-1B in enzyme dilution buffer.
5. The plate is shaken for 2 minutes.
6. 10 µl. of 0.3 µg/ml anti-glutathione S-transferase (anti-GST) rabbit IgG (Molecular Probes) diluted in antibody dilution buffer @ 25° C.
7. The plate is shaken for 2 minutes.
8. 50 µl. of protein A-PVT SPA beads (Amersham) @ 25° C.
9. The plate is shaken for 5 minutes. The binding signal is quantified on a Microbeta 96-well plate counter.
10. The non-specific signal is defined as the enzyme-ligand binding in the absence of anti-GST antibody.
11. 100% binding activity is defined as the enzyme-ligand binding in the presence of anti-GST antibody, but in the absence of the testing ligands with the non-specific binding subtracted.
12. Percentage of inhibition is calculated accordingly.
13. IC$_{50}$ value is approximated from the non-linear regression fit with the 4-parameter/multiple sites equation (described in: "Robust Statistics", New York, Wiley, by P. J. Huber (1981) and reported in nM units.

14. Test ligands (compounds) with larger than 90% inhibition at 10 $\mu$M are defined as actives.

Enzyme Assay PTP-1B

Assay buffer 50 mM Bis-Tris (pH=6.3)

2 mM EDTA 5 mM N,N'-dimethyl-N,N'-bis(mercaptoacetyl)hydrazine (DMH)

Substrate 10 mM fluorescein diphosphate (FDP) store at −200C

Enzyme dilution buffer 50 mM Bis-Tris (pH=6.3)

2 mM EDTA 5 mM DMH

20%(v/v) glycerol 0.01% Triton X-100

The assay was carried out at room temperature in 96 well plates. The reaction mixture in 170 $\mu$l contained 50 mM Bis-Tris (pH=6.3), 2 mM EDTA, 5 mM N,N'-dimethyl-N, N'bis(mercaptoacetyl)hydrazine (DMH) and 10 $\mu$M fluorescein diphosphare (FDP). 10 $\mu$l of 10 concentrations (serial dilution) of the test compound (inhibitor) dissolved in DMSO or DMSO alone for control was added to each well and the plate was mixed for 2 min. The reaction was initiated by adding 20 $\mu$l of diluted PTP-1B (50 nM in 50 mM Bis/Tris (pH=6.3), 2 mM EDTA, 5 mM DMH, 20% glycerol and 0.01% Triton X-100. The phosphatase activity was followed by monitoring the appearance of the fluorescent product fluorescein monophosphate (FMP) continuously for 15–30 min, using the Cytofluor II plate reader (PerSeptive Biosystems Inc.) with excitation of 440 nm (slit width 20 nm) and emission at 530 nm (slit width 25 nm). All the assays were done at least in duplicate. The initial rate of FMP formation is plotted against the concentration of inhibitor and the data was fitted to 4-parameter equation and the inflection point of the fit is the $IC_{50}$.

Pharmacokinetics in Rats

Per Os Pharmacokinetics in Rats

Procedure:

The animals are housed, fed and cared for according to the Guidelines of the Canadian Council on Animal Care.

Male Sprague Dawley rats (325–375 g) are fasted overnight prior to each PO blood level study.

The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparinized vacutainer tube.

Compounds are prepared as required, in a standard dosing volume of 10 mL/kg, and administered orally by passing a 16 gauge, 3" gavaging needle into the stomach.

Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed.

Typical time points for determination of rat blood levels after PO dosing are:

0, 15 min, 30 min, 1 h, 2 h, 4 h, 6 h

After the 4 hr time point bleed, food is provided to the rats ad libitum. Water is provided at all times during the study.

Vehicles:

The following vehicles may be used in PO rat blood level determinations:

PEG 200/300/400: restricted to 2 mL/kg

Methocel 0.5%–1.0%: 10 mL/kg

Tween 80: 10 mL/kg

Compounds for PO blood levels can be in suspension form. For better dissolution, the solution can be placed in a sonicator for approximately 5 minutes.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv(mg/kg)}{AUCiv}$$

The units of CL are mL/h·kg (milliliters per hour kilogram)

Intravenous Pharmacokinetics in Rats

Procedure:

The animals are housed, fed and cared for according to the Guidelines of the Canadian Council on Animal Care.

Male Sprague Dawley (325–375 g) rats are placed in plastic shoe box cages with a suspended floor, cage top, water bottle and food.

The compound is prepared as required, in a standard dosing volume of 1 mL/kg.

Rats are bled for the zero blood sample and dosed under $CO_2$ sedation. The rats, one at a time, are placed in a primed $CO_2$ chamber and taken out as soon as they have lost their righting reflex. The rat is then placed on a restraining board, a nose cone with $CO_2$ delivery is placed over the muzzle and the rat restrained to the board with elastics. With the use of forceps and scissors, the jugular vein is exposed and the zero sample taken, followed by a measured dose of compound which is injected into the jugular vein. Light digital pressure is applied to the injection site, and the nose cone is removed. The time is noted. This constitutes the zero time point.

The 5 min bleed is taken by nicking a piece (1–2 mm) off the tip of the tail. The tail is then stroked with a firm but gentle motion from the top of the tail to the bottom to milk the blood out of the tail. Approximately 1 mL of blood is collected into a heparinized collection vial. Subsequent bleeds are taken in the same fashion, except that there is no need to nick the tail again. The tail is cleaned with a piece of gauze and bled, as described above, into the appropriate labelled tubes.

Typical time points for determination of rat blood levels after I.V. dosing are either:

0, 5 min, 15 min, 30 min, 1 h, 2 h, 6 h or 0, 5 min, 30 min, 1 h, 2 h, 4 h, 6 h.

Vehicles:

The following vehicles may be used in IV rat blood level determinations:

Dextrose: 1 mL/kg

2-Hydroxypropyl-b-cyclodextrin 1 mL/kg

DMSO (dimethylsulfoxide): Restricted to a dose volume of 0.1 mL per animal

PEG 200: Not more than 60% mixed with 40% sterile water–1 mL/kg

With Dextrose, either sodium bicarbonate or sodium carbonate can be added if the solution is cloudy.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv(\text{mg}/\text{kg})}{AUCiv}$$

The units of CL are mL/h·kg (milliliters per hour kilogram).

PTP 1B Intact Cell Assay

This assay is the subject of copending, commonly assigned U.S. Provisional Application No. 60/123,243, filed Mar. 8, 1999, which patent application is incorporated herein by reference, and was recently published in Cromlish, Wanda A., Paul Payette and Brian P. Kennedy (1999) *Biochem Pharmocol* 58: 1539–1546.

Construction of Recombinant Baculovirus Transfer Vectors and Insect Cells

Briefly, using the Bac-to-Bac Baculovirus Expression System (Gibco-BRL, Mississauga, Ontario, Canada) PTP 1B cDNA (obtained from Dr. R. L. Erikson, Harvard University, USA), is cloned into the pFASTBAC donor plasmid engineered to include a FLAG sequence at the 5' end of the cDNA (PTP1B-FL). The recombinant plasmid is transformed into competent DH10BAC *E. Coli* cells. Following transposition and antibiotic selection, the recombinant bacmid DNA is isolated from selected *E. Coli* colonies and used to transfect sf9 insect cells (Invitrogen, San Diego, Calif., U.S.A.). The sf9 cells are cultured in spinner flasks at 28° C. in Graces supplemented medium (Gibco-BRL, Mississauga, Ontario, Canada) with 10% heat-inactivated fetal bovine serum (Gibco-BRL) following the protocol of Summers and Smith (*A manual for Methods for Baculovirus Vectors and Insect Culture Procedures(Bulletin No. 1555). Texas A & M University, Texas Agricultural Experiment Station, College Station, Tex., 1987*).

Intact Cell Assay

Infected sf9 cells expressing PTP1B-FL and mock infected cells, are harvested at 29 hpi (hours post infection) by gentle centrifugation (Beckman GS-6R) at 460 rpm, (48 g) for 5 min. Cells are washed once in assay buffer (Hanks' solution buffered with 15 mM Hepes, pH 7.4, obtained from Sigma, St. Louis, Mo., U.S.A.) and recentrifuged at 300 rpm (21 g) for 10 min. The cells are then gently resuspended in assay buffer and examined using a hemacytometer for cell density and viability by trypan blue exclusion. Assays are performed using a Tomtec Quadra 96 pipeting robot, programmed to mix the cells gently after each addition. In 200 μL of assay buffer, $2 \times 10^5$ PTP expressing cells or mock infected cells are dispensed into each well of 96-well polypropylene plates and pre-incubated either with a test compound or DMSO vehicle (3 μL), for 15 min at 37° C. The pre-incubated cells are challenged with a final concentration of 10 mM pNPP (p-nitrophenyl phosphate, obtained from Sigma-Aldrich Canada Ltd., Oakville, Ontario) for 15 min, centrifuged at 4° C. and the amount of substrate hydrolysis is determined spectrophotometerically at $OD_{405}$.

Oral Glucose Tolerance Test

Oral glucose tolerance tests are done on conscious Zucker obese fa/fa rats or obese ob/ob mice (age 12 weeks or older). The animals are fasted for 16–18 hours before use for experiments. A test compound or a vehicle is given either intraperitoneally or orally 60 minutes before oral administration of a glucose solution at a dose of 2 g/kg body weight. Blood glucose levels are measured using a Medisense glucometer from tail bled samples taken at different time points before and after administration of glucose. A time curve of the blood glucose levels is generated and the area-under-the-curve (AUC) for 120 minutes is calculated (the time of glucose administration being time zero). Percent inhibition is determined using the AUC in the vehicle-control group as zero percent inhibition.

In separate studies, C57BL/6J mice are fed a high fat (35%) and high carbohydrate (36%) diet obtained from Bioserv (Frenchtown, N.J.) for 3 to 4 weeks, at which time the mice gained 50–100% of the baseline body weight. Oral glucose tolerance tests are done in the same manner as described above.

EXAMPLES

The invention is further illustrated by the following non-limiting examples in which, unless stated otherwise:

(i) all operations were carried out at room or ambient temperature, that is, at a temperature in the range 18–25° C., (ii) evaporation of solvent was carried out using a rotary evaporator under reduced pressure (600–4000 pascals: 4.5–30 mm. Hg) with a bath temperature of up to 60° C., (iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (litre(s)), mL (millilitres), g (gram(s)), mg (milligrams(s)), mol (moles), mmol (millimoles), eq (equivalent(s)).

Example 1

{[4-(2-Benzotriazol-1-yl-3-biphenyl-4-yl-2-phenyl-propyl)-phenyl]-difluoro-methyl}-phosphonic Acid Step 1-benzyl-1H-benzotriazole To a solution of benzotriazole (1.2 g, 10.1 mmol) in DMF (40 mL) at r.t. was added a solution of 1M t-BuOK in THF (11 mL, 11 mmol). After stirring for 30 min., benzyl bromide (2.0 g, 11.6 mmol) was added. The mixture was further stirred for 1 h, diluted with $H_2O$, extracted with EtOAc. The EtOAc extract was washed with $H_2O$ (3×), dried ($MgSO_4$) and concentrated. The residue was swished with hexanes containing small amount of Et2O to give 1.2 g (57%) of title compound as white powders.

$^1$H NMR (Acetone-$d_6$) δ 5.96 (s, 2H), 7.42–7.25 (6H), 7.48 (m, 1H), 7.72 (d, 1H), 8.00 (d, 1H).

Step 2: [4-(2-benzotriazol-1-yl-2-phenylethyl)phenyl] difluoromethylphosphonic Acid di-tert-butyl Ester.

To a solution of 1-benzyl-1H-benzotriazole (820 mg, 3 mmol) in THF (50 mL) at −78° C. was added a solution of 2.5M n-BuLi in hexanes (1.5 mL, 3.8 mmol). The solution turned deep blue immediately. After stirring for 5 min at −78° C., a solution of (4-bromomethylphenyl) difluoromethylphosphonic acid di-tert-butyl ester (1.4 g, 3.4 mmol) in THF (4 mL) was added. The deep blue color disappeared. The mixture was then stirred at −78° C. for 1 h, quenched with $H_2O$ and extracted with EtOAc. The EtOAc extract was washed with brine, dried ($Na_2SO_4$) and concentrated. The residue was swished with $Et_2O$ to give 1.77 g (84%) of the title compound as a white solid.

$^1$H NMR (Acetone-$d_6$) δ 1.28 (s, 9H), 1.30 (s, 9H), 3.86 (dd, 1H), 4.21 (dd, 1H), 6.44 (dd, 1H), 7.42–7.25 (m, 9H), 7.54 (d, 2H), 7.74 (d, 1H), 7.92 (d, 1H).

Step 3: [4-(2-benzotriazol-t-yl-3-biphenyl-4-yl-2-phenyl-propyl)-phenyl]-difluoro-methyl}-phosphonic Acid di-tert-butyl Easter To a solution of the product obtained from step 2 (54 mg, 0.1 mmol) in THF (1.2 mL) at −78° C. was added a solution of 2.5M n-BuLi in hexanes (0.05 mL, 0.12 mmol). The solution turned deep blue immediately. After stirring for 5 min at −78° C., a solution of 4-phenylbezyl chloride (0.12 mmol, 24.2 mg) in TF (0.3 mL) was added. The deep blue color disappeared. The mixture was then stirred at −78° C. for 0.25 h, quenched with $H_2O$ and extracted with EtOAc. The EtOAc extract was washed with brine, dried ($MgSO_4$) and concentrated. The residue was chromatographed on silica gel (eluted with 40%EtOAc/hexane) to give 40 mg (57%) of the title comnpound.

Step 4: {[4-(2-benzotriazol-1-yl-3-biphenyl-4-yl-2-phenyl-propyl)-phenyl]-difluoro-methyl 1-phosphonic Acid To a solution of the product obtained from Step 3 (40 mg, 0.056 mmol) in HOAc (1 mL) was added $H_2O$ (0.15 mL). The mixture was stirred at r.t. for 20 h. The solvent was evaporated to give 33 mg (100%) of the title compound.

$^1$H NMR (Acetone-$d_6$) δ 4.05 (m, 2H), 4.16 (m, 2H), 6.75 (m, 5H), 7.13 (m, 2H), 7.34 (m, 12 H), 7.56 (d, 2H), 8.01 (m, 1H).

Example 2

({4-[2-Benzotriazol-1-yl-2-phenyl-3-(2'-sulfamoyl-biphenyl-4-yl)-propyll-phenyl}-difluoro-methyl)-phosphonic Acid Step 1: ({4(2-benzotriazol-1-yl-3-(2'-tert-butylsulfamoyl-biphenyl-4-yl)-2-phenyl-propyll-phenyll-difluoro-methyl)-phosphonic Acid di-tert-butyl Ester To a solution of [4-(2-benzotriazol-1-yl-2-phenylethyl)phenyl]difluoromethylphosphonic acid di-tert-butyl ester (108 mg, 0.2 mmol) in THF (2 mL) at −78° C. was added a solution of 2.5M n-BuLi in hexanes (0.08 mL, 0.22 mmol). The solution turned deep blue immediately. After stirring for 5 min at −78° C., a solution of 4'-bromomethyl-biphenyl-2-sulfonic acid tert-butylamide (Naylor et al. *Bioorganic and Medicinal Chemistry Letters* 1994, 4, 69–74.) (84 mg, 0.22 mmol) in THE (0.5 mL) was added. Before the addition of all the bromide was completed, the color of the anion disappeared. Another 0.22 mmol of BuLi was added. Reaction was completed after addition of both reagents was completed. Aqueous $NH_4Cl$ was added and the mixture was extracted with EtOAc. The EtOAc extract was washed with brine, dried ($MgSO_4$) and concentrated. The residue was chromatographed on silica gel (eluted with 30% acetone/toluene) to give 80 mg (47%) of the title comnpound.

Step 2: ({}4-[2-benzotriazol-1-yl-2-phenyl-3-(2'-sulfamoyl-biphenyl-4-yl)-propyl]-phenyl}-difluoro-methyl)-phosphonic Acid To the product of step 1 (80 mg, 0.094 mmol) was added TFA (1 mL). The mixture was stirred at r.t for 20 h. TFA was removed under vaccum and the residue was coevapoarated twice with $CHCl_3$ to give 50 mg (82%) of the title compound.

$^1$H NMR (Acetone-$d_6$) 67 4.00 (q, 2H), 4.19 (q, 2H), 5.62 (bs, 1H), 6.78 (m, 5H), 7.14 (m, 4H), 7.33 (m, 8H), 7.52 (t, 1H), 7.60 (t, 1H), 7.98 (d, 1H), 8.06 (d, 1H).

Example 3

[(4-{2-Benzotriazol-1-yl-2-phenyl-3-[2'-(1H-tetrazol-5-yl)-biphenyl-4-yl]-propyl }-phenyl)-difluoro-methyl]-phosphonic Acid Step 1: [(4-{2-benzotriazol-1-yl-2-phenyl-3-[2'-(1-triphenylmethyl-(1H-tetrazol-5-yl)-biphenyl-4-yl]-propyl}-phenyl)-difluoro-methyl]-phosphonic Acid di-tert-butyl Ester To a solution of [4-(2-benzotriazol-1-yl-2-phenylethyl) phenyl]difluoromethylphosphonic acid di-tert-butyl ester (108 mg, 0.2 mmol) in THF (2 mL) at −78° C. was added a solution of 2.5M n-BuLi in hexanes (0.08 mL, 0.22 mmol). The solution turned deep blue immediately. After stirring for 5 min at −78° C., a solution of 2'-(3-triphenylmethyl-1H-tetrazol-5-yl)-biphenyl-4-methyl bromide(123 mg, 0.22 mmol; U.S. Pat. No. 5,412,102) in THP (0.5 mL) was added. The mixture was stirred at r.t. for 0.25 h. Aqueous $NH_4Cl$ was added and the mixture was extracted with EtOAc. The EtOAc extract was washed with brine, dried ($MgSO_4$) and concentrated. The residue was chromatographed on silica gel (eluted with 30% acetoneltoluene) to give 130 mg (72%) of the title comnpound.

Step 2: [(4-{2-benzotriazol-1-yl-2-phenyl-3-[2'-(1H-tetrazol-5-yl)-biphenyl-4-yl]-propyl}-phenyl)-difluoro-methyl]-phosphonic Acid To the product of step 1 (130 mg, 0.14 mmol) was added TFA (1.5 mL). The mixture was stirred at r.t. for 20 h. Evaporation of the TFA gave a solid which is the corrresponding phosphonic acid with the tetrazole still protected. Deprotection of the triazole was achieved by treating the compound with 6 N HCl (1 mL) in THF (2 mL) for 20 h. Evaporation of the solvent gave a solid which was swished to give only 13 mg of the title compound after filtration.

$^1$H NMR (Acetone-$d_6$) δ 4.00 (m, 4H), 6.55 d, 2H), 6.65 (d, 2H), 6.75 (d, 1H), 6.83 (d, 2H), 7.09 (d, 2H), 7.35 (m, 7H), 7.49 (in, 1H), 7.55 (m, 1H), 7.65 (M, 2H), 8.08 (d, 1H).

Example 4

(4'-{2-Benzotriazol-1-yl-3-[4-(difluoro-phosphono-methyl)-phenyl]-2-phenyl-propyl}-biphenyl-3-yl)-phosphonic Acid Diethyl Ester Step 1: diethyl 3-iodophenylphosphonate The title compound was prepared as described by T. Hirad et al in *Synthesis* 1981, p. 56 using 1,3-diodobenzene.

Step 2: (4'-hydroxymethyl-biphenyl-3-yl)-phosphonic Acid Diethyl Ester

To the product of Step 1 (680 mg, 2 mmol) in toluene (10 mL)—H$_2$O (3 mL)—n Propanol (3 mL) were added 4-hydroxymethyl phenyl boronic acid (607 mg, 4 mmol), tris(dibenzylidene acetone)dipalladium (92 mg, 0.1 mmol), triphenylphosphine (209 mg, 0.8 mmol) and EtNH (175 mg, 2.4 mmol). After a period of 18 h at 90° C., the reaction mixture was partionned between EtOAc and H$_2$O. The organic phase was separated, dried over NaSO$_4$, filtered and evaporated under reduced pressure. The title compound was obtained after flash chromatography (446 mg, 69%).

Step 3 (4'-chloromethyl-biphenyl-3-yl)-phosphonic Acid Diethyl Ester

To a solution of the product of step 2 (419 mg, 1.3 mmol) in CHCl$_3$ (1 mL) was added a solution of POCL$_3$ in DMF (0.39 mL, 3.6 mM) at 0° C. The mixture was stirred at 0° C. for 1.5 h. The reaction mixture was partionned between EtOAc and H$_2$O. The organic phase was separated, dried over NaSO$_4$, filtered and evaporated under reduced pressure. The title compound was obtained after flash chromatography (338 mg, 77%). Step 4: [4'-(2-benzotriazol-1-yl-3-4-[(di-tert-butoxy-phosphoryl)-difluoro-methyl]-phenyl}-2-phenyl-propyl)-biphenyl-3-yl]-phosphonic Acid Diethyl Ester To a solution of [4-(2-benzotriazol-1-yl-2-phenylethyl) phenyl]difluoromethylphosphonic acid di-tert-butyl ester (270 mg, 0.5 mmol) in THF (5 mL) at −78° C. was added a solution of 2.5M n-BuLi in hexanes (0.22 mL, 0.55 mmol). The solution turned deep blue immediately. After stirring for 5 min at −78° C., a solution of the product of step 3 (185 mg, 0.55 mmol) in THF (0.5 mL) was added. The mixture was stirred at −78° C. for 0.25 h, quenched with aqueous NH$_4$Cl and extracted with EtOAc. The EtOAc extract was washed with brine, dried (MgSO$_4$) and concentrated under reduced pressure. The title compound was obtained after flash chromatography (300 mg, 71%). Step 5: 4'-{2-benzotriazol-1-yl-3-[4-(difluoro-phosphono-methyl)-phenyl]-2-phenyl-propyl}-biphenyl-3-yl)-phosphonic acid diethyl ester To a solution of the product of Step 4 (80 mg, 0.095 mmol) in HOAc (1 mL) was added H$_2$O (0.1 mL). The mixture was stirred at r.t. for 20 h. Evaporation of the solvent gave the tiltle compound (100%).

$^1$H NMR (Acetone-d$_6$) δ 4.00 (m, 8H), 6.76 (m, 5H), 7.13 (d, 2H), 7.35 (m, 9H), 7.58 (m, 1H), 7.71 (q, 1H), 7.80 (d, 1H), 7.94 (d, 1H), 8.02 (d, 1H).

Example 5

(4'-{2-Benzotriazol-1-yl-3-f4-(difluoro-phosphono-methyl)-phenyl]-2-phenyl-propyl)-biphenyl-3-yl)-phosphonic Acid To a solution of the product of step 4 (EXAMPLE 4) (84 mg, 0.1 mmol) in CHCl$_3$ (2 mL) was added TMSBr (153 mg, 1 mmol). The mixture was heated to 70° C. for 2 h. TMSBr was removed under reduced pressure. The residue was coevaporated with CHCl$_3$ twice. EtOH (1 mL) was added and the mixture was stirred at r.t. for 0.5 h. Evaporation of the EtOH gave 40 mg of the tiltle comnpound.

$^1$H NMR (DMSO-d$_6$) δ 3.90 (t, 2H), 4.05 (q, 2H), 6.68 (m, 5H), 7.08 (d, 2H), 7.20 (d, 2H), 7.35 (7H), 7.49 (m, 1H), 7.60 (q, 1H), 7.70 (d, 1H), 7.80 (d, 1H), 8.09 (d, 1H).

Example 6

({4-[2-Benzotriazol-1-yl-3-(4'-methylsulfanyl-biphenyl-4-yl)-2-phenyl-propyl]-phenyl}-difluoro-methyl)-phosphonic Acid Step 1: ({4-[2-benzotriazol-1-yl-3-(4-bromophenyl)-2-phenyl-propyl]-phenyl}-difluoro-methyl)-phosphonic acid di-tert-butyl ester To a solution of [4-(2-benzotriazol-1-yl-2-phenylethyl) phenyl]difluoromethylphosphonic acid di-tert-butyl ester (1 mmol, 541 mg) in THF (10 mL) at −78° C. was added a solution of 2.5M n-BuLi in hexanes (1.1 mL, 0.44 mmol). The solution turned deep blue immediately. After stirring for 5 min at −78° C., a solution of 4-bromobenzyl chloride (274 mg, 1.1 mmol) was added. The mixture was stirred at −78° C. for 0.25 h, quenched with aqueous NH$_4$Cl and extracted with EtOAc. The EtOAc extract was washed with brine, dried (MgSO$_4$) and concentrated under reduced pressure. The title compound was obtained after flash chromatography (633 mg, 91%).

Step 2: ({4-[2-benzotriazol-1-yl-3-(4'-methylsulfanyl-biphenyl-4-yl)-2-phenyl-propyll-phenyl}-difluoro-methyl)-phosphonic acid di-tert-butyl ester To a solution of the product of step 1 (104 mg, 0.15 mmol) in toluene (5 mL) were added 4-methylsulfanylphenylboronic acid (50.4 mg, 0.3 mmol), tris(dibenzylidene acetone)dipalladium (7 mg, 0.0075 mmol), triphenylphosphine (15.7 mg, 0.06 mmol) and K$_2$CO$_3$ (41 mg, 0.3 mmol). The mixture was purged with N$_2$ and heated to 80° C. for 4 h. Aqueous NH$_4$Cl was added and the mixture was extracted with EtOAc. The EtOAc extract was washed with brine, dried (MgSO$_4$) and concentrated. The residue was chromatographed to give 41 mg of the tiltle compound.

Step 3: ({4-[2-benzotriazol-1-yl-3-(4'-methylsulfanyl-biphenyl-4-yl)-2-phenyl-propyl]-phenyl}-difluoro-methyl)-phosphonic Acid To a solution of the product of Step 2 (41 mg) in HOAc (1 mL) was added H$_2$O (0.1 mL). The mixture was stirred at r.t. for 20 h. Evaporation of the solvent gave the tiltle compound (100%).

$^1$H NMR (Acetone-d$_6$) δ 3.98 (dd, 2H), 4.10 (dd, 2H), 6.72 (d, 2H), 6.75 (m, 3H), 7.14 (d, 2H), 7.35 (m, 11H), 7.52 (d, 2H), 8.00 (d, 1H).

Example 7

(4-{2-(1H-1,2,3-benzotriazol-1-yl)-3-[4'(methylsulfanyl) (1,1'-biphenyl]-3-yl]-2-phenylpropyl}phenyl)(difluoro) methylphosphonic Acid Step 1 di(tert-butyl) {4-[2-(1H-1,2,3-benzotriazol-1-yl)-3-(3-bromophenyl)-2-phenylpropyllphenyl}(difluoro) methylphosphonate To a TBF (1.0 mL) solution of di(tert-butyl) {4-[2-(1H-1,2,3-benzotriazol-1-yl)-2-phenylethyl]phenyl}(difluoro) methylphosphonate (0.100 g, 0.184 mmol) at −78° C. were added nBuLi 1.6 M in Hexane (0.138 mL) and a solution of 3-bromobenzyl bromide (0.046 g, 0.185 mmol) in THF (0.100 mL). After a period of 10 min, aqueous NH$_4$OAc was added to the reaction mixture. The resulting mixture was extracted with ethyl acetate, dried over Na$_2$SO$_4$, filtered and evaporated under reduced pressure. The title compound was obtained after purification by flash chromatography to provide 0.10 g of material.

Step 2 di(tert-butyl) (4-{2-(1H-1,2,3-benzotriazol-1-yl)-3-[4'-(methylsulfanyl)[1,1'-biphenyl]-3-yl]-2-phenylpropyl}phenyl) (difluoro)methylphosphonate To compound (0.050 g, 0.072 mmol) of Step 1 in toluene (1.5 mL) were added 4-methylthiophenyl boronic acid (0.024 g, 0.142 mmol), K$_2$CO$_3$ (0.020 g), Pd(Ph$_3$P)$_4$ (0.010 g). The resulting mixture was heated at 80° C. under nitrogen. After a period of 3 h, the reaction mixture was partitioned between ethyl acetate and water. The organic phase was separated, dried over $Na_2SO_4$, filtered and evaporated. The title compound was obtained after purification by flash chromatography (0.015 g).

Step 3 (4-{2-(1H-1,2,3-benzotriazol-1-yl)-3-[4'-(methylsulfanyl)(1,1'-biphenyl]-3-yl}-2-phenylpropyl]phenyl)(difluoro) methylphosphonic Acid The compound of Step 2 was dissolved in $HOAc-H_2O$ (9/1). After a period of 18 h, the solvents were evaporated to give the title compound.

$^1$H NMR (400 MHz, $CD_3COCD_3$) δ 2.50 (3H, s), 4.05 (4H, m), 6.5–7.5 (20H, m).

Example 8
{4-[2-(1H-1,2,3-benzotriazol-1-yl)-3-(3'phenoxy(1,1'-biphenyl]-3-yl)-2-phenylpropyl)phenyl}(difluoro) methylphosphonic acid.

Step 1 di(tert-butyl) {4-12-(1H-1,2,3-benzotriazol-1-yl)-3-(3'-phenoxy[1,1'-biphenyl]-3-yl)-2-phenylpropyl]phenyl}(difluoro)methylphosphonate To the compound of Example 7 Step 1 (0.050 g, 0.072 mmol) in toluene (1.5 mL) were added $Pd(Ph_3)_4$ (0.010 g), $K_2CO_3$ (0.020 g) and 3-(dihydroxyboryl)-3'-phenoxy-1,1'-biphenyl (0.031 g, 0.144 mmol). The resulting mixture was heated at 80° C. under nitrogen, after a period of 3 h, the reaction mixture was partitioned between ethyl acetate and water. The organic phase was separated, dried over $Na_2SO_4$, filtered and evaporated. The title compound was obtained after purification by flash chromatography.

Step {4-[2-(1H-1,2,3-benzotriazol-1-yl)-3-(3'-phenoxy(1,1'-biphenyl]-3-yl)-2-phenylpropyl]phenyl}(difluoro) methylphosphonic acid The compound of Step 1 was treated with excess of TFA in $CH_2Cl_2$. After evaporation under reduced pressure the title compound was obtained.

$^1$H NMR (400 MHz, $CD_3COCD_3$) δ 4.00 (4H, m), 6.50-8.00 (26H, m).

Example 9
3-(2-(1H-1,2,3-benzotriazol-1-yl)-3-(4-[difluoro (phosphono)methyl]phenyl}-2-phenylpropyl)(1,1'-biphenyl)]-3-ylphosphonic Acid Step 1 diethyl 3-iodophenylphosphonate The title compound was prepared as described by T. Hira et al in *Synthesis* 1981, p. 56 using 1,3-diodobenzene.

Step 2: 3-(diethoxyphosphoryl)-3'-methyl-1,1'-biphenyl

To a compound of Step 1 (0.200 g, 0.588 mmol) in toluene (5 mL)—$H_2O$ (1.5 mL)-n-propanol (5 mL) were added 3-methyl phenyl boronic acid (0.158 g, 1.17 mmol), tris (dibenzylidene acetone)dipalladium (0.030 g), triphenylphosphine (0.123 g) and $Et_2NH$ (0.083 mL). After a period of 18 h at 80° C., the reaction mixture was partionned between EtOAc and $H_2O$. The organic phase was separated, dried over $Na_2SO_4$, filtered and evaporated under reduced pressure. The title compound was obtained after flash chromatography (0.122 g).

Step 3: 3-(bromomethyl)-3'-(diethoxyphosphoryl)-1, 1'biphenyl

To the compound of Step 2 (0.122 g, 0.400 mmol) in $CCl_4$ (5 mL) were added NBS (0.050 g, 0.480 mle) and a catalytic amount of benzoyl peroxide. The reaction mixture was refluxed under light for 2 h. The reaction was cooled to room temperature, filtered and evaporated. The title compound was obtained after purification by flash chromatography. (0.150 g).

Step 4: diethyl 3'-(2-(1H-1,2,3-benzotriazol-1-yl)-3-{4-r[di (tert-butoxy)phosphoryl](difluoro)methyl]phenyl}-2-phenylpropyl)[1,1'-biphenyl]-3-ylphosphonate To a solution (2.0 mL) of di(tert-butyl){4-[2-(1H-1,2,3-benzotriazol-1-yl)-2-phenylethyl]phenyl}(difluoro) methylphosphonate (0.211 g, 0.390 mL) were added n-BuLi (0.292 mL, 0.467 mmol) and the bromide of Step 3 (0.150 g, 0.391 mmol). After a period of 10 min, aqueous $NH_4Oac$ was added to the reaction mixture. After extraction with EtOAc the organic phase was dried over $NaSO_4$, filtered and evaporated. The title compound was obtained after flash chromatography (0.030 g)

Step 5: 3'-(2-(1H-1,2,3-benzotriazol-1-yl)-3-(4-[difluoro (phosphono) methyl]phenyl}-2-phenylpropyl)(1,1'-biphenyl]-3-ylphosphonic Acid To the compound of Step 4 (0.030 g, 0.035 mmol)in $CHCl_3$ (1.0 mL) was added 0.1 mL of TMSBr. After a period of 2 h at reflux, the reaction mixture was evaporated and co-evaporated with EtOAc. After drying under reduced pressure the title compound was obtained.

$^1$H NMR (400 MHz, $CD_3COCD_3$) δ 3.50 (4H, m), 6.60–8.10 (21H).

Example 10
{4-[2-(1H-1,2,3-benzotriazol-1-yl)-3-[(4-(2-carboxy-5-isopropoxyphenyl) benzyl)oxy]-3-oxo-2-phenylpropyl] phenyl}(difluoro)methylphosphonic Acid Step 1: Methyl 2-hydroxy-4-isopropoxybenzoate To a solution of methyl 2,4-dihydroxybenzoate (5.4 g) and 2-iodopropane (10.2 g) in benzene (200 mL) was added $Ag2CO3$ and the mixture was heated in a 100° C. oil bath for 1 h. Additional methyl 2,4-dihydroxybenzoate (5 g) and 2-iodopropane (5 g) were added and the mixture was heated at 100° C. for another 2 h. After cooling, the mixture was filtered and concentrated. The residue was purified by flash chromatography eluted with 30:1 toluene/EtOAc to give 3 g of the title compound along with 1.2 g of isomer methyl 4-hydroxy-2-isopropoxybenzoate.

$^1$H NMR (400 MHz, acetone-$d_6$) δ 1.33 (6H, d), 3.90 (3H, s), 4.72 (1H, m), 6.41(1H, s), 6.46 (1H, d), 7.72 (1H, d), 10.91 (1H,s).

Methyl 4-hydroxy-2-isopropoxybenzoate $^1$H NMR (400 MHz, acetone-$d_6$) δ 1.31 (6H, d), 3.60 (1H, m), 3.90 (3H, s), 6.45 (1H, d), 7.56 (1H, d), 9.08 (1H, s), 11.4 (1H,s).

Step 2: methyl 4-isopropoxy-2-[(trifluoromethyl)sulfonyl] oxybenzoate

To a solution of methyl 2-hydroxy-4-isopropoxybenzoate (2.57 g) in $CH_2Cl_2$ (50 mL) cooled at −78° C. was added Et3N (2.5 mL) followed by trifluoromethanesulfonyl anhydride dropwise. The mixture was stirred for 20 min between −30° C. to r.t. and then quenched with 50 mL of saturated aqueous NaHCO3 solution. The mixture was extracted with 100 mL of 4:1 hexane/EtOAc and the extract was dried over $MgSO_4$ and concentrated to give 3 g of the crude title compound as a yellow oil which was used for next step without further purification.

Step 3: 4-isopropoxy-2-(4-methylphenyl)benzoic acid

A mixture of the crude tiflate from Step 2 (3 g), 4-methylbenzeneboronic acid (1.6 g), $K_2CO_3$ (1.3 g) and $Pd(PPh_3)_4$ (0.27 g) in 50 mL of DME was heated in a 90° C. oil bath for 2.5 h. After cooling, the mixture was filtered through a pad of silica gel and concentrated. The residue was dissolved in 100 m-L of 3:1 hexane/EtOAc and filtered again through a pad of silica gel. The filtrate was concentrated and concentrated. The crude was dissolved in mixture of THF (50 mL), MeOH (10 mL) and water (10 mL) and treated with 10 mL of 10N aqueous KOH. The mixture was heated at 60°

C. for 18 h. After cooling, the mixture was acidified with concentrated HCl and diluted with 30 mL of brine and then extracted with 150 mL of EtOAc. The extract was dried over Na$_2$SO$_4$ and concentrated. The residue was swished in 2:1 hexane/EtOAc to give 1.3 g of the title compound as a beige solid.

Step 4: t-butyl 4-Isopropoxy-2-(4-methylphenyl)benzoate

A mixture of the product from Step 3 (1.3 g), 4 mL of N,N-dimethylformamide di-t-butyl acetal (4 mL) in 10 mL of toluene was heated at 100° C. for 6 h. After being concentrated, the residue was suspended in 30 mL of 10:1 hexane/EtOAc and filtered through pad of silica gel. The filtrated was concentrated to give 1.3 g of the crude title compound as an oil.

$^1$HNMR(400 MHz, acetone d$_6$) δ 1.25 (9H, s), 1.33 (6H, d). Step 5 t-butyl 4-Isopropoxy-2-(4-bromomethylphenyl)benzoate A mixture of t-butyl 4-isopropoxy-2-(4-methylphenyl)benzoate (1.3 g), NBS (0.86 g), and benzoyl peroxide (0.05 g) in 30 mL of CCl$_4$ was heated to reflux for 30 min. The mixture was cooled to room temperature, diluted with 20 mL of 10:1 hexane/EtOAc and filtered through a pad of silica gel. The filtrate was concentrated and the residue was purified by flash chromatography eluted with 20:1 hexane/EtOAc to give 1.5 g of the title compound as a white solid.

$^1$H NMR (300 MHz, acetone-d$_6$) δ 1.21 (9H, s), 1.33 (6H, d), 4.72 (2H, s), 4.78 (1H, m), 6.82 (1H, d), 6.98 (1H, dd), 7.30 (2H, d), 7.51 (2H, d), 7.76 (1H, d), Step 6 methyl 2-(1H-1,2,3-benzotriazol-1-yl)-2-phenylacetate A mixture of methyl ?-bromophenylacetate (6.9 g) and benzotriazole (11 g) in 50 mL of toluene was heated to reflux for 22 h, cooled and diluted with 400 mL of CHCl$_3$. The mixture was then washed with 100 mL of 10% aqueous NaOH and the organic layer was dried over Na$_2$SO$_4$ and concentrated. After swishing from 1:1 hexane/EtOAc, 5.7 g of the title compound was obtained as a white solid.

$^1$H NMR (400 MHz, acetone-d$_6$) δ 3.34 (3H, s), 7.15 (1H, s), 7.35–7.50 (5H, m), 7,55 (3H, m), 8.02 (1H,d).

Step 7 benzyl 2-(1H-1,2,3-benzotriazol-1-yl)-2-phenylacetate

A mixture of methyl 2-(1H-1,2,3-benzotriazol-1-yl)-2-phenylacetate (5 g), LiOH (1N, 25 mL), THF (50 mL) and water (20 mL) was stirred for 3 h. AcOH (10 mL), was added and the reaction mixture was extracted with 3×150 mL of EtOAc. The extract was dried over Na$_2$SO$_4$ and concentrated to give 4.5 g of the acid intermediate as a white solid.

A mixture of the acid abtained above (3.8 g), DMAP (0.5 g), benzyl alcohol (1.62 g), and 1-cyclohexyl-3-(2-morpholinoethyl)carbodiimide metho-p-toluenesulfonate (8.5 g) in 200 mL CH$_2$Cl$_2$ was stirred for 16 h. Saturated aqueous NaHCO$_3$ (100 mL), was added and the mixture was extracted with 2:1 EtOAc/hexane (400 mL). The extract was dried over Na$_2$SO$_4$, filtered and concentrated. The residue was purified by flash chromatography eluted with 15:1 toluene/EtOAc to give 4.3 g of the title compound as an oil.

$^1$H NMR (400 MHz, acetone-d$_6$) δ 5.32 (2H, s), 7.22 (1H, s), 7.30–7.60(13H, m), 8.01 (1H,d).

Step 8 benzyl 2-(1H-1,2,3-benzotriazol-1-yl)-3-4-[(di-tert-butoxyphosphoryl)(difluoro)methyl]phenyl-2-phenylpropanoate To a solution of benzyl 2-(1H-1,2,3-benzotriazol-1-yl)-2-phenylacetate (1.05 g), di(tert-butyl) [[4-(bromomethyl)phenyl](difluoro) methyl]phosphonate (1.3 g), 18-crown-6 (0.4 g) in DMF (30 mL) cooled at −40° C. was added a solution of KOtBu (1M, 4 mL) dropwise over 5 min. After being stirred at −30° C. for 1 h, the reaction was quenched with 75 mL of saturated aqueous NH$_4$Cl. The mixture was extracted with 2×200 mL of 3:2 hexane/EtOAc. The extract was dried over Na$_2$SO$_4$, filtered, and concentrated. The residue was purified by flash chromatography eluted with 15:1 toluene/EtOAc containing 2% Et$_3$N to give 0.5 g of the title compound as an oil.

$^1$H NMR (400 MHz, acetone-d$_6$) δ 1.43 (18H, s), 4.38 (2H, d), 4.47 (2H, d), 5.12 (2H, s), 6.66 (1H, s), 6.97 (2H, d), 7.08 (2H, d), 7.15–7.55 (13H, m), 8.02 (1H,d).

Step 9 2-(1H-1,2,3-benzotriazol-1-yl)-3-4-[(di-tert-butoxyphosphoryl) (difluoro)methyl]phenyl-2-phenylpropanoic Acid A mixture of the product from Step 7 (0.5 g) and Pd (0.05 g, 10% on charcoal) in EtOAc (100 mL) was shaken under 30 psi of hydrogen for 24 h. The mixture was then filtered through celite and then filtrate was concentrated to give the crude title compound as an oil which was used for next step without further purification.

Step 10 {4-[2-(1H-1,2,3-benzotriazol-1-yl)-3-[(4-(2-t-butoxycarbonyl-5-isopropoxyphenyl)benzyl)oxy]-3-oxo-2-phenylpropyl]phenyl (difluoro)methylphosphonic Acid, di-t-butyl Ester A mixture of the product from Step 8 (0.12 g), t-butyl 4-Isopropoxy-2-(4-bromomethylphenyl)benzoate (from Step 5, 0.1 g), Cs2CO3(0.1 g) and Bu$_4$NI (0.005 g) in 5 mL of CH$_3$CN was stirred for 4 h. The reaction mixture was then treated with 5 mL of saturated aqueous NH$_4$Cl, 20 mL of water, and extracted with 30 mL of EtOAc. The extract was dried over Na$_2$SO$_4$, filtered and concentrated. The residue was purified by flash chromatography eluted with 3:1 hexane/EtOAc containing 2% Et$_3$N to give 0.13 g of the title compound as an oil.

$^1$H NMR (400 MHz, acetone-d$_6$) δ 1.15 (9H, s), 1.32 (6H, d), 1.40 (18H, s), 4.40 (1H, d), 4.48 (1H, d), 4.75 (1H, m), 5.28 (2H, s), 6.72 (1H, d), 6.77 (1H, s), 6.90–7.40 (16H, m), 7.75 (1H, d), 8.03 (1H,d).

Step 11 {4-[2-(1H-1,2,3-benzotriazol-1-yl)-3-[(4-(2-carboxy-5-isopropoxyphenyl)benzyl)oxy]-3-oxo-2-phenylpropyl]phenyl}(difluoro)methylphosphonic Acid A mixture of the product form Step 9 (0.07 g), TFA (1 mL) and CH$_2$Cl$_2$ (3 mL) was kept at room temperature for 16 h and then was concentrated to give 0.06 g of the title compound.

$^1$H NMR (400 MHz, acetone-d$_6$) δ 1.33 (6H, d), 4.37 (1H, d), 4.43 (1H, d), 4.76 (1H, m), 5.25 (2H, s), 6.68 (1H, d), 6.78 (1H, s), 6.88–7.00 (3H, m), 7.11 (2H, d), 7.18–7.50 (11H, m), 7.77 (1H, d), 8.00 (1H,d).

Example 11

{4-[2-(1H-1,2,3-Benzotriazol-1-yl)-3-[(4-(4-carboxy-3-isopropoxyphenyl) benzyl)oxy]-3-oxo-2-phenylpropyl]phenyl}(difluoro)methylphosphonic Acid Step 1 t-Butyl 2-isopropoxy-4-(4-bromomethylphenyl)benzoate Starting from methyl 4-hydroxy-2-isopropoxybenzoate which was obtained as a by-product in Step 1 of Example 10, the title compound was prepared as a beige solid through the same sequence as described for t-butyl 4-Isopropoxy-2-(4-bromomethylphenyl)benzoate (Step 2 to Step 5 of Example 10).

$^1$H NMR (400 MHz, acetone-d$_6$) δ 1.30 (6H, d), 1.63 (9H, s), 3.03 (1H, m), 4.73 (2H, s), 6.70 (1H, d), 7.28 (2H, d), 7.56 (2H, d), 7.69 (1H, d), 11.67 (1H, s).

Step 2 {4-[2-(1H-1,2,3-benzotriazol-1-yl)-3-[(4-(4-carboxy-3-isopropoxyphenyl)benzyl)oxy]-3-oxo-2-phenylpropyl]phenyl}(difluoro)methylphosphonic Acid Starting from t-butyl 2-isopropoxy-4-(4-bromomethylphenyl) benzoate and 2-(1H-1,2,3- benzotriazol-1-yl)-3-4-[(di-tert-butoxyphosphoryl) (difluoro)methyl]phenyl-2-phenylpropanoic acid (from Step 9 of Example 10), the title compound was prepared through the same sequence as described in Step 10 to Step 11 of Example 10.

$^1$H NMR (400 MHz, acetone-$d_6$) δ 1.28 (6H, d), 2.95 (1H, m), 4.39 (1H, d), 4.45 (1H, m), 5.27 (1H, d), 5.35 (1H, d), 6.67 (2H, d), 6.97 (2H, d), 7.12 (4H, s), 7.20–7.45 (10H, m), 7.75 (1H, d), 8.00 (1H,d).

Example 12
{4-[2-(1H-1,2,3-Benzotriazol-1-yl)-3-[(4-(3-t-butoxycarbonyl-5-isopropoxyphenyl)benzyl)oxy]-3-oxo-2-phenylpropyl]phenyl}(difluoro) methylphosphonic Acid Step 1 t-butyl 3-isopropoxy-5-(4-bromomethylphenyl) benzoate Starting from methyl 3,5-dihydroxybenzoate, the title compound was prepared as a beige solid through the same sequence as described for t-butyl 4-Isopropoxy-2-(4-bromomethylphenyl)benzoate (Step 1 to Step 5 of Example 10).

$^1$H NMR (400 MHz, acetone-$d_6$) δ 1.35 (6H, d), 1.60 (9H, s), 4.72 (2H, s), 4.80 (1H, m), 7.40 (1H, d), 7.45 (2H, s), 7.56 (2H, d), 7.68 (2H, d), 7.78 (1H, s).

Step 2 {4-[2-(1H-1,2,3-Benzotriazol-1-yl)-3-[(4-(3-t-butoxycarbonyl-5-isopropoxyphenyl)benzyl)oxy]-3-oxo-2-phenylpropyl]phenyl}(difluoro)methylphosphonic Acid Starting from t-butyl 3-isopropoxy-5-(4-bromomethylphenyl) benzoate and 2-(1H-1,2,3-benzotriazol-1-yl)-3-4-[(di-tert-butoxyphosphoryl) (difluoro)methyl]phenyl-2-phenylpropanoic acid (from Step 9 of Example 10), the title compound was prepared through the same sequence as described in Step 10 to Step 11 of Example 10 except using AcOH instead of TFA in the last hydrolysis step.

$^1$H NMR (400 MHz, acetone-$d_6$) δ 1.35 (6H, d), 1.60 (9H, s), 4.42 (2H, s), 4.80 (1H, m), 5.25 (1H, d), 5.32 (1H, d), 6.68 (1H, d), 6.92 (2H, d), 7.10–7.52 (12H, m), 7.54 (1H, s), 7.50 (2H, d), 7.73 (1H, s), 7.99 (1H,d).

Example 13
{4-[2-(1 h-1,2,3-benzotriazol-1-yl)-3-[(4-(3-carboxy-5-isopropoxyphenyl) benzyl)oxy]-3-oxo-2-phenylpropyl]phenyl}(difluoro)methylphosphonic Acid Starting from t-butyl 3-isopropoxy-5-(4-bromomethylphenyl) benzoate and 2-(1H-1,2,3-benzotriazol-1-yl)-3-4-[(di-tert-butoxyphosphoryl) (difluoro)methyl]phenyl-2-phenylpropanoic acid (from Step 9 of Example 10), the title compound was prepared through the same sequence as described in Step 10 to Step 11 of Example 10.

$^1$H NMR (400 MHz, acetone-$d_6$) δ 1.37 (6H, d), 4.40 (2H, s), 4.78 (1H, m), 5.25 (1H, d), 5.32 (1H, d), 6.67 (1H, d), 6.97 (2H, d), 7.10–7.45 (12H, m), 7.53 (3H, m), 7.70 (1H, s), 7.99 (1H,d).

Example 14
(4-{2'-(1H-1,2,3-Benzotriazol-1-yl)-3-[2'-(tert-butoxycarbonyl)-5'-isopropoxy(1,1'-biphenyl]-4-yl]-2-phenylpropyl}phenyl)(difluoro) methylphosphonic acid Step 1 tert-butyl 4'-(2-(1H-1,2,3-benzotriazol-1-yl)-3-t4-[[di (tert-butoxy)phosphoryl(difluoro)methyl]phenyl}-2-phenylpropyl)-5-isopropoxy[1,1'-biphenyl]-2-carboxylate To a solution of di(tert-butyl)-{4-[2-(1H-1,2,3-benzotriazol-1-yl)-2-phenylethyl]phenyl}(difluoro) methylphosphonate (0.100 g, 0.184 mmol) in THF (1.0 n-mL) were added in n-BuLi 1.6 M in hexane (0.138 mL) followed by the bromide of Example 10, Step 5 (0.090 g, 0.222 mmol) in THF (0.5 mL). After a period of 10 min, aqueous NH$_4$OAc was added to the reaction mixture. The resulting mixture was extracted with ethyl acetate, dried over Na$_2$SO$_4$, filtered and evaporated under reduced pressure. The title compound was obtained after purification by flash chromatography.

Step 2 (4-{2-(1H-1,2,3-benzotriazol-1-yl)-3-[2'-(tert-butoxycarbonyl)-5'-isopropoxy[1,1'-biphenyl]-4-yl]-2-phenylpropyl}phenyl)(difluoro)methylphosphonic Acid The compound of Step 1 (0.05 g) was dissolved in a 4/1 mixture of HOAc-H$_2$O. After a period of 18 h, the solvents were evaporated under reduced pressure to give the title compound.

$^1$H NMR (400 MHz, CD$_3$COCD$_3$) δ 1.20 (9H, s), 1.30 (6H, d), 4.10 (4H, m), 4.70 (1H, m), 6.65-8.00 (20H, m).

Example 15
4'-(2-(1H-1,2,3-Benzotriazol-1-yl)-3-{4-[difluoro (phosphono)methyl]phenyl}-2-phenylpropyl)-5-isopropoxy [1,1'-biphenyl]-2-carboxylic Acid The compound of Example 14 Step 2 was dissolved in a 4/1 TFA-H$_2$O mixture. After a period of 18 h, the solvents were evaporated to give the title compound.

$^1$H NMR (400 MHz, CD$_3$COCD$_3$) δ 1.30 (6H, d), 4.00 (4H, m), 4.70 (1H, m), 6.05–8.00 (20 H, m).

Example 16
(4-{2-(1H-1,2,3-benzotriazol-1-yl)-3-14'-(tert-butoxycarbonyl)-3'-isopropoxy[1,1'-biphenyl]-4-yl]-2-phenylpropyl}phenyl)(difluoro)methylphosphonic Acid Step 1 tert-butyl 4'(2-(1H-1,2,3-benzotriazol-1-yl)-3-{4-[[di (tert-butoxy)phosphoryl](difluoro)methyl]phenyl}-2-phenylpropyl)-3-isopropoxy[1,1'-biphenyl]-4-carboxylate To a solution of di(tert-butyl) {4-[2-(1H-1,2,3-benzotriazol-1-yl)-2-phenylethyl]phenyl}(difluoro) methylphosphonate (0.060 g, 0.110 mmol) in TRF (1.0 mL) were added n-BuLi 1.6 M in hexane (0.086 mL) and the bromide of Example 11, Step 1 (0.045 g, 0.111 mmol) in THF (1.0 mL). Then using the same protocol as described for Example 14 Step 1 the title compound was obtained.

Step 2 (4-{2-(1H-1,2,3-benzotriazol-1-yl)-3-[4'-(tert-butoxycarbonyl)-3'isopropoxy[1,1'-biphenyl]-4-yl]-2-phenylpropyl}phenyl)(difluoro)methylphosphonic Acid Using the same protocol as described for Example 14 Step 2 the title compound was obtained.

$^1$H NMR (400 MHz, CD$_3$COCD$_3$) δ 1.20 (6H, m), 1.60 (9H, s), 2.90 (4H, m), 6.60-8.00 (20H, m).

Example 17
(4-{2-benzotriazol-1-yl-4-[2'-(1H-tetrazol-5-yl)-biphenyl-4-ylmethylsulfanyl]-2-phenyl-butyl}-phenyl)-difluoro-methyl-phosphonic Acid Step 1 [4-(2-benzotriazol-1-yl-4-(triisopropylsilylthio)-2-phenyl-butyl-phenyl]-difluoro-methyl-phosphonic Acid Diethyl Ester To a −78° C. solution of 1-benzyl-1H-benzotriazole(5 mmol., 1.05 g.) in TBF(25 mL) was added a 2.15M n-BuLi solution until a persistent blue color developed(c.a. 0.2 mL) followed by 1 equivalent(5 mmol., 2.32 mL). The mixture was reacted for 0.25 hour and then 1-bromo-2-(triisopropylsilylthio)-ethane(5.5 mmol., 1.63 g.) in THF(2 mL) was added dropwise. The mixture was reacted for 2 hours. n-BuLi (5 mmol., 2.32 mL) was added dropwise and the mixture was reacted for 0.25 hour. After and (4-bromomethyl-phenyl)-difluoro-methyl-phosphonic acid diethyl ester(5 mmol., 1.79 g.) in THF(2 mL) was added. After 1 hour, the mixture was diluted with ethyl acetate and 1N HCl was added. The mixture was warmed to room temperature. The organic layer was separated and the aqueous further extracted with ethyl acetate. The combined ethyl acetate layers were washed with brine, dried with magnesium sulfate and the solvent removed in vacuo. Purification of the residue by chromatography on $SiO_2$ using ethyl acetate and hexanes(1:2) gave the intermediate thiosilane (2.14 g.) contaminated with a small amount of unreacted (4-bromomethyl-phenyl)-difluoro-methyl-phosphonic acid diethyl ester.

$^1$H NMR ($CD_3COCD_3$), ($\delta$, ppm): 0.8–1.1(21H, m), 1.2–1.4(6H, m), 2.5–2.9(4H, m), 3.9–4.2(6H, m), 6.6–6.7 (2H, d), 7.3–7.4(1H, d), 7.1–7.4(9H, m), 8.0–8.1(1H, d) impurity of bromide observed as singlets at 7.6 ppm and 4.7 ppm.

Step 2 4-{2-benzotriazol-1-yl-4-[2'-(1-triphenylmethyl-1H-tetrazol-5-yl)-biphenyl-4-ylmethylsulfanyl]-2-phenyl-butyl}-phenyl)-difluoro-methyl-phosphonic Acid Diethylester and 4-{2-benzotriazol-1-yl-4-[2'-(3-triphenylmethyl-1H-tetrazol-5-yl)-biphenyl-4-ylmethylsulfanyl]-2-phenyl-butyl}-phenyl)-difluoro-methyl-phosphonic Acid Diethylester To a 0° C. suspension of the diester from step 1 (0.4 mmol; 2 mL of a 0.2 M THF solution), 2'-(3-triphenylmethyl-1H-tetrazol-5-yl)-biphenyl-4-methyl bromide(0.5 mmol., 0.186 g.; U.S. Pat. No. 5,412,102) and cesium carbonate (0.42 mmol., 0.137 g.) was added TBAF (0.42 mmo., 0.420 mL of a 1M THF solution) while a nitrogen stream was passed through the mixture. After 1 hour, the mixture was diluted with ethyl acetate and 1N HCl was added. The organic layer was separated and the aqueous further extracted with ethyl acetate. The combined ethyl acetate layers were washed with brine, dried with magnesium sulfate and the solvent removed in vacuo. Purification of the residue by chromatography on $SiO_2$ using ethyl acetate and hexanes(1:1) gave the diethyl ester(0.191 g.).

$^1$H NMR ($CD_3COCD_3$) ($\delta$, ppm): 1.15–1.3(6H, m), 2.0–2.9(4H, m; resonances hidden under $H_2O$, HOD and acetone-$d_6$), 3.55(2H, s), 3.9–4.2(6H, m), 6.55–6.65(2H, d), 7.0–6.8(12H, m), 7.45–7.1(20H, m), 7.65–7.45(2H, m), 7.8–7.9(1H, d), 8.0–8.1(1H, d).

Step 3 4-{2-benzotriazol-1-yl-4-[2'-(1H-tetrazol-5-yl)-biphenyl-4-ylmethylsulfanyl]-2-phenyl-butyl}-phenyl)-difluoro-methyl-phosphonic Acid.

TMSBr (2 mmol., 0.306 g.) was added to a 0° C. solution of the diester from step 2 and the mixture was stirred at room temperature for 16 hours. The residue was dissolved in $CHCl_3$ and the solution evaporated to dryness. This process was repeated 3 times. It was then dissolved in $CHCl_3$(5 mL) and ethanol was added (5 mL). The resulting solution was stirred at room temperature for 3 hours and then evaporated to dryness. It was dissolved in ethanol and evaporated to dryness again. Finally, the residue was dried on high vacuum to yield the title compound and triphenylcarbinol.

$^1$H NMR, $CD_3COCD_3$, (?, ppm): 2.0–3.1(4H, m), 3.65 (2H, s), 4.0–4.2(2H, AB), 6.5–6.6(2H, M), 6.9–7.1(5H, m), 7.2–7.8(31H, m), 8.1–8.2(1H, d),.; product contains a residual amount of ethanol.

Example 18

[6-(4-{2-benzotriazol-1-yl-3-[4-(difluoro-phosphono-methyl)-phenyl]-2-phenyl-propyl}-phenyl)-2-methyl-quinolin-8-yl]-phosphonic Acid Step 1 Diethyl 6-bromo-2-methyl-8-quinolylphosphonate and diethyl 8-bromo-2-methyl-6-quinolylphosphonate To a degassed solution of 6,8-dibromo-2-methylquinoline (3.01 g, 10 mmol, prepared according to Song et al. J. Heterocyclic Chem. 1993, 39, 17.), diethylphosphite (1.65 g, 12 mmol) and $Et_3N$ (1.21 g, 12 mmol) in toluene (3 mL) was added $Pd(OAc)_2$ (224.5 mg, 1 mmol). The mixture was degassed and $Ph_3P$ (1.049 g, 4 mmol) was added. The mixture was heated to 100° C. for 7 h, cooled, diluted with EtOAc (200 mL) and filtered through celite. The filtrate was concentrated in vacuo. The residue was purified by chromatography on silica gel to give 475 mg (13%) of diethyl 6-bromo-2-methyl-8-quinolylphosphonate and 150 mg (4%) of diethyl 8-bromo-2-methyl-6-quinolylphosphonate.

Step 2 Diethyl 6-[4-(hydroxymethyl)phenyl]-2-methyl-8-quinolylphosphonate

To a degassed solution of diethyl 6-bromo-2-methyl-8-quinolylphosphonate (429 mg, 1.2 mmol, obtained from step 1) and 4-hydroxymethylphenylboronic acid (364 mg, 2.4 mmol) in toluene (6 mL) was added $Pd_2(dba)_3$ (54.9 mg, 0.06 mmol). The mixture was degassed and $Ph_3P$ (125 mg, 0.48 mmol), $Et_2NH$ (105 mg, 1.44 mmol), n-propanaol (0.9 mL) and $H_2O$ (0.9 m-L) was added. The mixture was heated to reflux for 6 h. Aqueous $NaHCO_3$ was added and the resulting mixture was extracted with EtOAc. The combined organic extracts were washed with brine, dried (anhyd. $MgSO_4$) and concentrated in vacuo. The residue was purified by chromatography on silica gel to give 369 mg (79%) of the title compound.

Step 3 diethyl 6-[4-(bromomethyl)phenyl]-2-methyl-8-quinolylphosphonate

To a solution of $POBr_3$ (150 mg, 0.39 mmol) in $CH_2Cl_2$ (4 mL) and DMF (2 mL) was added the product of step 2 (150 mg, 0.39 mmol). The mixture was stirred at r.t. for 0.5 h. $H_2O$ was added and the mixture was extracted with EtOAc. The combined organic extracts were washed with brine, dried (anhyd. $MgSO_4$) and concentrated in vacuo. The residue was purified by chromatography on silica gel to give 159 mg (91%) of the title compound.

Step 4 {6-[4-(2-benzotriazol-1-yl-3-4-[(di-tert-butoxy-phosphoryl)-difluoro-methyl]-phenyl}-2-phenyl-propyl)-phenyl]-2-methyl-quinolin-8-yl}-phosphonic Acid Diethyl Ester To a solution of [4-(2-benzotriazol-1-yl-2-phenylethyl) phenyl] difluoromethylphosphonic acid di-tert-butyl ester (Example 1, step 2) (77 mg, 0.14 mmol) in THF (2 mL) at −78° C. was added a 2.5 M hexane solution of n-BuLi (0.067 mL, 0.16 mmol). The mixture was stirred at −78° C. for 10 min. A solution of the product of step 3 (64 mg, 0.14 mmol) was added. The resulting red solution was stirred at −78° C. for 0.5 h and then warmed to −40° C. for 1 h. $H_2O$ was added and the mixture was extracted with EtOAc. The combined organic extracts were washed with brine, dried (anhyd. $MgSO_4$) and concentrated in vacuo. The residue was purified by chromatography on silica gel to give 119 mg (93%) of the title compound.

Step 5 [6-(4-{2-benzotriazol-1-yl-3-[4-(difluoro-phosphono-methyl)-phenyl]-2-phenyl-propyl}-phenyl)-2-methyl-quinolin-8-yl]-phosphonic Acid To a solution of the product of step 4 (106 mg, 0.11 mmol) in $CHCl_3$ (2 mL) was added TMSBr (153 mg, 1 mmol) The mixture was heated to 70° C. for 3 h. The mixture was concentrated in vacuo, the residue was coevaporated with $CHCl_3$ twice. EtOH (2 mL) was added, the mixture was stirred at r.t. for 0.5 h and concentrated in vacuo. The product was swished with $CHCl_3$ to give 80 mg of the title compound.

$^1$H NMR (DMSO-$d_6$) $\delta$ 2.87 (s, 3H), 3.90 (dd, 2H), 4.09 (dd, 2H), 6.73 (m, 5H) 7.09 (d, 2H), 7.21 (d, 2H), 7.35 (m, 5H), 7.53 (d, 2H), 7.87 (d, 1H), 8.11 (d, 1H), 8.41 (d, 11H), 8.57 (s, 1IH), 8.83 (d, 11H).

Example 19

[6-(4-{2-Benzotriazol-1-yl-3-[4-(difluoro-phosphono-methyl)-phenyl]-2-phenyl-propyl]-phenyl)-2-(1-methoxy-3-methyl-butyl)-quinolin-8-yl]-phosphonic acid Step 1 diethyl 6-bromo-2-methyl-8-quinolylphosphonate and diethyl 8-bromo-2-methyl-6-quinolylphosphonate To a degassed suspension of $(Ph_3P)_4Pd$ in diethylphosphite (5.4 g, 39.4 mmol), $Et_3N$ (3.9 g, 39.4 mmol) was added a solution of 6,8-dibromo-2-methylquinoline (10.8 g, 35.8 mmol, prepared according to Song et al. J. Heterocyclic Chem. 1993, 39, 17.) in toluene (10 mL). The mixture was heated to 90° C. for 7 h. The mixture was diluted with ether (200 mL) and stirred vigorously. The ether extract was decanted and the residue was extracted 2 more times with ether (200 mL). The combined ether extracts were washed with aqueous $NaHCO_3$, dried (anhyd. $MgSO_4$) and concentrated in vacuo. The residue was purified by chromatography on silica gel to give 5.97 g (46%) of a 1:1 mixture of the title compounds.

Step 2 diethyl 6-bromo-2-formyl-8-quinolylphosphonate and diethyl 8-bromo-2-formyl-6-quinolylphosphonate To a suspension of the product of step 1 (5.75 g, 16 mmol) in dioxane (80 mL) and $H_2O$ (16 mL) was added $SeO_2$ (5.34 g, 48 mmol). The mixture was heated to 90° C. for 1 h. The mixture was cooled and added to a vigorously stirring mixture of ether (400 mL) and aqueous $NaHCO_3$ (200 mL). After stirring for 0.25 h, the mixture was filtered and the two phases are separated. The aqueous solution was extracted with ether (200 mL) twice. The combined ether extracts were washed with aqueous $NaHCO_3$, dried (anhyd. $MgSO_4$) and concentrated in vacuo. The residue was purified by chromatography on silica gel to give 1.45 g (46%) of diethyl 6-bromo-2-formyl-8-quinolylphosphonate and 1.28 g (21%) diethyl 8-bromo-2-formyl-6-quinolylphosphonate.

Step 3 diethyl 6-bromo-2-(1-hydroxy-3-methylbutyl)-8-quinolylphosphonate

To a solution of diethyl 6-bromo-2-formyl-8-quinolylphosphonate (293 mg, 0.78 mmol) in toluene (6 mL) at −10° C. was added a 2M solution of isobutylmagnesium bromide in THF (1.59 mL, 3.12 mmol). The mixture was stirred at −10° C. to −5° C. for 2 h. Aqueous $NH_4CL$ was added and the mixture was extracted with EtOAc. The organic extracts were washed with brine, dried (anhyd. $MgSO_4$) and concentrated in vacuo. The residue was purified by chromatography on silica gel to give 179 mg (53%) of the title compound Step 4 diethyl 6-bromo-2-(1-methoxy-3-methylbutyl)-8-guinolylphosphonate To a solution of the product of step 3 (399 mg, 0.92 mmol) in THF (4 mL) at 0° C. was added NaH (73.6 mg, 1.84 mmol, 60% in oil). To the resulting green suspension was added MeI (259 mg, 1.84 mmol). The mixture was stirred at r.t. for 1.5 h, Aqueous $NH_4CL$ was added and the mixture was extracted with EtOAc. The organic extracts were washed with brine, dried (anhyd. $MgSO_4$) and concentrated in vacuo. The residue was purified by chromatography on silica gel to give 280 mg (68%) of the title compound.

Step 5 [6-(4-{2-benzotriazol-1-yl-3-[4-(difluoro-phosphono-methyl)-phenyl]-2-phenyl-propyl}-phenyl)-2-(1-methoxy-3-methyl-butyl)-quinolin-8-yl]-phosphonic Acid Starting from the product obtained from step 3, following the procedure of Example 18 step 2 to step 5, the title compound was obtained as a beige solid.

1H NMR (DMSO-$d_6$) δ 0.91 (d, 3H), 0.94 (d, 3H), 1.65 (m, 1H), 1.85 (m, 2H), 3.35 (s, 3H), 3.85 (m, 4H), 4.20 (m, 2H), 4.33 (m, 2H), 4.68 (m, 2H), 5.05 (m, 1H), 6.55 (m, 2H), 6.65 (m, 3H), 7.00 (m, 2H), 7.25, (m, 7H), 7.45 (m, 2H), 7.80(m, 1H), 8.00 (m, 2H), 8.40 (m, 1H), 8.55 (m, 1H).

Example 20

[6-(4-{2-Benzotriazol-1-yl-3-[4-(difluoro-phosphono-methyl)-phenyl]-2-phenyl-propyl}-phenyl)-2-(1-methoxymethoxy-3-methyl-butyl)-quinolin-8-yl]-phosphonic Acid Diethyl Ester Step 1 diethyl 6-bromo-2-[1-(methoxymethoxy)-3-methylbutyl]-8-quinolylphosphonate To a solution of diethyl 6-bromo-2-(1-hydroxy-3-methylbutyl)-8-quinolylphosphonate (219 mg, 0.51 mmol) (Example 19, step 3) in THF (2 mL) at 0° C. was added NaH (40 mg, 1.02 mmol, 60% in oil). To the resulting green suspension was added chloromethyl methyl ether (82 mg, 1.02 mmol). The mixture was stirred at r.t. for 1.5 h, Aqueous $NH_4Cl$ was added and the mixture was extracted with EtOAc. The organic extracts were washed with brine, dried (anhyd. $MgSO_4$) and concentrated in vacuo. The residue was purified by chromatography on silica gel to give 170 mg (70%) of the title compound.

Step 2 [6-(4-{2-benzotriazol-1-yl-3-[4-(di-tert-butoxy-phosphoryl)-difluoro-methyl]-phenyl]-2-phenyl-propyl}-phenyl)-2-(1-methoxymethoxy-3-methyl-butyl)-quinolin-8-yl]-phosphonic Acid Diethyl Ester Starting from diethyl 6-bromo-2-[1-(methoxymethoxy)-3-methylbutyl]-8-quinolylphosphonate obtained in step 1, the title compound was prepared using the same sequence described in step 2 to step 4 of Example 18.

Step 3 [6-(4-{2-benzotriazol-1-yl-3-[4-(difluoro-phosphono-methyl)-phenyl]-2-phenyl-propyl}-phenyl)-2-(1-methoxymethoxy-3-methyl-butyl)-quinolin-8-yl]-phosphonic Acid Diethyl Ester To a solution of the product of step 2 (25 mg, 0.024 mmol) in HOAc (0.5 mL) was added $H_2O$ (0.1 mL). The mixture was stirred at r.t. for 72 h. Removal of solvent under vaccum gave the title compound.

$^1$H NMR (Acetone-$d_6$) δ 0.95 (d, 3H), 0.99 (d, 3H), 1.58 (m, 1H), 1.72 (m, 2H), 3.31 (s, 3H), 3.93 (dd, 2H), 4.08 (t, 3H), 4.70 (m, 1H), 6.73 (m, 4H), 7.10 (d, 2H), 7.21, (d, 2H), 7.30 (m, 5H), 7.52 (d, 2H), 7.85 (d, 1H), 8.10 (d, 1H), 8.30 (s, 1H), 8.40 (d, 1H), 8.53 (s, 1H), 8.77 (d, 1H).

Example 21

[6-(4-{2-Benzotriazol-1-yl-3-[4-(difluoro-phosphono-methyl)-phenyl]-2-phenyl-propyl}-phenyl)-2-(1-hydroxy-3-methyl-butyl)-quinolin-8-yl]-phosphonic Acid Starting from the product obtained from step 2 of Example 20, the title compound was prepared using the same procedure described in step 5 of Example 18.

$^1$H NMR (DMSO-$d_6$) δ 0.91 (d, 3H), 0.99 (d, 3H), 1.65 (m, 2H), 1.88 (m, 1H), 3.93 (dd, 2H), 4.08 (dd, 2H), 5.10 (m, 1H), 6.72 (m, 4H), 7.08 (d, 2H), 7.21, (d, 2H), 7.34 (m, 5H), 7.55 (d, 2H), 8.02 (d, 1H), 8.11 (d, 1H), 8.30 (s, 1H), 8.46 (d, 1H), 8.64 (s, 1H), 8.92 (d, 1H).

Example 22

[(4-{2-Benzotriazol-1-yl-3-[4-(5-methoxycarbonyl-thieno[3,2-b-pyridin-3-yl)-phenyl]-2-phenyl-propyl}-phenyl)-difluoro-methyl]-phosphonic Acid Step 1 methyl 3-bromo-thieno[3,2-b]pyridine-5-carboxylate 3-Bromo-thieno[3,2-b]pyridine-5-carboxylic acid (Gronowitz, S.; Westerlund, C.; Hornfeldt, A. -B.; Acta Chem Scand. 29, 233, 1975) was esterified to the corresponding methyl ester. To a solution of the resulting methyl thieno[3,2-b]pyridine-5-carboxylate 9.7 g, 50.2 mmol) in $CHCl_3$ at 0° C. was added a solution of bromine (16 g, 100.4 mmol) in $CCl_4$ (150 mL) dropwise. The mixture was warmed to r.t. and stirred for 72 h. EtOAc (750 mL) was added. The mixture was washed with NaHSO$_3$, dried (anhyd. MgSO$_4$) and concentrated in vacuo. The residue was purified by chromatography on silica gel to give 2.84 g (21%) of the title compound and 5.5 g of starting material.
Step 2 [(4-{2-benzotriazol-1-yl-3-[4-(5-methoxycarbonyl-thieno[3,2-b-pyridin-3-yl)-phenyl]-2-phenyl-propyl-phenyl)-difluoro-methyl]-phosphonic Acid di-tert-butyl Ester Starting from methyl 3-bromo-thieno[3,2-b]pyridine-5-carboxylate obtained in step 1, the title compound was prepared using the same sequence described in step 2 to step 4 of Example 18.
Step 3 [(4-{2-benzotriazol-1-yl-3-[4-(5-methoxycarbonyl-thieno[3,2-b-pvridin-3-yl)-phenyl]-2-phenyl-propyl}-phenyl)-difluoro-methyl]-phosphonic Acid Starting from the product obtained from step 2, the title compound was prepared using the same procedure described in step 5 of Example 18.

$^1$H NMR (Acetone-d$_6$) δ 3.92 (s, 3H), 3.94 (m, 2H), 4.07 (q, 2H), 6.71 (m, 4H), 7.10 (d, 2H), 7.21 (d, 2H), 7.45 (,m, 5H), 7.90 (d, 2H), 8.05 (d, 1H), 8.10 (d, 1H), 8.30 (s, 1H), 8.48 (s, 1H), 8.71 (d, 1H).

Example 23
3-(4-{2-benzotriazol-1-yl-3-[4-(difluoro-phosphono-methyl)-phenyl]-2-phenyl-propyl}-phenyl)-thieno[3,2-b]pyridine-5-carboxylic Acid Trisodium Salt To a solution of the product of step 3, Example 22 (44 mg, 0.062 mmol) in MeOH (1 mL) and THF (0.2 mL) was added a 1N NaOH solution (0.186 mmol, 0.186 mL). The mixture was stirred at r.t. for 20 h. The solvent was removed under vaccum, and the residue was dissolved in H$_2$O and freeze dried to give the title compound.

Example 24
[4-(1-Benzotriazol-1-yl-2-biphenyl-3-yl-2-hydroxy-1-phenylethyl)phenyl]difluoromethylphosphonic Acid
Step 1 [4-(1-benzotriazol-1-yl-2-biphenyl-3-yl-2-hydroxy-1-phenylethyl)phenyl]difluoromethylphosphonic Acid di-tert-butyl Ester To a solution of 4-(2-benzotriazol-1-yl-2-phenylethyl)phenyl] difluoromethylphosphonic acid di-tertbutyl ester (500 mg) in THF at −78° C. was added a solution of n-butyl lithium (0.63 mL, 1.6M/hexane). The resulting mixture was stirred for 5 min at −78° C., then biphenyl-3-carboxaldehyde (201 mg) in THF was added. The mixture was stirred 15 minutes at −78° C., then water was added and the mixture was left to warm to room temperature, extracted with ethyl acetate, washed with brine, dried over MgSO$_4$, filtered and the solvent evaporated under vacuum. The residue was purified by silica gel chromatography using 20% EtOAc/hexane. This afforded the fast moving compound pure.

$^1$H NMR (CD$_3$COCD$_3$) δ 1.41(18H, s), 3.69(1H, d), 4.50(1H, d),5.20(1H, s, br), 6.24(1H, s), 6.67–7.56(21H,m), 8.05(1H, d).

The slow moving compound, was repurified by silica gel chromatography using 8% acetone/toluene.

$^1$H NMR (CD$_3$COCD$_3$) δ 1.30(18H, d), 4.11(2H, m),5.19 (1H, d),6.34(1H, d), 6.39(1H, d), 6.92(1H, s), 7.04(1H, t), 7.13–7.56(18H, m),7.97(1H, d).

Step 2 3-[4-(1-benzotriazol-1-yl-2-biphenyl-3-yl-2-hydroxy-1-phenylethyl)phenyl]difluoromethylphosphonic Acid.

A solution of the fast moving compound from the previous step (108 mg) in acetic acid (5 mL) and water (1 mL) was stirred at room temperature over night. The solvent was then evaporated under vacuum and the residue chromato-graphed on reverse phase silica gel (bondapak C$_{18}$, 125 Å, 15–20 microns) using 40% acetonitrile/water.

$^1$H NMR (CD$_3$COCD$_3$) δ 3.68(1H, d), 4.50(1H, d), 6.27 (1H, s),6.75–7.48(20H, m), 8.00(1H, d).

Similarly, the slow moving compound from the previous step (60 mg) in acetic acid (5 mL) and water (1 mL) was stirred at room temperature over night. The solvent was then evaporated under vacuum and the residue chromatographed on reverse phase silica gel (bondapak C$_{18}$, 125 Å, 15–20 microns) using 40% acetonitrile/water.

$^1$H NMR (CD$_3$COCD$_3$) 4.02(2H, m), 6.22(1H, d), 6.40 (1H, s), 6.71(1H, d), 6.97–7.53(18H, m), 7.91(1H,d).

Example 25
4'(2-(1H-1,2,3-Benzotriazol-1-yl)-3-{4-[difluoro (phosphono)methyl]phenyl}-2-phenylpropyl)(1,1'-biphenyl]-3-carboxylic Acid
Step 1 tert-butyl 4'-methyl[1,1 biphenyl]-3-carboxylate A mixture of 4-methylphenylboronic acid (0.65 g, 4.3 mmol), t-butyl-3-iodobenzoate (0.87 g, 2.86 mmol), K$_2$CO$_3$ (0.59 g, 4.3 mmol), and (Ph$_3$P)$_4$ Pd (0.17 g, 0.14 mmol) in DME (15 mL) was degassed and flushed with N$_2$ before being brought to reflux for 2 h. Following a standard aqueous/EtOAc work-up, the residue was triturated with 1:10 EtOAc/hexane. The excess boronic acid was removed by filtration, and the filtrate was concentrated to give an oil which was purified by flash chromatography (hexane) to give an oil (0.6 g). This material (≈60% pure) was used as such for the next step.

Step 2 tert-butyl 4'-(bromomethyl)[1,1'-biphenyl]-3 carboxylate

To a solution of the product from Step 1 (0.49 g, ≈1.1 mmol) in CCl$_4$ (8 mL) was added NBS (0.20 g, 1.1 mmol) and benzoyl peroxide (25 mg). The mixture was illuminated with a 150 W spot lamp which brought it to reflux for 30 min. The solvent was then evaporated and the residue was purified by flash chromatography (1:100 EtOAc:hexane, 1:50 EtOAc:hexane) to give a colourless oil (275 mg) which slowly crystallized.

$^1$H NMR (acetone d$_6$) δ 1.60 (s, 9H), 4.71 (s, 2H), 7.54–7.62 (m, 2H), 7.67–7.72 (m, 1H), 7.74–7.82 (m, 2H), 7.86–7.93 (m, 1H), 7.93–8.00 (m, 1H), 8.21–8.25 (m, 1H).

Step 3 tert-butyl 4'-(2-(1H-1,2,3-benzotriazol-1-yl)-3- f 4-[[di(tert-butoxy)phosphoryl](difluoro)methyllphenyl}-2-phenylpropyl)[1,1'-biphenyl]-3-carboxylate A degassed solution of the product from Example 1, Step 2 (121 mg, 0.22 mmol) in THF (2.5 mL) under N$_2$ was cooled to -78° C. and a solution of BuLi (0.25 mL, 0.25 mmol, 1.0 M/hexane) was added slowly. To the reaction mixture was then added a solution of the product from Step 2 (78 mg, 0.22 mmol) in THF (1 mL) via double-tipped needle. After an additional 5 min. at −78° C., the reaction was quenched by the addition of saturated NH$_4$Cl solution. The product was extracted with EtOAc and the organic layer was washed with H$_2$O and brine. After drying (MgSO$_4$), filtering, and removal of solvent, the product was purified by flash chromatography (1:3 EtOAc: hexane containing 1% Et$_3$N) to give a colourless oil (37 mg).

$^1$H NMR (acetone d$_6$) δ 1.42 (s, 18H), 1.59 (s, 9H), 3.95–4.22 (m, 4H), 6.72–6.85 (m, 4H), 7.12–7.16 (m, 2H), 7.24–7.43 (m, 9H), 7.47–7.55 (m, 2H), 7.77–7.81 (m, 1H), 7.88–7.93 (m, 1H), 8.03–8.07 (m, 1H), 8.11–8.14 (m, 1H).
Step 4 4'[(2-(1H-1,2,3-benzotriazol-1-yl)-3-1 4-[difluoro (phosphono) methyl]phenyl}-2-phenylpropyl)(1,1'-biphenyl]-3-carboxylic Acid The material from Step 3 (37 mg) was treated with TFA (1 mL) at r.t. for 2 h. The solvent was removed and the residue was triturated with Et$_2$O to give a gummy semi-solid (12 mg).

$^1$H NMR (acetone d$_6$) δ 3.95–4.18 (m, 4H), 6.74–6.84 (m, 4H), 7.11–7.17 (m, 2H), 7.26–7.45 (m, 9H), 7.45–7.58 (m, 2H), 7.80–7.85 (m, 1H), 7.95–8.03 (m, 2H), 8.20 (s, 1H).

Example 26

4'-{2-Benzotriazol-1-yl-3-[4-(difluorophosphonomethy) phenyl]-2-phenylpropyl}-4-methoxybiphenyl-3-yl-phosphonic Acid Step 1 4'-methoxy-4-methylbiphenyl A mixture of 4-methylbenzeneboronic acid (10 g, 73.5 mmol), 4-bromoanisole (25 g, 134 mmol) and 2M aqueous Na$_2$CO$_3$ (75 mL, 150 mmol) in DMF (350 mL) was passed N$_2$ for 15 min. [1,1'Bis(diphenylphosphino)ferrocene] dichloropalladium (II), complex with dichloromethane (1:1) (200mg, 0.24 mmol) was added and the mixture was heated at 85° C. for 4 h. After cooling to r.t., the mixture was diluted with H$_2$O and extracted with EtOAc. The EtOAc extract was washed with brine (2×), dried (anhydrous MgSO$_4$) and concentrated. The residue was dissolved in small amount of CH$_2$Cl$_2$, filtered through a short pack (~2.5") of silica gel in a 600 mL sintered glass funnel and washed the silica with hexanes:EtOAc (4:1). The filtrate was evaporated. The residue was swished with hexanes to give a white flake. The mother liquor was concentrated and swished again with hexanes. After 4 cycles, the combined yield of title product was 10.5 g (72% based on the boronic acid used.).

$^1$H NMR (Acetone-d$_6$) δ 3.30 (s, 3H), 6.98 (d, 2H), 7.22 (d, 2H), 7.48 (d, 2H), 7.55 (d, 2H).

Step 2 4'-methy-4-hydroxybiphenyl

To a solution of 4'-methoxy-4-methylbiphenyl (10.5 g, 53 mmol) in CH$_2$Cl$_2$ (300 mL) at 0° C. was added a solution of 1M BBr$_3$ in CH$_2$Cl$_2$ (65 mL, 65 mmol). The mixture was slowly warmed to r.t. and stirred overnight. After cooling to 0° C. again, the mixture was quenched with H$_2$O. The CH$_2$Cl$_2$ layer was separated, washed with H$_2$O, dried (MgSO$_4$) and concentrated to give the title compound as a white solid (9.5 g, 97% yield).

$^1$H NMR (Acetone-d$_6$) δ 2.32 (s, 3H), 6.88 (d, 2H), 7.20 (d, 2H), 7.45 (m, 4H), 8.38 (br s, 1H).

Step 3 4'-methyl-biphenyl Dimethyl Phosphate

A mixture of 4'-methyl-4-hydroxybiphenyl (4.3 g, 23.4 mmol) and dicyclohexylamine (5.2 mL, 26.1 mmol) in acetone (30 mL) was refluxed for 1 h. Solvent was then evaporated in vacuo. The residue was dissolved in CCl$_4$ (120 mL) and mixed with dimethyl phosphite (2.4 mL, 26.2 mmol). The mixture was refluxed for 4 h., cooled to r.t. and filtered. The filtrate was concentrated and chromatographed over silica gel eluting with hexanes:EtOAc (2:3) to give 6.5 g (95%) of the title compound as a white solid.

$^1$H NMR (Acetone-d$_6$) δ 2.36 (s, 3H), 3.84 (s, 3H), 3.86 (s, 3H), 7.25 (d, 2H), 7.30 (d, 2H), 7.54 (d, 2H), 7.65 (d, 2H).

Step 4 4-hydroxy-4'-methylbiphenyl-3-yl-phosphonic Acid Dimethyl Ester

To a solution of LDA [prepared from diisopropylamine (3.5 mL, 24.5 mmol) and 2.2M n-butyllithium in hexanes (12 mL, 26.4 mmol)] in THF (120 mL) at −78° C. was added a solution of 4'-methyl-biphenyl dimethyl phosphate (6.1 g, 20.9 mmol) in THF (20 mL). The mixture was stirred at −78° C. for 1 h and then at r.t. for 1 h. After quenching with 2M aqueous HOAc (10 mL), solvent was removed in vacuo. The residue was diluted with H$_2$O and extracted with EtOAc. The EtOAc extract was washed with H$_2$O (2×), dried (MgSO$_4$) and concentrated. Chromatography over silica gel and elution with hexanes:EtOAc (3:2) provided 1.3 g of 4'-methyl-4-hydroxybiphenyl. Further elution gave 4.0 g (65.5%) of the title compound as a white solid.

$^1$H NMR (Acetone-d$_6$) δ 2.34 (s, 3H), 3.77 (s, 3H), 3.80 (s, 3H), 7.02 (m, 1H), 7.25 (d, 2H), 7.48 (d, 2H), 7.60 (d, 1H), 7.80 (m, 1H), 10.35 (br s, 1H).

Step 5 4-methoxy-4'-methylbiphenyl-3-yl-phosphonic Acid Dimethyl Ester

A mixture of 4-hydroxy-4'-methylbiphenyl-3-yl-phosphonic acid dimethyl ester (500 mg, 1.7 mmol), iodomethane (342 mg, 2.4 mmol) and 10 M aqueous NaOH (190 μL, 1.9 mmol) in DMF (10 mL) was stirred at r.t. overnight. After dilution with H$_2$O, the mixture was extracted with EtOAc. Chromatography over silica gel and elution with EtOAc with 5% of MeOH gave 330 mg (63%) of title compound as a white solid.

$^1$H NMR (Acetone-d$_6$) δ 2.35 (s, 3H), 3.72 (s, 3H), 3.74 (s, 3H), 3.93 (s, 3H), 7.20 (m, 1H), 7.26 (d, 2H), 7.49 (d, 2H), 7.82 (m, 1H), 7.99 (d, 1H).

Step 6 4'-bromomethyl-4-methoxybiphenyl-3-yl-phosphonic Acid Dimethyl Ester

A mixture of 4-methoxy-4'-methylbiphenyl-3-yl-phosphonic acid dimethyl ester (300 mg, 1.1 mmol), N-bromosuccinimide (190 mg, 1.1 mmol) and a few crystal of benzoyl peroxide in CCl$_4$ (15 mL) was refluxed and irradiated with a sun lamp for 1 h. More N-bromosuccinimde (30 mg, 0.17 mmol) was added and the mixture was refluxed for 30 min. After cooling to r.t., the mixture was diluted with CH$_2$Cl$_2$ and washed with H$_2$O (3×), dried (MgSO$_4$) and concentrated. The solid residue was swished with Et$_2$O to give 280 mg (67%) of the title compound as a white solid.

$^1$H NMR (Acetone-d$_6$) δ 3.72 (s, 3H), 3.74 (s, 3H), 3.94 (s, 3H), 4.70 (s, 2H), 7.22 (m, 1H), 7.54 (d, 2H), 7.62 (d, 2H), 7.88 (m, 1H), 8.02 (m, 1H).

Step 7 4'-{2-benzotriazol-1-yl-3-[4-(difluorophosphonomethy) phenyl]-2-phenylpropyl 1-4-methoxybiphenyl-3-yl-phosphonic Acid Dimethyl Ester To a solution of [4-(2-benzotriazol-1-yl-2-phenylethyl) phenyl]difluoromethyl-phosphonic acid di-tert-butyl ester (541 mg, 1.0 mmol) in THF (10 mL) at −78° C. was added a solution of 2.5M n-BuLi in hexanes (440 μL, 1.1 mmol). The solution turned deep blue immediately. After stirring for 15 min at −78° C., a solution of 4'-bromomethyl-4-methoxybiphenyl-3-yl-phosphonic acid dimethyl ester (280 mg, 0.72 mmol) in THF (2.0 mL) was added. The deep blue color disappeared. The mixture was then stirred at −78° C. for 15 min, quenched with H$_2$O and extracted with EtOAc. The EtOAc extract was washed with brine, dried (Na$_2$SO$_4$) and concentrated. Chromatography over silica gel and elution with EtOAc with 0.5% of Et$_3$N, then EtOAc with 4% of MeOH and 0.5% Et$_3$N gave 330 mg (39%) of the title compound as a white foam.

$^1$H NMR (Acetone-d$_6$) δ 1.42 (s, 18H), 3.70 (s, 3H), 3.73 (s, 3H), 3.92 (s, 3H), 4.20–3.95 (m, 4H), 6.70 (d, 2H), 6.80 (m, 3H), 7.40–7.10 (m, 12H), 7.77 (m, 1H), 7.94 (m, 1H), 8.04 (d, 1H).

Step 8 4'-12-Benzotriazol-1-yl-3-[4-(difluorophosphonomethy) phenyl]-2-phenylpropyl}-4-methoxybiphenyl-3-yl-phosphonic Acid A solution of 4'-{2-benzotriazol-1-yl-3-[4-(difluorophosphonomethy)phenyl]-2-phenylpropyl}-4-methoxybiphenyl-3-yl-phosphonic acid dimethyl ester (330 mg, 0.39 mmol) and bromotrimethylsilane (1 mL) in CH$_2$Cl$_2$ (5 mL) was stirred at r.t. overnight. Volatile mateials were removed in vacuo. The residue was co-evaporated with ~90% aqueous EtOH (3×) to give the title compound as a light brown foam.

$^1$H NMR (Methanol-d$_4$) δ 3.91 (s, 3H), 4.20–3.94 (m, 4H), 6.56 (d, 2H), 6.71 (d, 2H), 6.76 (d, 2H), 7.10 (m, 3H), 7.45–7.20 (m, 9H), 7.69 (m, 1H), 7.88 (m, 1H), 8.01 (d, 1H).

Example 27

4'-2-Benzotriazol-1-yl-3-[4-(difluorophosphonomethy) phenyl]-2-phenylpropyl 1-4-(3-methylbutoxy)biphenyl-3-yl-phosphonic acid Step 1 4'-bromomethyl-4-(3-methylbutoxy)biphenyl-3-yl-phosphonic Acid Dimethyl Ester The title compound was prepared in a similar manner as described in Step 5-6 of Example 32 from 4-hydroxy-4'-methylbiphenyl-3-yl-phosphonic acid dimethyl ester and 4-bromo-2-methyl-butene. The double bond in the intermediate was reduced by hydrogenation before bromination of the methyl group.

$^1$H NMR (Acetone-d$_6$) δ 0.98 (d, 6H), 1.73 (m, 2H), 1.98 (m, 1H), 3.72 (s, 3H), 3.75 (s, 3H), 4.19 (t, 2H), 4.70 (s, 2H), 7.23 (m, 1H), 7.54 (d, 2H), 7.62 (d, 2H), 7.85 (m, 1H), 8.03 (m, 1H).

Step 2 4'-1 2-benzotriazol-1-yl-3-[4-(difluorophosphonomethy) phenyl]-2-phenylpropyl}-4-(3-methylbutoxy)biphenyl-3-yl-phosphonic Acid The title compound was prepared in a similar manner as described in step 7-8 of Example 32.

$^1$H NMR (Methanol-d$_4$) δ 0.98 (d, 6H), 1.74 (m, 2H), 1.95 (m, 1H), 3.90–4.20 (m, 4H), 4.14 (t, 2H), 6.66 (d, 2H), 6.71 (d, 1H), 6.74 (d, 2H), 7.10 (m, 3H), 7.20–7.45 (m, 9H), 7.67 (m, 1H), 7.90 (m, 1H), 8.01 (d, 1H),

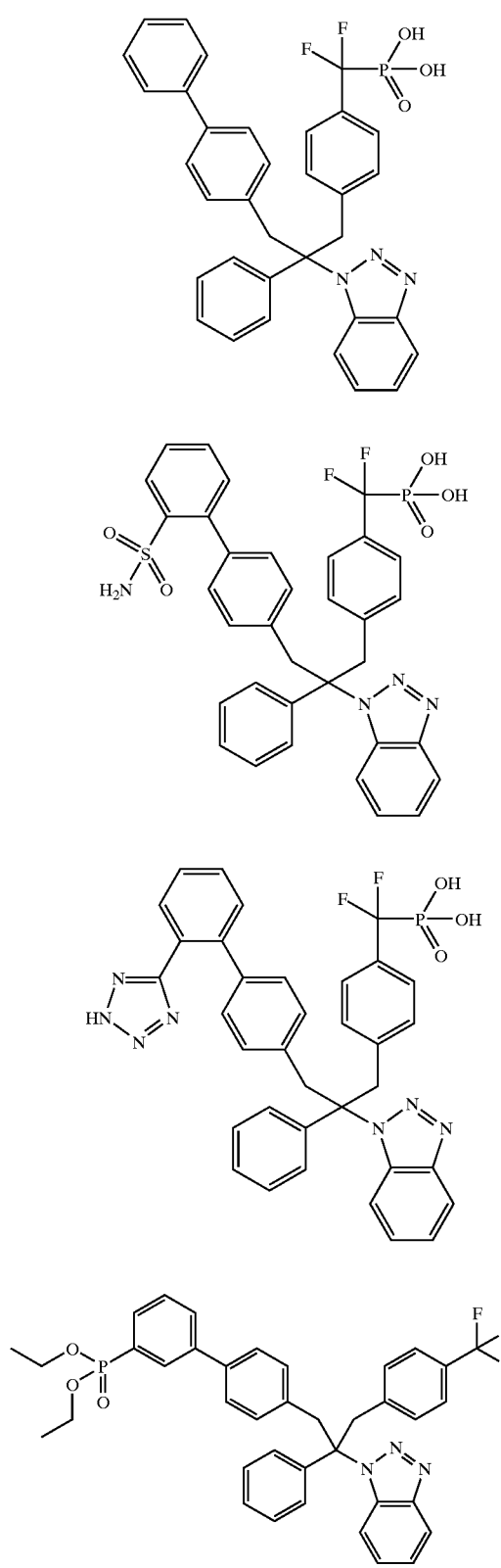
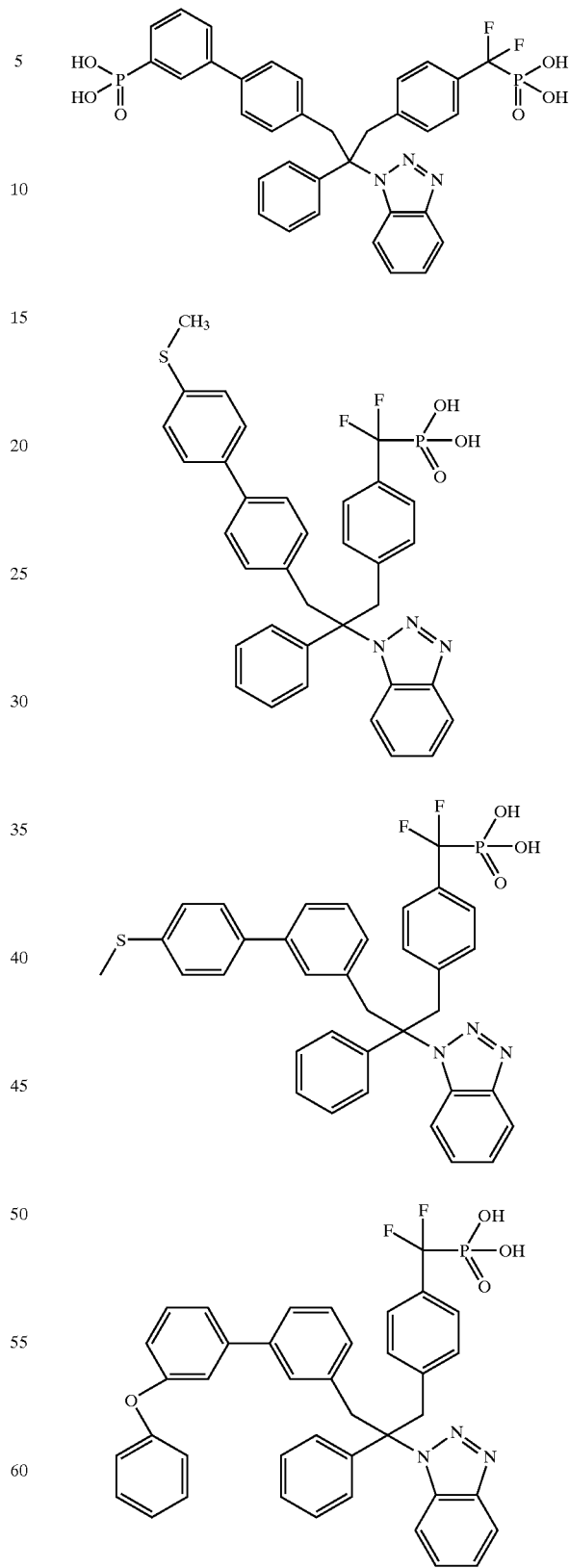

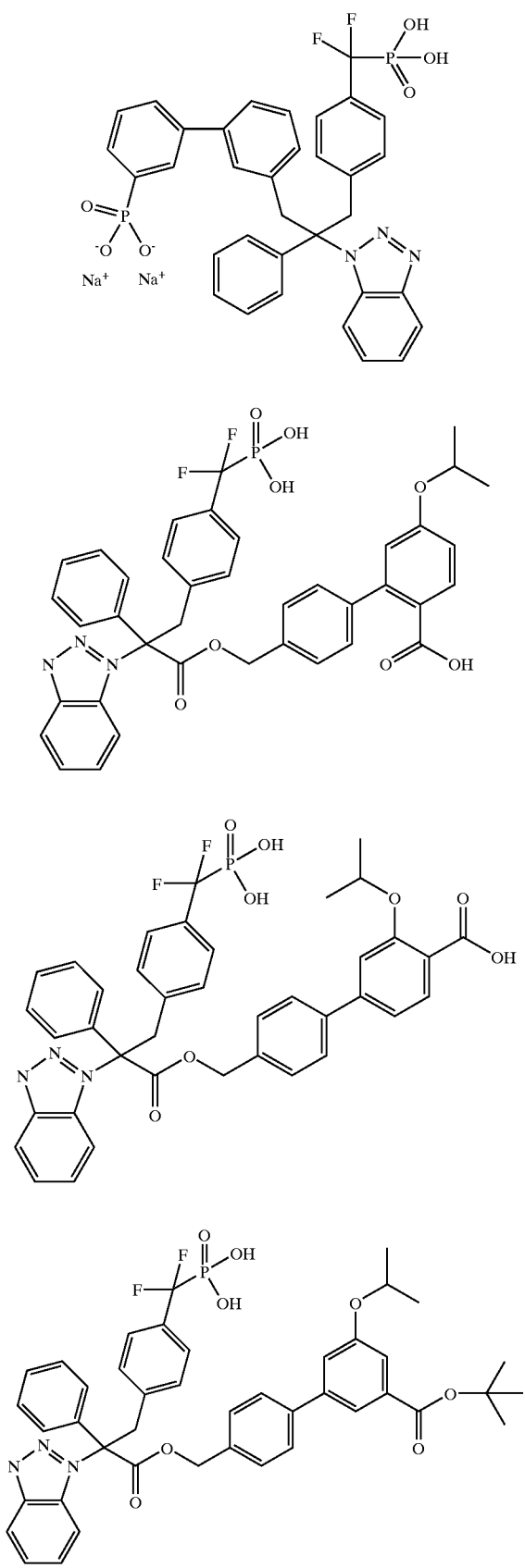
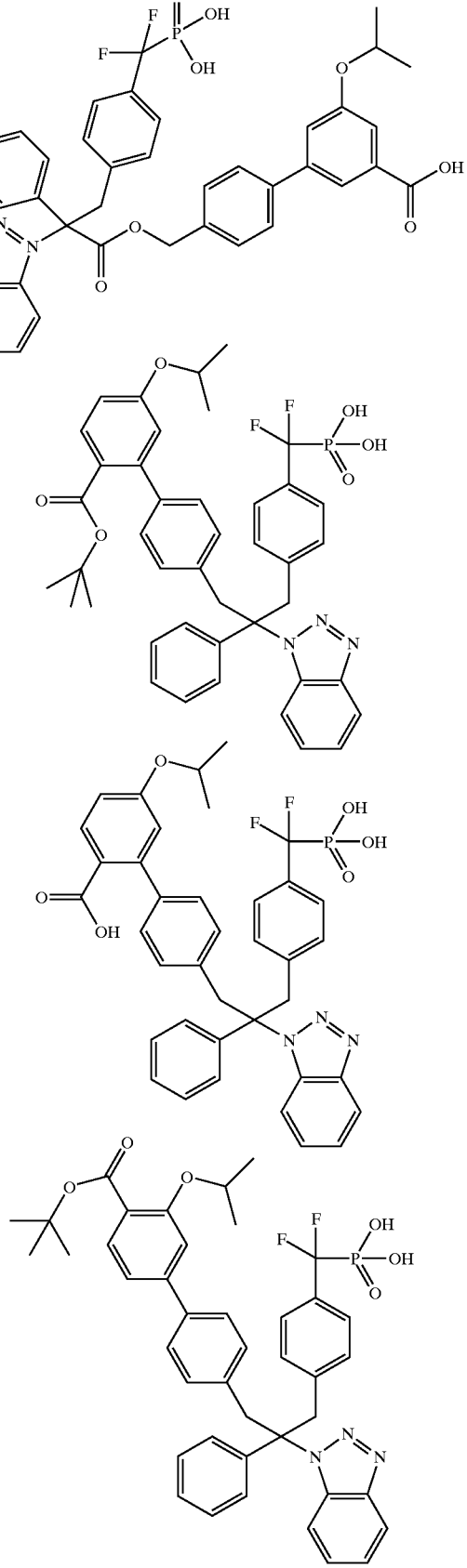

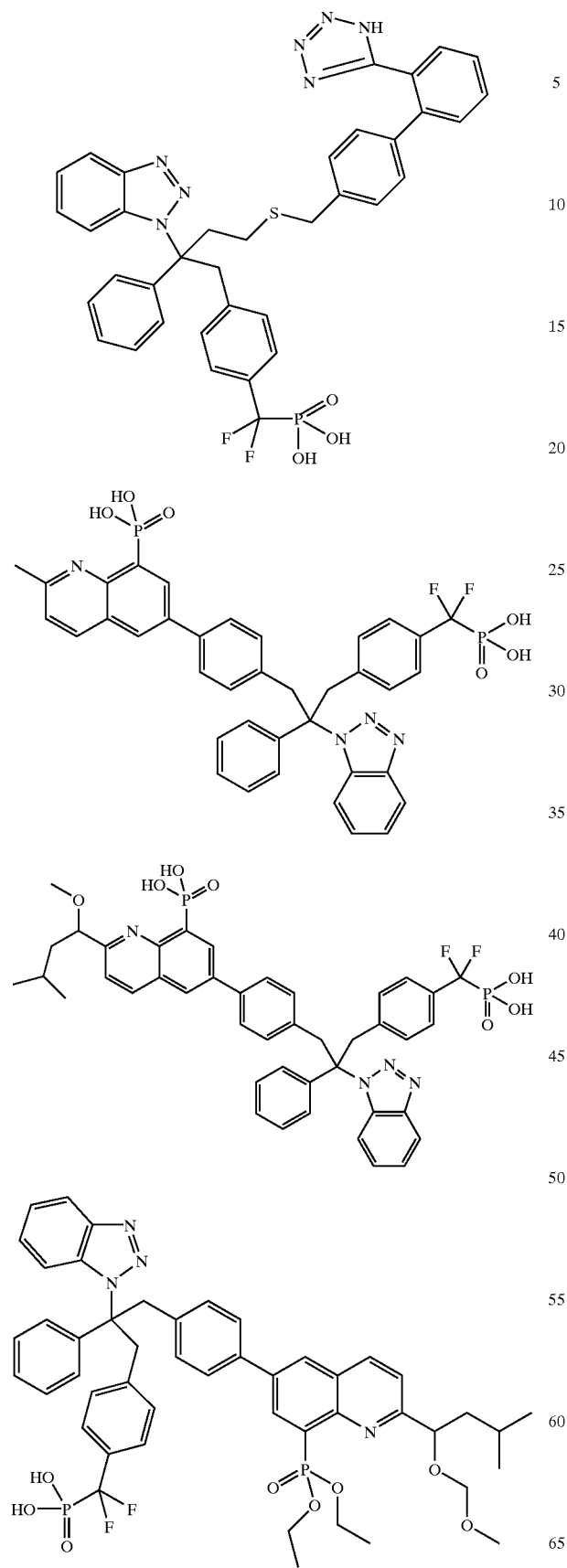
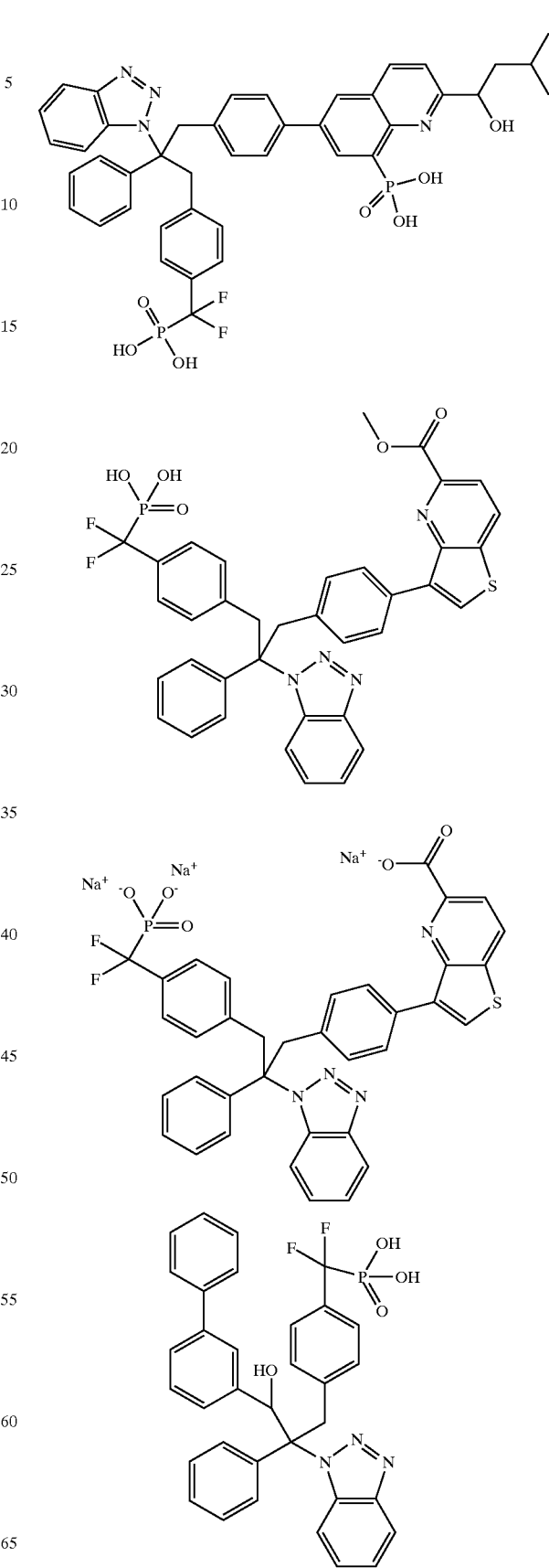

87
88
-continued
-continued
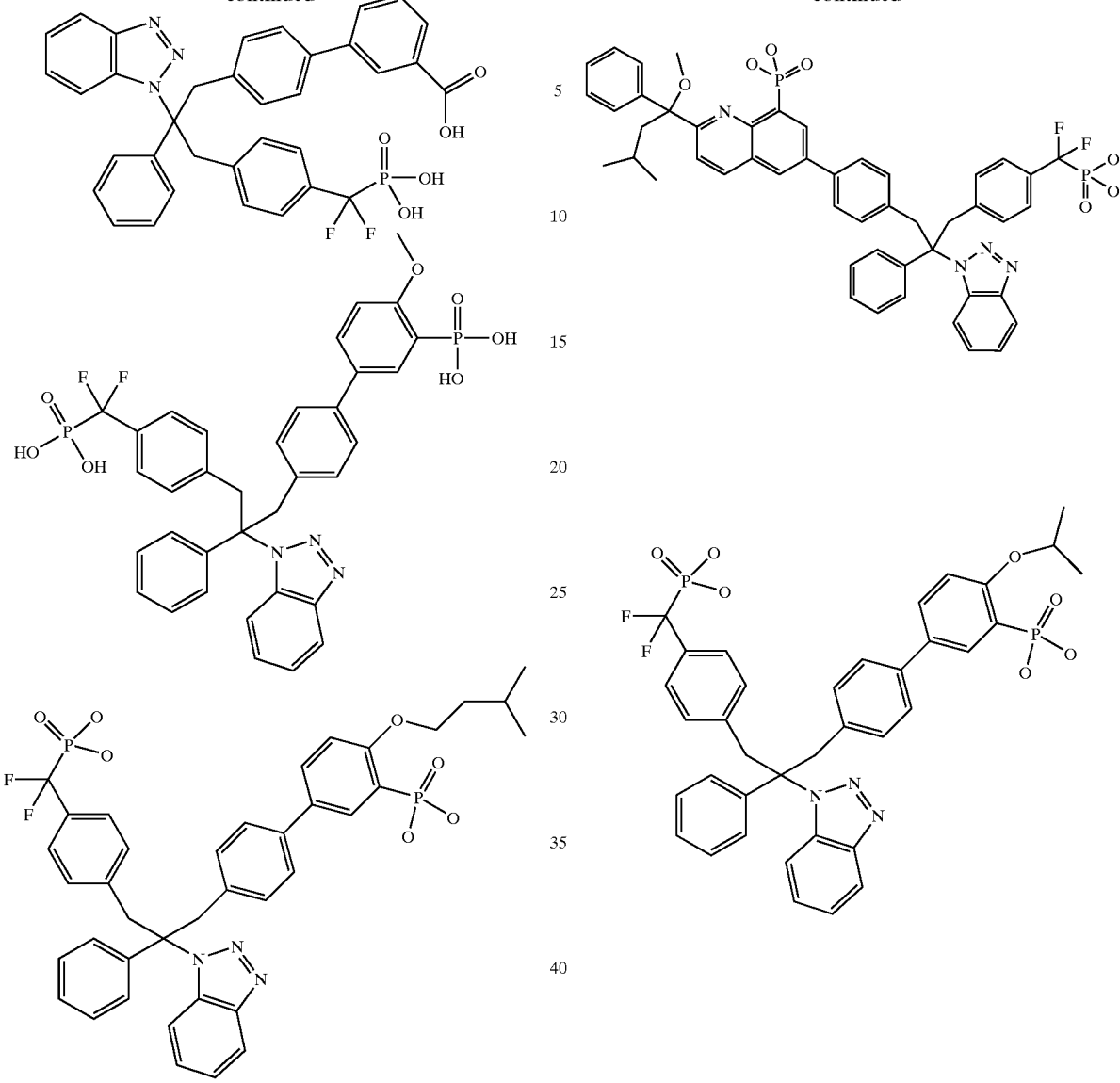

What is claimed is:

1. A compound represented by formula I:

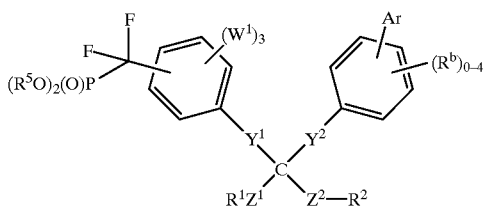

I or a pharmaceutically acceptable salt or prodrug thereof, wherein:

R$^1$ and R$^2$ are selected from the group consisting of: C$_{1-10}$alkyl(R$^a$)$_{0-7}$, C$_{2-10}$alkenyl(R$^a$)$_{0-7}$, Aryl(R$^a$)$_{0-3}$ and Het(R$^a$)$_{0-3}$;

wherein, each R$^a$ independently represents a member selected from the group consisting of: Aryl, OH, halogen, C$_{0-6}$alkyleneCO$_2$H, C$_{0-6}$alkyleneCO$_2$C$_{1-6}$ alkyl, OC$_{1-10}$alkyl, C$_{1-6}$alkyl, C$_{1-6}$haloalkyl, OC$_{1-10}$alkyleneCO$_2$H, S(O)$_y$C$_{1-6}$alkyl, S(O)$_y$NR$^{3'}$R$^{4'}$, and Het, wherein y is 0, 1, or 2;

Ar represents Aryl or Het, wherein said Aryl or Het is substituted with 1-5 substituents R$^b$, wherein optionally 2 R$^b$ groups can join together to form a 5–7 membered ring fused to Ar, where the fused portion of the 5–7 membered ring may be saturated or may include 1–2 double bonds and may include 1–4 heteroatoms selected from N, S, O, and C(=O) in the fused portion of the ring, said ring optionally being substituted from 1–3 groups independently selected from R$^a$;

Aryl is a 6–14 membered carbocyclic aromatic ring system comprising 1–3 phenyl rings, wherein said rings are fused together when there is more than one aromatic ring;

Het represents a 5–10 membered aromatic ring system comprising one ring or two fused rings, 1–4 heteroatoms, 0–4 of which are N atoms and 0–2 of which are O or S(O)$_y$ wherein y is 0–2, and 0–2 carbonyl groups;

Each y is 0, 1 or 2;

Each R$^b$ is independently selected from the group consisting of: OH, CN, halogen, C$_{0-6}$alkyleneOC$_{1-6}$alkyl (R$^a$)$_{0-7}$, C$_{0-6}$alkyleneOAryl(R$^a$)$_{0-7}$, Het, C$_{0-6}$alkyleneS (O)$_y$C$_{1-6}$alkyl(R$^a$)$_{0-7}$, with y equal to 0-2, C$_{0-6}$alkyleneS(O)$_3$H, C$_{1-10}$alkyl(R$^a$)$_{0-7}$, N$_3$, C$_{0-6}$alkyleneCO$_2$H, C$_{0-6}$alkyleneCO$_2$C$_{1-6}$alkyl(R$^a$)$_{0-7}$, C$_{0-6}$alkyleneCO$_2$C$_{2-6}$ alkenyl(R$^a$)$_{0-7}$, C$_{0-6}$alkyleneC(O)C$_{1-6}$alkyl(R$^a$)$_{0-7}$, C(O)NR$^{3'}$R$^{4'}$, s(O)$_y$NR$^{3'}$R$^{4'}$, NR$^{3'}$R$^{4'}$, PO(OR$^5$)$_2$, and CF$_2$PO(OR$^5$)$_2$, wherein R$^{3'}$ and R$^{4'}$ are as defined above;

Each R$^5$ is H;

Y$^1$, Y$^2$, Z$^1$ and Z$^2$ each independently represents —(CR$^3$R$^4$)$_a$—X—(CR$^3$R$^4$)$_b$— wherein a and b are each zero or an integer 1 or 2 such that the sum of a and b equals 0, 1, 2 or 3, X represents a bond, O, S(O)$_y$, NR$^{3'}$, C(O), OC(O), C(O)O, C(O)NR$^{3'}$, NR$^{3'}$C(O) or —CH=CH—, where y is as previously defined;

R$^3$ and R$^4$ are independently H, halogen, C$_{1-10}$alkyl or C$_{1-10}$haloalkyl;

R$^{3'}$ is selected from the group consisting of: H, C$_{1-6}$alkyl, C$_{1-6}$haloalkyl, OH, C(O)C$_{1-6}$ alkyl, C(O)Aryl, C(O) Het, C(O)C$_{1-6}$ haloalkyl, Aryl and Het;

R$^{4'}$ is selected from the group consisting of: H, C$_{1-6}$alkyl, C$_{1-6}$haloalkyl, Aryl and Het;

Each W$^1$ is independently selected from the group consisting of: H, OH, CN, halogen, OC$_{1-6}$alkyl(R$^a$)$_{0-7}$, OAryl(R$^a$)$_{0-7}$, S(O)$_y$C$_{1-6}$alkyl(R$^a$) with y equal to 0-2, S(O)$_3$H, C$_{1-6}$alkyl(R$^a$)$_{0-7}$, N$_3$, C$_{0-6}$alkyleneCO$_2$H, C$_{0-6}$alkyleneCO$_2$C$_{1-6}$alkyl(R$^a$)$_{0-7}$, C$_{0-6}$alkyleneCO$_2$C$_{2-6}$ alkenyl(R$^a$)$_{0-7}$, C$_{0-6}$alkyleneC(O)C$_{1-6}$alkyl(R$^a$)$_{0-7}$, C(O)NR$^{3'}$R$^{4'}$, S(O)$_y$NR$^{3'}$R$^{4'}$, NR$^{3'}$R$^{4'}$, Aryl and Het, wherein R$^{3'}$ and R$^{4'}$ are as defined above; or alternatively two W$^1$ groups on adjacent atoms of the aromatic ring are joined together to form a fused phenyl ring, optionally substituted with 1–3 groups R$^b$.

2. A compound in accordance with claim 1 wherein W$^1$ is independently selected from the group consisting of:
(a) hydrogen,
(b) halogen,
(c) OC$_{1-6}$alkyl(R$^a$)$_{0-7}$,
(d) SC$_{1-6}$alkyl(R$^a$)$_{0-7}$,
(e) C$_{1-6}$alkyl(R$^a$)$_{0-7}$,
(f) CO$_2$H,
(g) CO$_2$-C$_{1-6}$alkyl(R$^a$)$_{0-7}$,
(h) OH,
(l) N(R$^{3'}$)(R$^{4'}$) and
(m) C(O)C$_{1-6}$alkyl(R$^a$)$_{0-7}$.

3. A compound in accordance with claim 2 wherein each W$^1$ represents H or halogen.

4. A compound in accordance with claim 1 wherein Ar represents phenyl, quinolinyl, indolyl or thienopyridinyl.

5. A compound in accordance with claim 4 wherein Ar represents phenyl, which is substituted with 1-2 substituents selected from R$^b$, and the phenyl ring to which Ar is connected is unsubstituted.

6. A compound of Formula I as recited in claim 1, wherein Y$^1$, Z$^1$ and Z$^2$ are each independently CH$_2$ or a bond, and Y2 is selected from CH$_2$, a bond, —CH$_2$CH$_2$SCH$_2$—, —CH$_2$CH$_2$—, —C(=O)OCH$_2$—, —C(=O)OCH$_2$CH$_2$—, and —C(=O)O—.

7. A compound of Formula I as recited in claim 1, wherein R$^b$ is selected from the group consisting of: halogen, $C_{0-6}$alkyleneO$C_{1-6}$alkyl$(R^a)_{0-2}$, —S$C_{1-6}$alkyl$(R^a)_{0-2}$, -Ophenyl, tetrazole, $C_{1-10}$alkyl$(R^a)_{0-2}$, $C_{0-3}$alkyleneCO$_2$H, $C_{0-3}$alkyleneCO$_2C_{1-6}$alkyl$(R^a)_{0-2}$, C(O)NR$^{3'}$R$^{4'}$, S(O)$_y$NR$^{3'}$R$^{4'}$, PO(OR$^5$)$_2$, and CF$_2$PO(OR$^5$)$_2$, wherein R$^{3'}$ and R$^{4'}$ are individually selected from H and $C_{1-6}$alkyl, and $R^a$ is selected from OH, —O$C_{1-3}$alkyl, and phenyl.

8. A compound in accordance with claim 1, wherein R$^1$ and R$^2$ are selected from Aryl$(R^a)_{0-3}$ and Het$(R^a)_{0-3}$.

9. A compound in accordance with claim 1 wherein R$_1$ and R$_2$ are selected from phenyl and 1H-1,2,3-Benzotriazolyl.

10. A compound of Formula I as described in Examples 1–27, or a pharmaceutically acceptable salt or prodrug thereof:

Example 1: {[4-(2-Benzotriazol-1-yl-3-biphenyl-4-yl-2-phenyl-propyl)-phenyl]difluoro-methyl}-phosphonic acid Example 2: ({4-[2-Benzotriazol-1-yl-2-phenyl-3-(2'-sulfamoyl-biphenyl-4-yl)-propyl]-phenyl}-difluoro-methyl)-phosphonic acid Example 3: [(4-{2-Benzotriazol-1-yl-2-phenyl-3-[2'-(1H-tetrazol-5-yl)-biphenyl-4-yl]-propyl}-phenyl)-difluoro-methyl]-phosphonic acid Example 4: (4'-{2-Benzotriazol-1-yl-3-[4-(difluoro-phosphono-methyl)-phenyl]-2-phenyl-propyl}-biphenyl-3-yl)-phosphonic acid diethyl ester Example 5: (4'-{2-Benzotriazol-1-yl-3-[4-(difluoro-phosphono-methyl)-phenyl]-2-phenyl-propyl}-biphenyl-3-yl)-phosphonic acid Example 6: ({4-[2-Benzotriazol-1-yl-3-(4'-methylsulfanyl-biphenyl-4-yl)-2-phenyl-propyl]-phenyl}-difluoro-methyl)-phosphonic acid Example 7: (4-{2-(1H-1,2,3-Benzotriazol-1-yl)-3-[4'(methylsulfanyl) (1,1'-biphenyl]yl]phenylpropyl}phenyl)(difluoro)methylphosphonic acid Example 8: {4-[2-(1H-1,2,3-Benzotriazol-1-yl)-3-(3'phenoxy(1,1'-biphenyl]-3-yl)-2-phenylpropyl)phenyl}-(difluoro)methylphosphonic acid.

Example 9: 3-(2-(1H-1,2,3-Benzotriazol-1-yl)-3-(4-[difluoro(phosphono)methyl]phenyl}-2-phenylpropyl)(1,1'-biphenyl)]-3-ylphosphonic acid Example 10: {4-[2-(1H-1,2,3-Benzotriazol-1-yl)-3-[(4-(2-carboxy-5-isopropoxyphenyl)benzyl)oxy]-3-oxo-2-phenylpropyl]phenyl}(difluoro)methylphosphonic acid Example 11: {4-[2-(1H-1,2,3-Benzotriazol-1-yl)-3-[(4-(4-carboxy-3-isopropoxyphenyl)benzyl)oxy]-3-oxo-2-phenylpropyl]phenyl}(difluoro)methylphosphonic acid Example 12: {4-[2-(1H-1,2,3-Benzotriazol-1-yl)-3-[(4-(3-t-butoxycarbonyl-5-isopropoxyphenyl)benzyl)oxy]-3-oxo-2-phenylpropyl]phenyl}(difluoro) methylphosphonic acid Example 13: {4-[2-(1H-1,2,3-Benzotriazol-1-yl)-3-[(4-(3-carboxy-5-isopropoxyphenyl)benzyl)oxy]-3-oxo-2-phenylpropyl]phenyl}(difluoro)methylphosphonic acid Example 14: (4-{2-(1H-1,2,3-Benzotriazol-1-yl)-3-[2'-(tert-butoxycarbonyl)-5'-isopropoxy(1,1'-biphenyl]-4-yl]-2-phenylpropyl}phenyl)(difluoro) methylphosphonic acid Example 15: (4'-(2-(1H-1,2,3-Benzotriazol-1-yl)-3-{4-[difluoro(phosphono)methyl]phenyl}-2-phenylpropyl)-5-isopropoxy[1,1'-biphenyl]-2-carboxylic acid Example 16: (4-{2-(1H-1,2,3-benzotriazol-1-yl)-3-[4'-(tert-butoxycarbonyl)-3'-isopropoxy[1,1'-biphenyl]-4-yl]-2-phenylpropyl}phenyl) (difluoro) methylphosphonic acid Example 17: (4-{2-Benzotriazol-1-yl-4-[2'-(1H-tetrazol-5-yl)-biphenyl-4-ylmethylsulfanyl]-2-phenyl-butyl}-phenyl)-difluoro-methyl-phosphonic acid Example 18: [6-(4-{2-Benzotriazol-1-yl-3-[4-(difluoro-phosphono-methyl)-phenyl]-2-phenyl-propyl}-phenyl)-2-methyl-quinolin-8-yl]-phosphonic acid Example 19: [6-(4-{2-Benzotriazol-1-yl-3-[4-(difluoro-phosphono-methyl)-phenyl] -2-phenyl-propyl}-phenyl)-2-(1-methoxy-3-methyl-butyl)-quinolin-8-yl]-phosphonic acid Example 20: [6-(4-{2-Benzotriazol-1-yl-3-[4-(difluoro-phosphono-methyl)-phenyl]-2-phenyl-propyl}-phenyl)-2-(1-methoxymethoxy-3-methyl-butyl)-quinolin-8-yl]-phosphonic acid diethyl ester Example 21: [6-(4-{2-Benzotriazol-1-yl-3-[4-(difluoro-phosphono-methyl)-phenyl]-2-phenyl-propyl}-phenyl)-2-(1-hydroxy-3-methyl-butyl)-quinolin-8-yl]-phosphonic acid Example 22: [(4-{2-Benzotriazol-1-yl-3-[4-(5-methoxycarbonyl-thieno[3,2-b-pyridin-3-yl)-phenyl]-2-phenyl-propyl}-phenyl)-difluoro-methyl]-phosphonic acid Example 23 3-(4-{2-Benzotriazol-1-yl-3-[4-(difluoro-phosphono-methyl)-phenyl]-2-phenyl-propyl}-phenyl)-thieno[3,2-b]pyridine-5-carboxylic acid trisodium salt Example 24: [4-(1-Benzotriazol-1-yl-2-biphenyl-3-yl-2-hydroxy-1-phenylethyl)phenyl] difluoromethylphosphonic acid Example 25: 4'(2-(1H-1,2,3-Benzotriazol-1-yl)-3-{4-[difluoro(phosphono)methyl]phenyl}-2-phenylpropyl)(1,1'-biphenyl]-3-carboxylic acid Example 26: 4'-{2-Benzotriazol-1-yl-3-[4-(difluorophosphonomethy)phenyl]-2-phenylpropyl}-4-methoxybiphenyl-3-yl-phosphonic acid and Example 27: 4'-{2-Benzotriazol-1-yl-3-[4-(difluorophosphonomethy)phenyl]-2-phenylpropyl}-4-(3-methylbutoxy)biphenyl-3-yl-phosphonic acid.

11. A compound having the formula I as recited in claim 1, or a pharmaceutically acceptable salt thereof, wherein each group —OR$^5$ is selected from —OH and a group that is converted to —OH under physiological conditions during or after administration to a mammalian patient, thereby yielding a phosphonic acid group, or a salt thereof, wherein at least one group —OR$^5$ is not an —OH group, wherein all substituent groups other than R$^5$ are as defined in claim 1.

12. A compound as recited in claim 11, wherein one group R$^5$ is selected from $C_{1-6}$alkyl, phenyl, —CHR'phenyl and —CHR'OC(=O)R", and the remaining groups R$^5$ are independently selected from H, $C_{1-6}$alkyl, phenyl, —CHR'phenyl and —CHR'OC(=O)R", wherein each R' is H or $C_{1-6}$alkyl, and each R" is —$C_{1-6}$alkyl or —O$C_{1-6}$alkyl, wherein $C_{1-6}$alkyl and —O$C_{1-6}$alkyl in each occurrence are optionally substituted with one or more substituents independently selected from 1–5 halogen atoms, a phenyl group, or a mixture of these, and each phenyl in each occurrence is optionally substituted with 1–3 substituents independently selected from halogen, —CH$_3$, —CF$_3$, —OCH$_3$ and —OCF$_3$.

13. A compound as recited in claim 11, wherein all substituent groups R$^5$ that are not H are the same.

14. A pharmaceutical composition which is comprised of a compound in accordance with claim 1 in combination with a pharmaceutically acceptable carrier.

15. A pharmaceutical composition in accordance with claim 11 further comprising a second anti-diabetic or anti-obesity effective compound.

16. A method of treating, controlling or preventing diabetes and complications thereof in a mammalian patient in need of such treatment comprising administering to said patient an anti-diabetic effective amount of a compound in accordance with claim 1.

17. A method of treating, controlling or preventing obesity in a mammalian patient in need of such treatment comprising administering to said patient an anti-obesity effective amount of a compound in accordance with claim 1.

18. A method in accordance with claim 16, further comprising administering to said patient a second anti-diabetic compound or an anti-obesity compound in an amount effective to treat, control or prevent diabetes or obesity.

19. A method in accordance with claim 17, further comprising administering to said patient a second anti-obesity compound or an anti-diabetic compound in an amount effective to treat, control or prevent obesity or diabetes.

20. A pharmaceutical composition in accordance with claim 14 further comprising an HMG-CoA reductase inhibitor.

21. A method in accordance with claim 16, further comprising administering to said patient an effective amount of an HMG-CoA reductase inhibitor.

22. A method for treating, controlling or preventing atherosclerosis in a mammalian patient in need of such treatment comprising administering to said patient an effective amount of a compound of claim 1 and an effective amount of an HMG-CoA reductase inhibitor.

23. A method of treating, preventing, or controlling one or more diseases or conditions selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, said method comprising the administration of an effective amount of the compound of claim 1.

24. A method of treating, preventing, or controlling one or more diseases or conditions, selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, said method comprising the administration of an effective amount of the compound of claim 1 and the administration of an effective amount of one or more pharmaceutically active compounds selected from the group consisting of an HMG-CoA reductase inhibitor, an anti-obesity agent, and an antidiabetic compound.

25. A pharmaceutical composition for the treatment, prevention or control of one or more diseases or conditions selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, said composition comprising an effective amount of a compound of claim 1 and a pharmaceutically acceptable carrier.

26. A pharmaceutical composition for the treatment, prevention or control of one or more diseases or conditions, selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, said composition comprising (1) an effective amount of the compound of claim 1, (2) an effective amount of one or more pharmaceutically active compounds selected from the group consisting of an HMG-CoA reductase inhibitor, an anti-obesity agent, and an anti-diabetic agent, and (3) a pharmaceutically acceptable carrier.

27. A pharmaceutical composition for the treatment, prevention or control of one or more diseases or conditions, selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, said composition comprising:

(1) an effective amount of the compound of claim 1, (2) an effective amount of one or pharmaceutically active compounds selected from the group consisting of:

(a) insulin sensitizers including (i) PPARγ agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin;

(b) insulin or insulin mimetics;

(c) sulfonylureas such as tolbutamide and glipizide, or related materials;

(d) α-glucosidase inhibitors (such as acarbose);

(e) cholesterol lowering agents such as (i) HMG-CoA reductase inhibitors (lovastatin, simvastatin and pravastatin, fluvastatin, atorvastatin, rivastatin and other statins), (ii) sequestrants (cholestyramine, colestipol and a dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and benzafibrate), (v) inhibitors of cholesterol absorption for example beta-sitosterol and (acyl CoA:cholesterol acyltransferase) inhibitors for example melinamide and (vi) probucol;

(f) PPARα/γ agonists;

(g) antiobesity compounds such as appetite suppressants, fenfluramine, dexfenfluramine, phentiramine, sulbitramine, orlistat, neuropeptide Y5 inhibitors (NP Y5 receptor antagonosts), leptin, which is a peptidic hormone, $\beta_3$ adrenergic receptor agonists, and PPARγ antagonists and partial agonists;

(h) ileal bile acid transporter inhibitors; and (i) insulin receptor activators; and (3) a pharmaceutically acceptable carrier.

28. A compound having any of the structures shown below, or a pharmaceutically acceptable salt or prodrug thereof: